(12) United States Patent
Wang et al.

(10) Patent No.: US 12,404,341 B2
(45) Date of Patent: Sep. 2, 2025

(54) GLYPICAN-3 (GPC-3) ANTIBODIES

(71) Applicant: AGENCY FOR SCIENCE, TECHNOLOGY AND RESEARCH, Connexis (SG)

(72) Inventors: Cheng-I Wang, Singapore (SG); Bei Wang, Singapore (SG); Zi Xian Eve Ngoh, Singapore (SG); Wen-Hsin Lee, Singapore (SG); Ching-Wen Huang, Singapore (SG); Yee Chin Yvonne Yeap, Singapore (SG)

(73) Assignee: AGENCY FOR SCIENCE, TECHNOLOGY AND RESEARCH, Connexis (SG)

( * ) Notice: Subject to any disclaimer, the term of this patent is extended or adjusted under 35 U.S.C. 154(b) by 945 days.

(21) Appl. No.: 17/441,519

(22) PCT Filed: Mar. 22, 2020

(86) PCT No.: PCT/SG2020/050152
§ 371 (c)(1),
(2) Date: Sep. 21, 2021

(87) PCT Pub. No.: WO2020/190217
PCT Pub. Date: Sep. 24, 2020

(65) Prior Publication Data
US 2022/0162335 A1    May 26, 2022

(30) Foreign Application Priority Data
Mar. 21, 2019   (SG) .............................. 10201902550P

(51) Int. Cl.
| | |
|---|---|
| *C07K 16/30* | (2006.01) |
| *A61K 38/17* | (2006.01) |
| *A61K 39/395* | (2006.01) |
| *A61K 47/68* | (2017.01) |
| *A61P 35/00* | (2006.01) |
| *C07K 14/725* | (2006.01) |
| *C07K 16/28* | (2006.01) |

(52) U.S. Cl.
CPC ........ *C07K 16/303* (2013.01); *A61K 38/1774* (2013.01); *A61K 39/3955* (2013.01); *A61K 47/6849* (2017.08); *A61P 35/00* (2018.01); *C07K 14/7051* (2013.01); *C07K 16/2809* (2013.01); *C07K 2317/24* (2013.01); *C07K 2317/56* (2013.01); *C07K 2317/622* (2013.01); *C07K 2317/92* (2013.01)

(58) Field of Classification Search
CPC ............. C07K 16/303; C07K 14/7051; C07K 16/2809; C07K 2317/24; C07K 2317/56; C07K 2317/622; C07K 2317/92; C07K 2317/33; C07K 16/2818; C07K 2317/31; C07K 2317/55; C07K 2317/732; C07K 2319/02; C07K 14/705; A61K 38/1774; A61K 39/3955; A61K 47/6849; A61K 2039/505; A61K 2039/507; A61P 35/00; G01N 33/57438
See application file for complete search history.

(56) References Cited

U.S. PATENT DOCUMENTS

| | | |
|---|---|---|
| 7,919,086 B2 | 4/2011 | Nakano et al. |
| 2010/0209432 A1 | 8/2010 | Terrette et al. |
| 2014/0186892 A1 | 7/2014 | Terrett et al. |
| 2016/0215261 A1 | 7/2016 | Li et al. |
| 2019/0046659 A1* | 2/2019 | Wang ................. C07K 14/7151 |

FOREIGN PATENT DOCUMENTS

| | | |
|---|---|---|
| CN | 101377506 A | 3/2009 |
| CN | 103743902 A | 4/2014 |
| WO | WO 2015/179658 A2 | 11/2015 |

OTHER PUBLICATIONS

Schreiner, C. L., et al. "Defective vasculature in fibronectin-receptor-deficient cho cell tumors in nude mice." International journal of cancer 55.3 (1993): 436-441. (Year: 1993).*
Ho, David H., et al. "Soluble tumor necrosis factor-like weak inducer of apoptosis overexpression in HEK293 cells promotes tumor growth and angiogenesis in athymic nude mice." Cancer research 64.24 (2004): 8968-8972. (Year: 2004).*
First Office Action of Chinese Application No. CN202080036994.6 dated Nov. 29, 2023, 15 pages.
International Search Report in corresponding PCT Application No. PCT/SG2020/050152, mailed Sep. 11, 2020.
Feng M. and Ho M., Glypican-3 antibodies: a new therapeutic target for liver Cancer, *FEBS Lett.*, Oct. 15, 2013, vol. 588, No. 2, pp. 377-382.
Feng M. et al., Therapeutically targeting glypican-3 via a conformation specific single-domain antibody in hepatocellular carcinoma, *Proc Natl Acad Sci USA*, Mar. 5, 2013, vol. 110, No. 12, pp. E1083-E1091.
Zhang Y-F. and Ho M., Humanization of high-affinity antibodies targeting glypican-3 in hepatocellular carcinoma, *Sci Rep.*, Sep. 26, 2016, No. 6, pp. 33878: 1-11.
Ortiz M.V. et al., Immunotherapeutic Targeting of GPC3 in Pediatric Solid Embryonal Tumors. *Front Oncol.*, Feb. 26, 2019, No. 9, pp. 108: 1-8.
Wang Y. etal., A GPC3- targeting Bispecific Antibody, GPC3-S-Fab, with Potent Cytotoxicity *J Vis Exp.*, Jul. 12, 2018, No. 137, pp. 57588: 1-8.

* cited by examiner

*Primary Examiner* — Julie Wu
*Assistant Examiner* — Bryan William Heck
(74) *Attorney, Agent, or Firm* — Leason Ellis LLP

(57) ABSTRACT

We describe an antibody or antigen-binding fragment thereof comprising a heavy chain variable region ($V_H$) sequence and a light chain variable region ($V_L$) sequence of a clone selected from: 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1 which is capable of specifically binding to glypican-3 (GPC-3) (GenBank Accession Number: NP_004475.1), or a sequence having at least 75%, 80%, 85%, 90%, 95%, 96%, 97%, 98% or 99% sequence identity thereto.

24 Claims, 15 Drawing Sheets
Specification includes a Sequence Listing.

GLYPICAN-3 (GPC-3) ANTIBODIES

CROSS-REFERENCE TO RELATED PATENT APPLICATIONS

This application is a U.S. National Phase Application under 35 U.S.C. § 371 of International Patent Application No. PCT/SG2020/050152, filed Mar. 22, 2020, and claims priority to Singapore Application No. 10201902550P, filed Mar. 21, 2019, all of which are incorporated by reference in their entireties. The International Application was published on Sep. 24, 2020 as International Publication No. WO 2020/190217 A1.

FIELD

This invention relates to the fields of medicine, cell biology, molecular biology and genetics. This invention relates to the field of medicine.

BACKGROUND

Unmet Need for Novel Treatment Strategies for Hepatocellular Carcinoma (HCC)

Hepatocellular carcinoma (HCC) is the sixth most common cancer worldwide, with a reported global incidence of 854,000 in 2015.

More than half of the HCC cases worldwide occur in developing countries due to prevalent chronic Hepatitis B Virus (HBV) infections. HCC is also the fourth leading cause of cancer-associated mortality.

A great majority of patients are ineligible for curative therapies upon diagnosis as they are often in the late stages of the disease and the outcome of systemic therapy for HCC has been disappointing.

The dominant targeted therapy drug for HCC is Nexavar (Sorafenib, Bayer), a small molecule inhibitor for multiple protein kinases. However, even with its substantial usage in HCC treatment, Sorafenib only shows marginal clinical benefits with a low response rate and provides very limited improvement for overall survival. Since its launch in 2007, no new drugs have entered the market, indicating that development of new treatments for HCC is very challenging.

Hence, there is still an urgent medical need to discover novel treatment strategies for HCC.

SUMMARY

According to a $1^{st}$ aspect of the present invention, we provide an antibody or antigen-binding fragment thereof comprising a heavy chain variable region ($V_H$) sequence and a light chain variable region ($V_L$) sequence of a clone selected from: 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1. The antibody or antigen-binding fragment thereof may be capable of specifically binding to glypican-3 (GPC-3) (GenBank Accession Number: NP_004475.1). It may be a sequence having at least 75%, 80%, 85%, 90%, 95%, 96%, 97%, 98% or 99% sequence identity to such a sequence.

The antibody or antigen-binding fragment may be such that the $V_H$ and $V_L$ sequence are selected from: SEQ ID NO: 1 and SEQ ID NO: 2; SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; SEQ ID NO: 11 and SEQ ID NO: 12; SEQ ID NO: 13 and SEQ ID NO: 14; SEQ ID NO: 15 and SEQ ID NO: 16; SEQ ID NO: 17 and SEQ ID NO: 18; SEQ ID NO: 19 and SEQ ID NO: 20; SEQ ID NO: 21 and SEQ ID NO: 22; SEQ ID NO: 23 and SEQ ID NO: 24; SEQ ID NO: 25 and SEQ ID NO: 26; SEQ ID NO: 27 and SEQ ID NO: 28; SEQ ID NO: 29 and SEQ ID NO: 30; SEQ ID NO: 31 and SEQ ID NO: 32; SEQ ID NO: 33 and SEQ ID NO: 34; SEQ ID NO: 35 and SEQ ID NO: 36; SEQ ID NO: 37 and SEQ ID NO: 38; SEQ ID NO: 39 and SEQ ID NO: 40; SEQ ID NO: 41 and SEQ ID NO: 42; SEQ ID NO: 43 and SEQ ID NO: 44; SEQ ID NO: 45 and SEQ ID NO: 46; and SEQ ID NO: 47 and SEQ ID NO: 48.

The antibody or antigen-binding fragment may be capable of binding to an epitope of human glypican-3 (GPC-3) with an affinity of 55 nm or less, 50 nm or less, 45 nm or less, 40 nm or less, 35 nm or less, 30 nm or less, 25 nm or less, 20 nm or less, 15 nm or less, 10 nm or less, 5 nm or less, 1 nm or less, 0.9 nM or less, 0.8 nM or less, 0.7 nM or less, 0.6 nM or less, 0.5 nM or less, 0.4 nM or less, 0.3 nM or less, 0.2 nM or less or 0.1 nM or less. The affinity may be measured as a EC50 as determined by ELISA.

The antibody or antigen-binding fragment may be capable of binding to a cell line selected from the group consisting of: HepG2 (GPC-3$^{High}$) and Hep3B (GPC-3$^{Medium}$).

The antibody or antigen-binding fragment may be capable of inducing Antibody-Dependent Cell-mediated Cytotoxicity (ADCC) of a GPC-3 expressing cell in the presence of natural killer (NK) cells.

The antibody or antigen-binding fragment may be a humanised antibody comprising a human constant region.

The antibody or antigen-binding fragment may comprise a monoclonal antibody, a humanised monoclonal antibody, an Fv, F(ab'), F(ab')$_2$ or single-chain Fv (scFv) fragment. It may comprise a single chain Fv fragment comprising a $V_H$ sequence and $V_L$ sequence.

The antibody or antigen-binding fragment may be a monoclonal antibody selected from the group consisting of: 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1.

The antibody or antigen-binding fragment may further comprise a heavy chain variable region ($V_H$) sequence and a light chain variable region ($V_L$) sequence capable of binding to CD3 (GenBank Accession Number: NM_000733.4).

The antibody or antigen-binding fragment may be further capable of specifically binding to CD-3 or a sequence having at least 75%, 80%, 85%, 90%, 95%, 96%, 97%, 98% or 99% sequence identity thereto.

The antibody or antigen-binding fragment may be such that the heavy chain variable region ($V_H$) sequence and a light chain variable region ($V_L$) sequence capable of binding to CD3 comprise the sequences set out in SEQ ID NO: 97 and SEQ ID NO: 98.

The antibody or antigen-binding fragment may be capable of activating T-cells.

There is provided, according to a $2^{nd}$ aspect of the present invention, a chimeric antigen receptor (CAR) comprising: (a) an antigen-binding fragment as set out above; (b) a transmembrane domain; and (c) a co-stimulatory intracellular signalling domain. We further provide a chimeric antigen receptor T Cell (CAR T) expressing such a chimeric antigen receptor.

We provide, according to a $3^{rd}$ aspect of the present invention, a nucleic acid capable of encoding an antibody or antigen-binding fragment as set out above. The nucleic acid may comprise sequences selected from the group consisting of: SEQ ID NO: 49 and SEQ ID NO: 50; SEQ ID NO: 51 and SEQ ID NO: 52; SEQ ID NO: 53 and SEQ ID NO: 54; SEQ ID NO: 55 and SEQ ID NO: 56; SEQ ID NO: 57 and SEQ ID NO: 58; SEQ ID NO: 59 and SEQ ID NO: 60; SEQ ID NO: 61 and SEQ ID NO: 62; SEQ ID NO: 63 and SEQ ID NO: 64; SEQ ID NO: 65 and SEQ ID NO: 66; SEQ ID NO: 67 and SEQ ID NO: 68; SEQ ID NO: 69 and SEQ ID NO: 70; SEQ ID NO: 71 and SEQ ID NO: 72; SEQ ID NO: 73 and SEQ ID NO: 74; SEQ ID NO: 75 and SEQ ID NO: 76; SEQ ID NO: 77 and SEQ ID NO: 78; SEQ ID NO: 79 and SEQ ID NO: 80; SEQ ID NO: 81 and SEQ ID NO: 82; SEQ ID NO: 83 and SEQ ID NO: 84; SEQ ID NO: 85 and SEQ ID NO: 86; SEQ ID NO: 87 and SEQ ID NO: 88; SEQ ID NO: 89 and SEQ ID NO: 90; SEQ ID NO: 91 and SEQ ID NO: 92; SEQ ID NO: 93 and SEQ ID NO: 94; and SEQ ID NO: 95 and SEQ ID NO: 96. The nucleic acid may be comprised in an expression vector.

As a 4$^{th}$ aspect of the present invention, there is provided a host cell comprising such a nucleic acid. The host cell may comprise a Chinese Hamster Ovary (CHO) or a HEK293 cell.

We provide, according to a 5$^{th}$ aspect of the present invention, a pharmaceutical composition comprising an antibody or antigen-binding fragment, CAR, CAR T, nucleic acid or host cell as set out above, together with a pharmaceutically acceptable excipient, diluent or carrier.

The present invention, in a 6$^{th}$ aspect, provides a compound comprising an antibody or antigen-binding fragment thereof, as shown above, linked to a cytotoxic agent. The linkage may be by means of a cleavable linker.

The compound may comprise an antibody-drug conjugate.

In a 7$^{th}$ aspect of the present invention, there is provided an antibody, antigen-binding fragment, CAR, CAR T, nucleic acid, host cell, pharmaceutical composition, compound or antibody-drug conjugate as described above for use in a method of treatment, prevention or alleviation of a cancer, such as hepatocellular carcinoma (HCC).

According to an 8$^{th}$ aspect of the present invention, we provide a method of producing an antibody or antigen-binding fragment, the method comprising expressing a nucleic acid as described above in a host cell, such as a host cell as set out above and optionally isolating the expressed antibody or antigen-binding fragment.

We provide, according to a 9$^{th}$ aspect of the invention, use of such an antibody, antigen-binding fragment, CAR, CAR T, nucleic acid, pharmaceutical composition, compound or antibody-drug conjugate in the preparation of a medicament for the treatment, prevention or alleviation of a cancer, such as hepatocellular carcinoma (HCC).

There is provided, in accordance with a 10$^{th}$ aspect of the present invention, a method of detecting a hepatocellular carcinoma (HCC) cell, the method comprising detecting modulation of expression, amount or activity of glypican-3 (GPC-3) in or of the cell, by means of an antibody or antigen-binding fragment set out above.

As an 11$^{th}$ aspect of the invention, we provide a method of diagnosing hepatocellular carcinoma (HCC) in an individual, in which the method comprises detecting, in a cell of the individual: a modulated expression level of glypican-3 (GPC-3) by contacting the cell with an antibody or antigen-binding fragment as described above; as compared to the expression level of glypican-3 in a cell of an individual known not to be suffering from hepatocellular carcinoma (HCC); in which an increased expression level of the glypican-3 indicates that the individual is suffering, or is likely to be suffering, from hepatocellular carcinoma (HCC).

We provide, according to a 12$^{th}$ aspect of the invention, there is provided a diagnostic kit for hepatocellular carcinoma (HCC), the kit comprising an antibody or antigen-binding fragment or a nucleic acid as set out above together with instructions for use.

The practice of this invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA Methods in Enzymology*, Academic Press; *Using Antibodies: A Laboratory Manual: Portable Protocol NO.* 1 by Edward Harlow, David Lane, Ed Harlow (1999, Cold Spring Harbor Laboratory Press, ISBN 0-87969-544-7); *Antibodies: A Laboratory Manual* by Ed Harlow (Editor), David Lane (Editor) (1988, Cold Spring Harbor Laboratory Press, ISBN 0-87969-314-2), 1855. *Handbook of Drug Screening*, edited by Ramakrishna Seethala, Prabhavathi B. Fernandes (2001, New York, NY, Marcel Dekker, ISBN 0-8247-0562-9); and *Lab Ref: A Handbook of Recipes, Reagents, and Other Reference Tools for Use at the Bench*, Edited Jane Roskams and Linda Rodgers, 2002, Cold Spring Harbor Laboratory, ISBN 0-87969-630-3. Each of these general texts is herein incorporated by reference.

BRIEF DESCRIPTION OF THE FIGURES

FIG. 4A is a drawing of a histogram of fluorescence intensity showing the mGPC-3 expression level on Hepa1-6-mGPC-3 cells and the parental Hepa1-6 cells.

FIG. 4B is a drawing of cells positively stained with different anti-GPC-3 antibodies were gated and the percentages (%) were calculated.

FIG. 9C and FIG. 9D are drawings showing percentage of T cells activated by different anti-GPC-3 bi-specific T cell-engaging antibodies at 3 different concentrations were calculated and presented as the total percentage of CD25+CD69− cells, CD25-CD69+ cells and CD25+CD69+ cells, after co-culture with (FIG. 9C) GPC-3$^{Positive}$ HepG2 cells or (FIG. 9D) GPC-3$^{Negative}$ SK-Hep1 cells.

FIG. 9E and FIG. 9F are drawings showing ELISA measurement of interferon-γ secretion from human T cells after 24 hours of co-culture with either (FIG. 9E) GPC-3$^{Positive}$ HepG2 cells or (FIG. 9F) GPC-3$^{Negative}$ SK-Hep1 cells with addition of different anti-GPC-3 bi-specific T cell-engaging antibodies at 3 different concentrations.

FIG. 9G and FIG. 9H are drawings showing ELISA measurement of IL-2 secretion from human T cells after 24 hours of co-culture with either (FIG. 9G) GPC-3$^{Positive}$ HepG2 cells or (FIG. 9H) GPC-3$^{Negative}$ SK-Hep1 cells with addition of different anti-GPC-3 bi-specific T cell-engaging antibodies at 3 different concentrations.

FIG. 10A is a drawing showing percentage of cytolysis of GPC-3$^{Positive}$ HepG2 cells mediated by activated human T cells with time-course measurement using xCelligence impedance assay up to 72 hours, upon treatment with 5 different anti-GPC-3 bi-specific T cell-engaging antibodies (clone 1C4, 1D2, 2B5, 4H1, and 5C4). Shown are mean % cytolysis±SD in duplicate wells.

FIG. 10B is a drawing showing percentage of cytolysis of 5 different anti-GPC-3 bi-specific T cell-engaging antibodies at different concentrations at the assay end point (72 hours).

(FIG. 11C) Six days after CAR T cell injection, blood serum from mice of Mock T group and CAR T group were analysed by Luminex assay and levels of representative cytokines are shown.

FIG. 12A is a drawing showing percentage of CAR expression on different anti-GPC-3 CAR T cells detected by flow cytometry analysis.

FIG. 12B is a drawing showing percentage of cytolysis of GPC-3$^{Positive}$ Hep3B cells and GPC-3$^{Negative}$ SK-Hep1 cells mediated by anti-GPC-3 CAR T cells with time-course measurement using xCelligence impedance assay up to 72 hours.

FIG. 12C and FIG. 12D are drawings showing two million of GPC-3$^{Positive}$ Hep3B cells were subcutaneously injected into the right flanks of NSG mice. Twenty-six days later, mice were grouped according to the tumor size (3-4 mice per group). Ten million of different anti-GPC-3 CAR T cells (clone 1D2, clone 4H1, and clone 5C4) or Mock T cells were intravenously injected into these mice via tail vein. Tumor size (FIG. 12C) and weight of each mouse (FIG. 12D) were measured and recorded every 3-4 days.

On Day 0, two million of GPC-3$^{Positive}$ Hep3B cells were subcutaneously injected into the right flank of NSG mice. Twenty-four days later, mice were grouped according to the measurable tumor size (4 mice per group). Ten million of anti-GPC-3 CAR T cells (clone 5C4) or Mock T cells were intravenously injected into these mice via tail vein. Ten days after CAR T cell injection (Day 34), all mice were intraperitoneal injected with anti-PD1 IgG$_4$ antibodies for a total of 5 times with an interval of 3-5 days. Tumor size (FIG. 13A) and weight of each mouse (FIG. 13B) were measured and recorded every 3-4 days.

Figure 13:
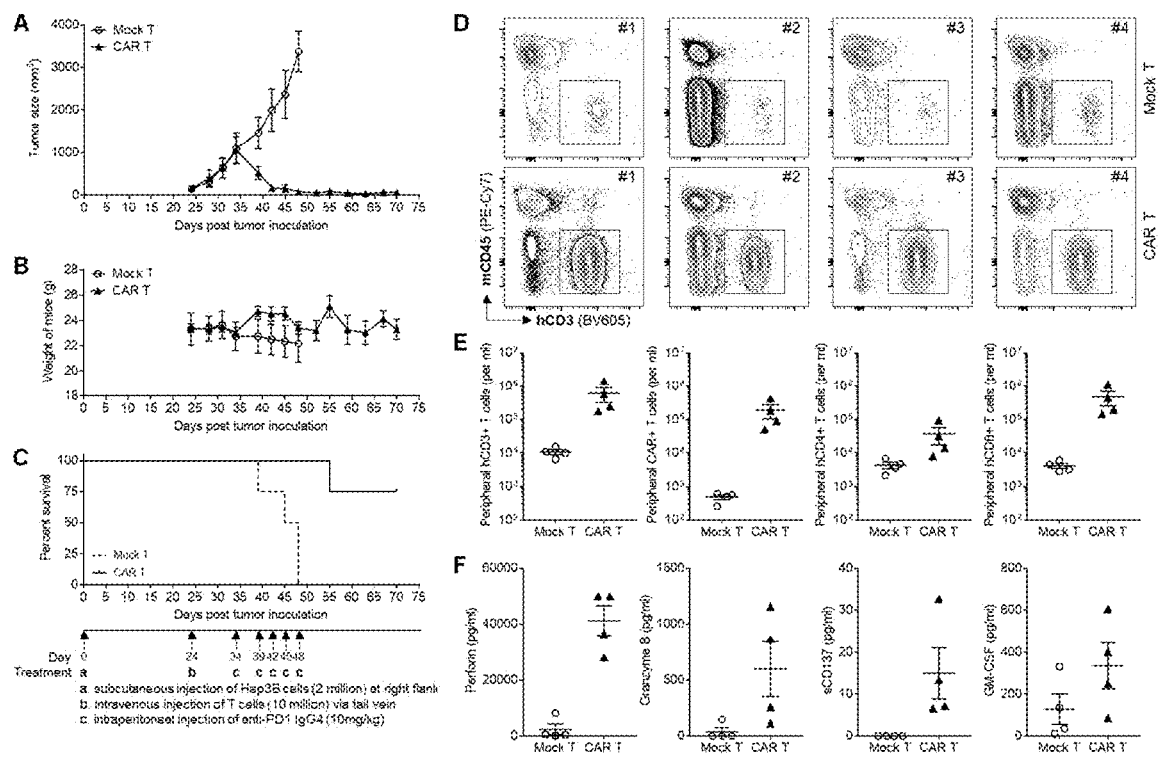
FIGS. 13A to 13F are drawings showing anti-GPC-3 CAR T cells eradicated large Hep3B tumor xenografts with a combinatorial use of anti-PD1 antibodies in vivo.
Figure 14:
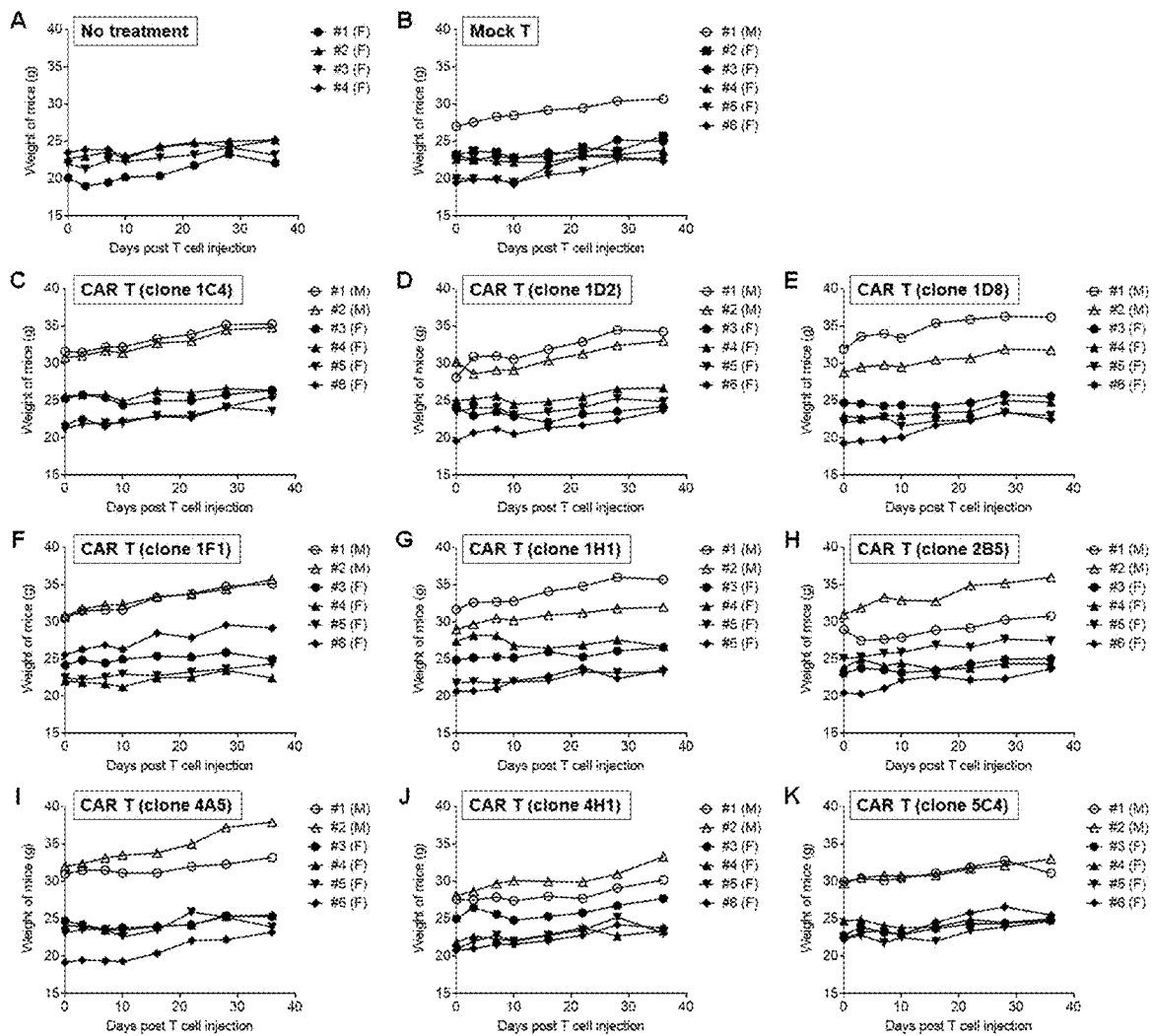

FIG. 13C is a drawing showing survival curves of the mice from both Mock T group (dotted line) and CAR T group. Death was defined either when autonomous death of the mice was observed or when the bearing tumor size of the mice exceeds 2000 mm³.

FIG. 13D is a drawing showing that sixteen days after CAR T cell injection, peripheral immune cells were analysed by flow cytometry analysis and the population of the human T cells were boxed.

FIG. 13E is a drawing showing the circulating concentrations of peripheral total T cells (CD3+), CAR T cells (CAR+CD3+), CD4 T cells (CD4+CD3+) and CD8 T cells (CD8+CD3+) were calculated and compared between Mock T and CAR T group of mice.

FIG. 13F is a drawing showing blood serum from mice of Mock T group and CAR T group were analysed by Luminex assay and levels of representative cytokines are shown.

FIGS. 14A to 14K are drawings showing that anti-GPC-3 CAR T cells did not induce toxicity in vivo. Nine different anti-GPC-3 antibody scFv sequences were used to generate anti-GPC-3 CAR T cells. NSG mice with mixed gender (M: male, F: female) were intravenously injected with ten million of Mock T cells (FIG. 14B) or different anti-GPC-3 CAR T cells (FIG. 14C to FIG. 14K) on Day 0. A group of mice without any treatment (FIG. 14A) was also included as healthy control. Body weight of each mouse was measured and recorded every 3-7 days.

FIGS. 15A to 15F are drawings showing anti-GPC-3 mouse CAR T cells suppressed the growth of MC38-mGPC-3 xenografts in vivo.

Figure 15:
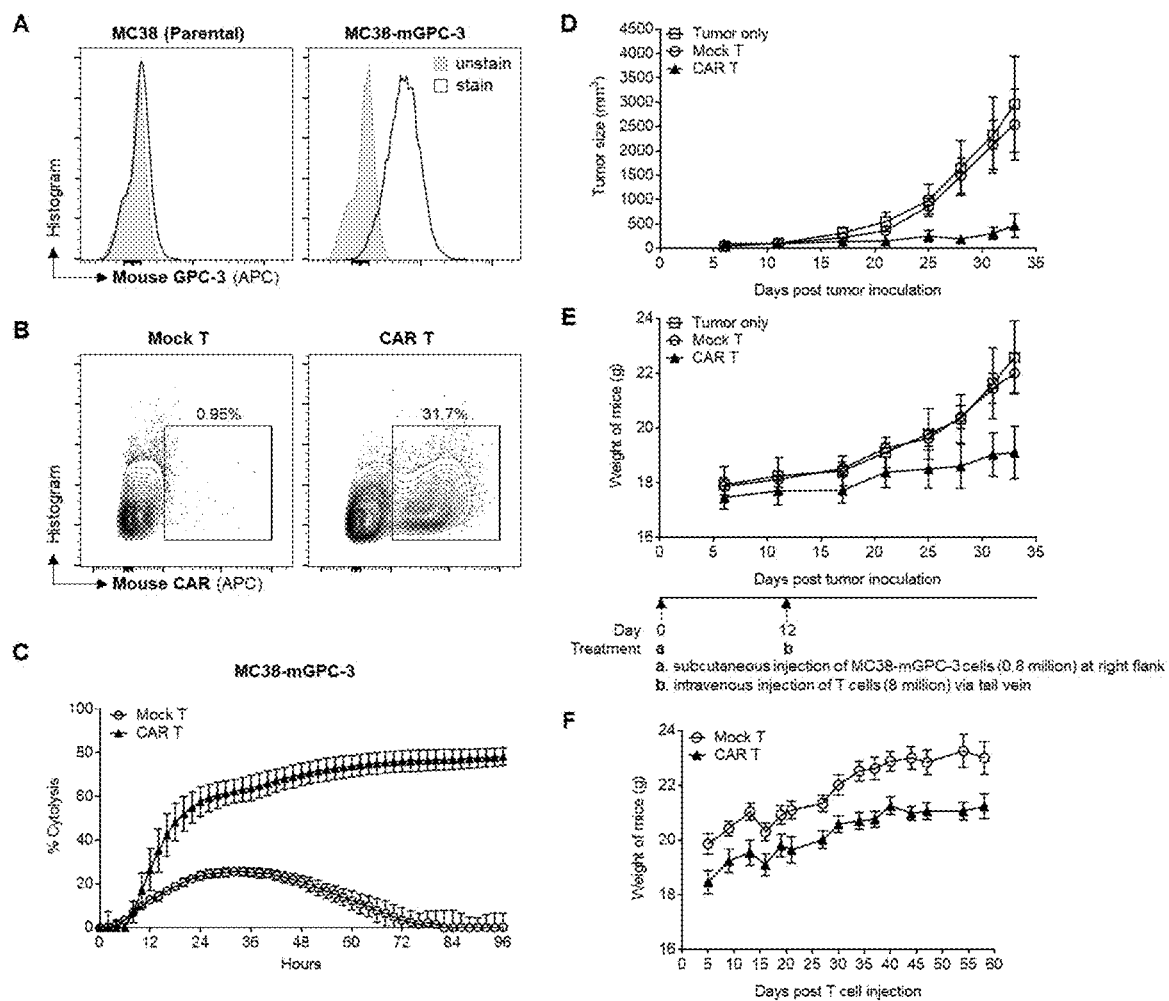

FIG. 15A is a drawing showing MC38 cells stably expressing mouse GPC-3 protein (MC38-mGPC-3) were established by transducing MC38 parental cells with lentivirus-based vectors. Expression of mouse GPC-3 protein was verified by staining with anti-GPC-3 IgG (clone 5C4) followed by flow cytometry analysis.

FIG. 15B is a drawing showing percentage of mouse CAR expression on anti-GPC-3 mouse CAR T cells detected by flow cytometry analysis.

FIG. 15C is a drawing showing percentage of cytolysis of MC38-mGPC-3 cells mediated by anti-GPC-3 mouse CAR T cells (clone 5C4) with time-course measurement using xCelligence impedance assay up to 96 hours.

FIG. 15D and FIG. 15E are drawings showing 0.8 million of MC38-mGPC-3 cells were subcutaneously injected into the right flank of WT C57BL/6 mice. Twelve days later, mice were grouped according to the measurable tumor size (4-5 mice per group). Eight million of anti-GPC-3 mouse CAR T cells (clone 5C4) or Mock T cells were intravenously injected into these mice via tail vein. Tumor size (FIG. 15D) and weight of each mouse (FIG. 15E) were measured and recorded every 3-4 days.

FIG. 15F is a drawing showing anti-GPC-3 mouse CAR T cells did not induce toxicity in the WT mice. WT C57BL/6 mice were intravenously injected with eight million of anti-GPC-3 mouse CAR T cells (clone 5C4) or Mock T cells on Day 0. Body weight of each mouse was measured and recorded every 3-7 days.

SEQUENCES

SEQ ID NO: 1 shows the amino acid sequence of the heavy chain ($V_H$) of monoclonal antibody 5C4. SEQ ID NO: 2 shows the amino acid sequence of the light chain ($V_L$) of monoclonal antibody 5C4.

SEQ ID NO: 3 shows the amino acid sequence of the heavy chain ($V_H$) of monoclonal antibody 4H1. SEQ ID NO: 4 shows the amino acid sequence of the light chain ($V_L$) of monoclonal antibody 4H1.

SEQ ID NO: 5 shows the amino acid sequence of the heavy chain ($V_H$) of monoclonal antibody 1D2. SEQ ID NO: 6 shows the amino acid sequence of the light chain ($V_L$) of monoclonal antibody 1D2.

SEQ ID NO: 7 shows the amino acid sequence of the heavy chain ($V_H$) of monoclonal antibody 1C4. SEQ ID NO: 8 shows the amino acid sequence of the light chain ($V_L$) of monoclonal antibody 1C4.

SEQ ID NO: 9 shows the amino acid sequence of the heavy chain ($V_H$) of monoclonal antibody 2B5. SEQ ID NO: 10 shows the amino acid sequence of the light chain ($V_L$) of monoclonal antibody 2B5.

SEQ ID NO: 11 shows the amino acid sequence of the heavy chain ($V_H$) of monoclonal antibody 1F1. SEQ ID NO: 12 shows the amino acid sequence of the light chain ($V_L$) of monoclonal antibody 1F1.

SEQ ID NO: 13 shows the amino acid sequence of the heavy chain ($V_H$) of monoclonal antibody 1H1. SEQ ID NO: 14 shows the amino acid sequence of the light chain ($V_L$) of monoclonal antibody 1H1.

SEQ ID NO: 15 shows the amino acid sequence of the heavy chain ($V_H$) of monoclonal antibody 4A5. SEQ ID NO: 16 shows the amino acid sequence of the light chain ($V_L$) of monoclonal antibody 4A5.

SEQ ID NO: 17 shows the amino acid sequence of the heavy chain ($V_H$) of monoclonal antibody 1D8. SEQ ID NO: 18 shows the amino acid sequence of the light chain ($V_L$) of monoclonal antibody 1D8.

SEQ ID NO: 19 shows the amino acid sequence of the heavy chain ($V_H$) of monoclonal antibody 1D3. SEQ ID NO: 20 shows the amino acid sequence of the light chain ($V_L$) of monoclonal antibody 1D3.

SEQ ID NO: 21 shows the amino acid sequence of the heavy chain ($V_H$) of monoclonal antibody 2F1. SEQ ID NO: 22 shows the amino acid sequence of the light chain ($V_L$) of monoclonal antibody 2F1.

SEQ ID NO: 23 shows the amino acid sequence of the heavy chain ($V_H$) of monoclonal antibody 3C6. SEQ ID NO: 24 shows the amino acid sequence of the light chain ($V_L$) of monoclonal antibody 3C6.

SEQ ID NO: 25 shows the amino acid sequence of the heavy chain ($V_H$) of monoclonal antibody 3D12. SEQ ID NO: 26 shows the amino acid sequence of the light chain ($V_L$) of monoclonal antibody 3D12.

SEQ ID NO: 27 shows the amino acid sequence of the heavy chain ($V_H$) of monoclonal antibody 3A9. SEQ ID NO: 28 shows the amino acid sequence of the light chain ($V_L$) of monoclonal antibody 3A9.

SEQ ID NO: 29 shows the amino acid sequence of the heavy chain ($V_H$) of monoclonal antibody 1F4. SEQ ID NO: 30 shows the amino acid sequence of the light chain ($V_L$) of monoclonal antibody 1F4.

SEQ ID NO: 31 shows the amino acid sequence of the heavy chain ($V_H$) of monoclonal antibody 1H10. SEQ ID NO: 32 shows the amino acid sequence of the light chain ($V_L$) of monoclonal antibody 1H10.

SEQ ID NO: 33 shows the amino acid sequence of the heavy chain ($V_H$) of monoclonal antibody 3C12. SEQ ID NO: 34 shows the amino acid sequence of the light chain ($V_L$) of monoclonal antibody 3C12.

SEQ ID NO: 35 shows the amino acid sequence of the heavy chain ($V_H$) of monoclonal antibody 4G11. SEQ ID NO: 36 shows the amino acid sequence of the light chain ($V_L$) of monoclonal antibody 4G11.

SEQ ID NO: 37 shows the amino acid sequence of the heavy chain ($V_H$) of monoclonal antibody 4A12. SEQ ID NO: 38 shows the amino acid sequence of the light chain (V$_L$) of monoclonal antibody 4A12.

SEQ ID NO: 39 shows the amino acid sequence of the heavy chain (V$_H$) of monoclonal antibody 1A12. SEQ ID NO: 40 shows the amino acid sequence of the light chain (V$_L$) of monoclonal antibody 1A12.

SEQ ID NO: 41 shows the amino acid sequence of the heavy chain (V$_H$) of monoclonal antibody 3G12. SEQ ID NO: 42 shows the amino acid sequence of the light chain (V$_L$) of monoclonal antibody 3G12.

SEQ ID NO: 43 shows the amino acid sequence of the heavy chain (V$_H$) of monoclonal antibody 4F9. SEQ ID NO: 44 shows the amino acid sequence of the light chain (V$_L$) of monoclonal antibody 4F9.

SEQ ID NO: 45 shows the amino acid sequence of the heavy chain (V$_H$) of monoclonal antibody 4G4. SEQ ID NO: 46 shows the amino acid sequence of the light chain (V$_L$) of monoclonal antibody 4G4.

SEQ ID NO: 47 shows the amino acid sequence of the heavy chain (V$_H$) of monoclonal antibody 1E1. SEQ ID NO: 48 shows the amino acid sequence of the light chain (V$_L$) of monoclonal antibody 1E1.

DETAILED DESCRIPTION

Glypican-3, an Excellent Target for HCC Immunotherapy

Glypican-3 (GPC-3), a member of the heparin sulfate proteoglycan family, is a molecule attached to the cell surface by a glycosyl-phosphatidylinositol (GPI) anchor. In recent years, GPC-3 was found to be a highly specific biomarker for HCC diagnosis and progression, as it is almost exclusively overexpressed on HCC cells but not on normal adult hepatocytes or other normal tissues.

In addition, GPC-3 was also demonstrated to act as a co-receptor for several growth factors, which in turn function to stimulate oncogenic signaling pathways to promote HCC growth.

Hence, as a specific HCC surface marker, GPC-3 is an excellent target for antibody-based immunotherapies for HCC.

We disclose the nucleotide and amino-acid sequences of 24 antibodies, or the antigen-binding portions thereof, that specifically target glypican-3, both in solution and on the surface of cells.

We describe monoclonal antibodies raised against glypican-3 (GPC-3). We refer to these monoclonal antibodies as 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1.

These antibodies are capable of specifically binding glypican-3 (GPC-3), both in solution as well as expressed on the cell surface. The antibodies are also capable of cross-reactivity with glypican-3 (GPC-3) from a number of other species. The antibodies are able to induce antibody dependent cell mediated cytotoxicity. They may be used to construct anti-GPC-3 CAR T cells, which are highly efficient in killing tumour cells.

We disclose the heavy chain variable region (V$_H$) sequences and a light chain variable region (V$_L$) sequences of each of the clones 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1.

We show that Fab fragments, as well as single chain Fv fragments, comprising these variable regions, have the same cross-reactive and strongly neutralizing activities.

Accordingly, we provide for polypeptides comprising these variable regions for the treatment and detection of cancers such as hepatocellular carcinoma.

Anti-Glypican-3 (GPC-3) Antibodies

The Examples describe the generation and production of antibodies generated from, and which have reactivity against, GPC-3 proteins.

We disclose the functional and structural characterization of monoclonal antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1, which are mouse monoclonal antibodies raised against a glypican-3 (GPC-3). We show that these anti-GPC-3 antibodies are capable of killing tumour cells.

We therefore provide broadly for anti-GPC-3 antibodies. The anti-GPC-3 antibodies may comprise the heavy and light chain variable regions of 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 or 1E1.

The anti-GPC-3 antibodies may be used for targeting hepatocellular carcinoma.

The anti-tumour antibody may be capable of binding to GPC-3 polypeptides from a number of different species.

The antibody may be capable of cross-reactivity, i.e., able to bind to more than one polypeptide. For example, the antibody may be capable of binding to two or more variants of a particular polypeptide within a defined group of polypeptides. The two or more variants may therefore comprise cognate or homologous polypeptides from different types of polypeptides in the group. The antibody may be capable of binding to substantially all of the variants of a particular polypeptide within that group.

The disclosure of this document enables the production of these antibodies as well as fragments and variants thereof, including humanised and chimeric antibodies, which have one or more similar or identical properties of anti-GPC-3 antibodies such as 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1.

Such properties may include binding affinity, binding specificity, cross-reactivity, binding avidity, neutralizing activity, etc, as described in further detail below. The specific antibodies and variants thereof described in this document may be produced by a person skilled in the art from the information disclosed in this document, and employing molecular biology techniques which we also describe in detail.

Anti-GPC-3 Antibodies

The polypeptide bound by the anti-GPC-3 antibody may comprise a glypican protein. We specifically disclose anti-GPC-3 antibodies.

Thus, the term "anti-GPC-3 antibody" should be taken to include each of the monoclonal antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1 (as well as their humanised counterparts). Also included are polypeptides comprising the variable regions of any of antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1 and variants, homologues, fragments and derivatives thereof. This term should also be taken to include reference to variants, homologues, fragments and derivatives of the anti-GPC-3 antibodies, as described below, where the context permits.

The anti-GPC-3 antibodies may be generated against glypican-3 from any species, such as human glypican-3.

They may be used to bind to or target a tumour cell, such as a hepatocellular carcinoma cell.

For this reason, the anti-GPC-3 antibodies may also be considered anti-tumour antibodies or anti-liver cancer antibodies.

Monoclonal antibodies and variants thereof including Fab, scFv etc and humanised monoclonal antibodies as well as their properties are disclosed, such as in the Examples. The Examples also describe Fab fragments from the monoclonal antibodies, as well as single chain Fv. Other variants, including humanised versions of each of these antibodies, are also disclosed.

We disclose the sequences of the variable regions of monoclonal antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1. We further disclose variants, homologues, fragments and derivatives of these variable regions. Using this sequence information, a skilled person may produce antibodies comprising these variable regions or their variants, homologues, fragments and derivatives.

We further disclose the sequences of nucleic acid constructs for expressing these monoclonal antibodies. The sequences of these constructs enable the production of monoclonal antibodies which have identical sequences to antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1. We further disclose variants, homologues, fragments and derivatives of antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1.

We disclose the sequences of constructs capable of expressing humanised monoclonal antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1. We describe methods of expressing the antibodies of interest from cells transfected with the constructs, as well as variants, homologues, fragments and derivatives of these humanised constructs.

Using such sequences and the expression methods, the skilled person may readily transfect relevant host cells and cause them to express the whole monoclonal or humanised anti-GPC-3 antibodies, or variants, homologues, fragments and derivatives thereof.

The monoclonal antibodies and variants thereof may comprise the variable region of antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1, as well as further comprising variable regions from other anti-GPC-3 antibodies known in the art. The anti-GPC-3 antibody may comprise the same or different variable regions in a single antibody molecule. They may comprise one variable region, or more than one variable region. Accordingly, we provide the skilled person with the ability to produce any number of antibodies which comprise the same or similar binding reactivity as antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1 or other anti-GPC-3 antibodies.

Such antibodies may comprise the full or substantially complete sequences of an antibody (i.e., heavy chain and light chain), or they may comprise a fragment of a whole antibody (such as Fv, F(ab') and F(ab')$_2$ fragments or single chain antibodies (scFv)). The antibodies may further comprise fusion proteins or synthetic proteins which comprise the antigen-binding site of the antibody, as described in detail below.

It will also be evident that such antibodies may be engineered for desirable properties, such as lowered host reactivity, reduced rejection, etc.

The engineering could include "humanisation", by which term we mean the inclusion of (or substitution with) one or more human residues or sequences in an antibody sequence such as a mouse antibody sequence. "Humanisation" in the context of this document includes "chimeric" antibodies, in which the antibody comprises discrete sections of mouse and human sequences, e.g., where one or both of the variable regions comprise mouse sequences, and the remainder of the antibody molecule (such as the constant region) comprises human sequences. In such chimeric antibodies, the whole of the variable regions of, for example, a mouse or rat antibody may be expressed along with human constant regions. This provides such a chimeric antibody with human effector functions and also reduces immunogenicity (HAMA) caused by the murine Fc region.

Humanisation of 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1 antibodies may be carried out by any suitable means, such as the method described in Hanson B J, Boon A C, Lim A P, Webb A, Ooi E E, Webby R J. *Passive immunoprophylaxis and therapy with humanized monoclonal antibody specific for influenza A H5 hemagglutinin in mice*. Respir Res 17:126, 2006.

Generally, a "chimeric antibody" may refer to an antibody having either a heavy and light chain encoded by a nucleotide sequence derived from a murine immunoglobulin gene and either a heavy and light chain encoded by a nucleotide sequence derived from a human immunoglobulin gene.

"Humanisation" also includes CDR grafted or reshaped antibodies. It thus includes engineering at a more discrete level, e.g., antibodies in which the mouse variable region has been mutated to include human residues to reduce immunogenicity. In such an antibody, only the complimentarity determining regions from the rodent antibody V-regions may be combined with framework regions from human V-regions. Such antibodies should be more human and less immunogenic than chimaeric antibodies.

For the avoidance of doubt, where a specific antibody designation is referred to in this document, this should be taken to include a reference to both the mouse monoclonal antibody (as secreted by a hybridoma), as well as to the humanised version of it, unless the context dictates otherwise. Thus, for example, where antibody 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 or 1E1 is referred to, this includes both the monoclonal antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1 (i.e., as derived from a mouse), as well as a humanised monoclonal antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1.

GPC-3 Binding Polypeptides

We further provide for polypeptides in general having GPC-3 protein binding activity. Such polypeptides include anti-GPC-3 antibodies. The GPC-3-binding polypeptides may comprise one or more of the same or similar properties as the monoclonal antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1. The polypeptides may be referred to for convenience generally as "anti-GPC-3 antibodies".

It is within the skills of a reader to construct binding molecules which may not be (or may not be described as) antibodies or immunoglobulins but which comprise anti-GPC-3 binding activity as described here. Accordingly, and where the context allows the term "anti-GPC-3 antibodies" should be taken to include any molecule so long as it is capable of binding GPC-3. Such molecules may include polypeptides, small molecules, as well as antibodies and immunoglobulins, and may be identified through various means known in the art, for example by screening a suitable library for GPC-3 binding activity.

The GPC-3 binding polypeptides (which include anti-GPC-3 antibodies) may comprise similar or identical properties as the monoclonal antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1. Such similar or identical properties may in particular include binding properties. The GPC-3 binding polypeptides may in general be capable of binding to GPC-3 polypeptides, e.g., GPC-3 from human, GPC-3 from mouse, etc.

GPC-3 Epitopes

The anti-GPC-3 antibodies may have the same or similar binding specificity, binding affinity and/or binding affinity as antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1. The anti-GPC-3 antibodies may specifically bind to an epitope bound by antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1.

Methods are known in the art to determine an epitope that is bound by a particular antibody. Such epitope mapping methods are described for example in Hanson et al., (2006). Respiratory Research, 7:126. Furthermore, a skilled person will be able to generate antibodies and screen them for particular properties.

Accordingly, a skilled person will readily be able to identify anti-GPC-3 antibodies which bind to the same epitope as monoclonal antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1.

Antibody Binding

The anti-GPC-3 antibody may be capable of binding to glypican-3 from humans. It may further be capable of binding to glypican-3 from mouse.

The binding between the anti-GPC-3 antibody and its target may be more or less strong or weak, transient, semi-permanent or permanent. The antibody may bind to its target at an $EC_{50}$ binding affinity of 1 μm or below, such as 100 nm or below.

It may bind with an affinity of 90 nm or below or 80 nm or below. It may bind with an affinity of 70 nm or below, 60 nm or below, 50 nm or below, 40 nm or below, 30 nm or below, 20 nm or below, 10 nm or below, 5 nm or below, 4 nm or below, 3 nm or below, 2 nm or below, 1 nm or below. It may bind with an affinity of 0.5 nm or below, 0.4 nm or below, 0.3 nm or below or 0.2 nm or below.

The antibody may bind to its target with a $K_d$ of micromolar or nanomolar range. It may bind with a $K_d$ of $10^{-7}$ M or less, $10^{-7}$ M or less, $10^{-8}$ M or less, $10^{-9}$ M or less or $10^{-10}$ M or less.

The binding may be measured by any means known in the art, such as ELISA or Surface Plasmon Resonance, both of which are described in detail in the Examples.

Binding of the anti-GPC-3 antibody to the GPC-3 polypeptide may take place within or outside the cell. Such binding may inactivate, inhibit or lower an activity of the GPC-3 polypeptide. The binding may neutralise a GPC-3 activity.

The activity may comprise any biological activity caused by or associated with the GPC-3 polypeptide. The activity may comprise binding to another protein, for example a receptor, a downstream protein or factor. The another protein may comprise GPC-3 itself. The activity may comprise multimerisation activity, such as trimerisation activity or homotrimerisation activity. Binding of anti-GPC-3 antibody to GPC-3 polypeptide may inactivate, inhibit or lower an activity of a receptor, downstream protein or factor. The activity may comprise a biochemical activity or a pathogenic activity.

The binding may inactivate, inhibit or lower an activity of a cell expressing GPC-3. It may inactivate or neutralise or kill the cell expressing GPC-3. The binding between the anti-GPC-3 antibody and the GPC-3 may kill a tumour cell expressing GPC-3.

Antibodies

The terms "antibody" and "immunoglobulin", as used in this document, may be employed interchangeably where the context permits. These term include fragments of proteolytically-cleaved or recombinantly-prepared portions of an antibody molecule that are capable of selectively reacting with or recognising GPC-3 or an epitope thereof, such as an epitope of GPC-3 bound by antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1.

Non limiting examples of such proteolytic and/or recombinant fragments include Fab, F(ab') 2, Fab', Fv fragments, and single chain antibodies (scFv) containing a $V_L$ and $V_H$ domain joined by a peptide linker. These Fvs may be covalently or non-covalently linked to form antibodies having two or more binding sites.

By "ScFv molecules" we mean molecules wherein the $V_H$ and $V_L$ partner domains are linked via a flexible oligopeptide. A general review of the techniques involved in the synthesis of antibody fragments which retain their specific binding sites is to be found in Winter & Milstein (1991) Nature 349, 293-299.

Whole antibodies, and F(ab')$_2$ fragments are "bivalent". By "bivalent" we mean that the said antibodies and F(ab') fragments have two antigen combining sites. In contrast, Fab, Fv, ScFv and dAb fragments are monovalent having only one antigen combining site.

The anti-GPC-3 antibody may comprise a high affinity antibody with an binding affinity of 1 μm or below, such as 100 nm or below, for example, 0.17 nM to 84 nM.

The term "binding affinity" as used in this document refers to the $EC_{50}$ binding affinity an antibody such as an anti-GPC-3 antibody disclosed here. It may be measured using ELISA or Surface Plasmon Resonnance A high $EC_{50}$ binding affinity is desirable as it reflects the affinity of an Fab fragment for an antigen.

The term "affinity" may also be defined in terms of the dissociation rate or off-rate ($k_{off}$) of a an antibody such as an anti-GPC-3 antibody. The lower the off-rate the higher the affinity that an antibody such as an anti-GPC-3 antibody has for an antigen.

The anti-GPC-3 antibody may comprise a peptide per se or form part of a fusion protein.

The anti-GPC-3 antibodies described here include any antibody that comprises GPC-3 binding activity, such as binding ability to GPC-3 or binding to the same epitope bound by antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1.

The anti-GPC-3 antibodies also include the entire or whole antibody, whether mouse, humanised or human, such antibody derivatives and biologically-active fragments. These may include antibody fragments with GPC-3 binding activity that have amino acid substitutions or have sugars or other molecules attached to amino acid functional groups, etc.

The anti-GPC-3 antibody may comprise isolated antibody or purified antibody. It may be obtainable from or produced by any suitable source, whether natural or not, or it may be a synthetic anti-GPC-3 antibody, a semi-synthetic anti-GPC-3 antibody, a derivatised anti-GPC-3 antibody or a recombinant anti-GPC-3 antibody.

Where the anti-GPC-3 antibody is a non-native anti-GPC-3 antibody, it may include at least a portion of which has been prepared by recombinant DNA techniques or an anti-GPC-3 antibody produced by chemical synthesis techniques or combinations thereof.

The term "derivative" as used in this document includes chemical modification of an anti-GPC-3 antibody. Illustrative of such modifications would be replacement of hydrogen by an alkyl, acyl, or amino group, for example. The sequence of the anti-GPC-3 antibody may be the same as that of the naturally occurring form or it may be a variant, homologue, fragment or derivative thereof.

Antibody Variable Regions

The term "variable region", as used in this document, refers to the variable regions, or domains, of the light chains ($V_L$) and heavy chains ($V_L$) which contain the determinants for binding recognition specificity and for the overall affinity of the antibody against GPC-3 (or variant, homologue, fragment or derivative), as the case may be.

The variable domains of each pair of light ($V_L$) and heavy chains ($V_L$) are involved in antigen recognition and form the antigen binding site. The domains of the light and heavy chains have the same general structure and each domain has four framework (FR) regions, whose sequences are relatively conserved, connected by three complementarity determining regions (CDRs). The FR regions maintain the structural integrity of the variable domain. The CDRs are the polypeptide segments within the variable domain that mediate binding of the antigen.

The term "constant region", as used in this document, refers to the domains of the light (CL) and heavy (CH) chain of the antibody (or variant, homologue, fragment or derivative) which provide structural stability and other biological functions such as antibody chain association, secretion, transplacental mobility, and complement binding, but which are not involved with binding a GPC-3 epitope. The amino acid sequence and corresponding exon sequences in the genes of the constant region will be dependent upon the species from which it is derived. However, variations in the amino acid sequence leading to allotypes are relatively limited for particular constant regions within a species. An "allotype" is an antigenic determinant (or epitope) that distinguishes allelic genes.

The variable region of each chain is joined to the constant region by a linking polypeptide sequence. The linkage sequence is coded by a "J" sequence in the light chain gene, and a combination of a "D" sequence and a "J" sequence in the heavy chain gene.

Antibody Variable Region Sequences

Anti-GPC-3 antibodies, according to the methods and compositions described here, may be generated from these variable region sequences by methods known in the art.

For example, the heavy and light chain sequences may be recombined into a constant sequence for a chosen antibody, through recombinant genetic engineering techniques which are known to the skilled person.

Constant region sequences are known in the art, and are available from a number of databases, such as the IMGT/LIGM-DB database (described in Giudicelli et al, 2006, Nucleic Acids Research 34 (Database Issue):D781-D784 and LeFranc et al (1995) *LIGM-DB/IMGT; An Integrated Database of Ig and TcR, Part of the Immunogenetics Database*. Annals of the New York Academy of Sciences 764 (1), 47-47 doi:10.1111/j.1749-6632.1995.tb55805.x) and the IMGT/GENE-DB database (described in Giudicelli et al, 2005, Nucleic Acids Res. 2005 Jan. 1; 33 (Database issue): D256-61). IMGT/LIGM-DB and IMGT/GENE-DB are part of the ImMunoGeneTics Database located at www.ebi-.ac.uk/imgt/.

Methods for combining variable regions with given sequences and constant regions to produce whole antibodies are known in the art and are described in Hanson et al., (2006). *Respiratory Research*, 7:126.

Antibody Single Chain Antibody Sequences

Fragments of whole antibodies such as Fv, F(ab') and F(ab')$_2$ fragments or single chain antibodies (scFv) may be produced by means known in the art.

Using the disclosed sequences and the methods described in the literature, for example, the heavy and light chains of the variable region of antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1, having the sequences shown in this document, may be transgenically fused to a mouse IgG constant region sequence to produce a mouse monoclonal anti-GPC-3 antibody. The variable region of antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1 may be engineered with mouse or human IgG constant regions to produce mouse monoclonal or humanized antibodies capable of binding to GPC-3 polypeptide.

Polypeptide Sequences

It will be understood that polypeptide sequences disclosed here are not limited to the particular sequences set forth in this document, but also include homologous sequences obtained from any source, for example related cellular homologues, homologues from other species and variants or derivatives thereof, provided that they have at least one of the biological activities of an anti-GPC-3 antibody, as the case may be.

This disclosure therefore encompasses variants, homologues or derivatives of the amino acid sequences set forth in this document, as well as variants, homologues or derivatives of the amino acid sequences encoded by the nucleotide sequences disclosed here. Such sequences are generally referred to as a "anti-GPC-3 antibody" sequence.

Biological Activities

In some embodiments, the sequences comprise at least one biological activity of an anti-GPC-3 antibody, as the case may be.

The biological activity may comprise an immunological activity. The anti-GPC-3 antibody may comprise an identical or similar immunological activity as compared to antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1, or its humanised versions. By "immunological activity" we mean the capability of the anti-GPC-3 antibody to induce a specific immune response in appropriate animals or cells on binding with a GPC-3 antigen.

The biological activity may comprise antigen binding activity. The anti-GPC-3 antibody may bind to GPC-3 or an epitope thereof. The anti-GPC-3 antibody may bind to the same epitope bound by antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 or 1E1.

The anti-GPC-3 antibody may bind to the antigen or epitope with the same, a reduced or elevated affinity or avidity. For example, the anti-GPC-3 antibody may bind to the antigen or epitope with at least 10%, such as 20%, such as 30%, 40% 50%, 60%, 70%, 80%, 90% or more, affinity or avidity compared to the cognate antibody or its humanised counterparts, as the case may be.

The activity may include inhibition of glypican-3 activity. Glypican-3 acts as a co-receptor for growth factors, such as BMP, FGF, hedgehogs, which was reported to be associated with HCC development, progression and metastasis.

The anti-GPC-3 antibody may have such inhibition activity that is the same as, reduced from, or elevated from, the cognate antibody. For example, the anti-GPC-3 antibody may be at least 10%, such as 20%, such as 30%, 40% 50%, 60%, 70%, 80%, 90% or more, effective compared to the cognate antibody, e.g., antibody 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 or 1E1 or its humanised counterparts, as the case may be. By this we mean that, say, if the cognate antibody is capable of reducing glypican-3 activity, etc by for example 90%, the anti-GPC-3 antibody may be capable of doing so by below 90%, 85%, 80%, 75%, 70%, 65%, 60%, 55%, 50%, 45%, 40%, 35%, 30%, etc, as compared to an untreated animal or cell.

Other assays that detect antibody events can also be used, instead of, or in addition to, the assays described.

Homologues

The anti-GPC-3 antibody polypeptides disclosed include homologous sequences obtained from any source, for example related viral/bacterial proteins, cellular homologues and synthetic peptides, as well as variants or derivatives thereof. Thus polypeptides also include those encoding homologues of anti-GPC-3 antibody from other species including other animals such as mammals (e.g. mice, rats or rabbits) or humans.

In the context of the present document, a homologous sequence or homologue is taken to include an amino acid sequence which is at least 60, 70, 80 or 90% identical, such as at least 95 or 98% identical at the amino acid level over at least 30, such as 50, 70, 90 or 100 amino acids with a relevant polypeptide sequence, for example as shown in the sequence listing herein. In the context of this document, a homologous sequence is taken to include an amino acid sequence which is at least 15, 20, 25, 30, 40, 50, 60, 70, 80 or 90% identical, such as at least 95 or 98% identical at the amino acid level, such as over at least 15, 25, 35, 50 or 100, such as 200, 300, 400 or 500 amino acids with the sequence of a relevant polypeptide. Although homology can also be considered in terms of similarity (i e amino acid residues having similar chemical properties/functions), in the context of the present document homology may be expressed in terms of sequence identity. The sequence identity may be determined relative to the entirety of the length the relevant sequence, i.e., over the entire length or full length sequence of the relevant gene, for example.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, the default values may be used when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). The GCG Bestfit program may be used.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). The public default values for the GCG package, or in the case of other software, the default matrix, such as BLOSUM62, may be used.

Once the software has produced an optimal alignment, it is possible to calculate % homology, such as % sequence identity. The software typically does this as part of the sequence comparison and generates a numerical result.

Variants and Derivatives

The terms "variant" or "derivative" in relation to the amino acid sequences as described here includes any substitution of, variation of, modification of, replacement of, deletion of or addition of one (or more) amino acids from or to the sequence. The resultant amino acid sequence may retain substantially the same activity as the unmodified sequence, such as having at least the same activity as the anti-GPC-3 antibody polypeptides shown in this document, for example in the sequence listings. Thus, the key feature of the sequences—namely ability to bind to GPC-3 polypeptides or reduction in viral infectivity, homotrimerization, viral absorption, etc, as described elsewhere—may be retained.

Polypeptides having the amino acid sequence shown in the Examples, or fragments or homologues thereof may be modified for use in the methods and compositions described here. Typically, modifications are made that maintain the biological activity of the sequence. Amino acid substitutions may be made, for example from 1, 2 or 3 to 10, 20 or 30 substitutions provided that the modified sequence retains the biological activity of the unmodified sequence Amino acid substitutions may include the use of non-naturally occurring analogues, for example to increase blood plasma half-life of a therapeutically administered polypeptide.

Natural variants of an anti-GPC-3 antibody are likely to comprise conservative amino acid substitutions. Conservative substitutions may be defined, for example according to the Table below Amino acids in the same block in the second column such as those in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Fragments

Polypeptides disclosed here and useful as markers also include fragments of the above mentioned full length polypeptides and variants thereof, including fragments of the sequences set out in the sequence listings.

Polypeptides also include fragments of the full length sequence of any of the anti-GPC-3 antibody polypeptides. Fragments may comprise at least one epitope. Methods of identifying epitopes are well known in the art. Fragments will typically comprise at least 6 amino acids, such as at least 10, 20, 30, 50 or 100 or more amino acids.

Polypeptide fragments of the anti-GPC-3 antibody proteins and allelic and species variants thereof may contain one or more (e.g. 5, 10, 15, or 20) substitutions, deletions or insertions, including conserved substitutions. Where substitutions, deletion and/or insertions occur, for example in different species, such as less than 50%, 40% or 20% of the amino acid residues depicted in the sequence listings are altered.

anti-GPC-3 antibody and their fragments, homologues, variants and derivatives, may be made by recombinant means. However, they may also be made by synthetic means using techniques well known to skilled persons such as solid phase synthesis. The proteins may also be produced as fusion proteins, for example to aid in extraction and purification. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the protein sequence of interest to allow removal of fusion protein sequences. The fusion protein may be such that it will not hinder the function of the protein of interest sequence. Proteins may also be obtained by purification of cell extracts from animal cells.

The anti-GPC-3 antibody polypeptides, variants, homologues, fragments and derivatives disclosed here may be in a substantially isolated form. It will be understood that such polypeptides may be mixed with carriers or diluents which will not interfere with the intended purpose of the protein and still be regarded as substantially isolated. A anti-GPC-3 antibody variant, homologue, fragment or derivative may also be in a substantially purified form, in which case it will generally comprise the protein in a preparation in which more than 90%, e.g. 95%, 98% or 99% of the protein in the preparation is a protein.

The anti-GPC-3 antibody polypeptides, variants, homologues, fragments and derivatives disclosed here may be labelled with a revealing label. The revealing label may be any suitable label which allows the polypeptide, etc to be detected. Suitable labels include radioisotopes, e.g. $^{125}$I, enzymes, antibodies, polynucleotides and linkers such as biotin. Labelled polypeptides may be used in diagnostic procedures such as immunoassays to determine the amount of a polypeptide in a sample. Polypeptides or labelled polypeptides may also be used in serological or cell-mediated immune assays for the detection of immune reactivity to said polypeptides in animals and humans using standard protocols.

The anti-GPC-3 antibody polypeptides, variants, homologues, fragments and derivatives disclosed here, optionally labelled, my also be fixed to a solid phase, for example the surface of an immunoassay well or dipstick. Such labelled and/or immobilised polypeptides may be packaged into kits in a suitable container along with suitable reagents, controls, instructions and the like. Such polypeptides and kits may be used in methods of detection of antibodies to the polypeptides or their allelic or species variants by immunoassay.

Immunoassay methods are well known in the art and will generally comprise: (a) providing a polypeptide comprising an epitope bindable by an antibody against said protein; (b) incubating a biological sample with said polypeptide under conditions which allow for the formation of an antibody-antigen complex; and (c) determining whether antibody-antigen complex comprising said polypeptide is formed.

The anti-GPC-3 antibody polypeptides, variants, homologues, fragments and derivatives disclosed here may be used in in vitro or in vivo cell culture systems to study the role of their corresponding genes and homologues thereof in cell function, including their function in disease. For example, truncated or modified polypeptides may be introduced into a cell to disrupt the normal functions which occur in the cell. The polypeptides may be introduced into the cell by in situ expression of the polypeptide from a recombinant expression vector (see below). The expression vector optionally carries an inducible promoter to control the expression of the polypeptide.

The use of appropriate host cells, such as insect cells or mammalian cells, is expected to provide for such post-translational modifications (e.g. myristolation, glycosylation, truncation, lapidation and tyrosine, serine or threonine phosphorylation) as may be needed to confer optimal biological activity on recombinant expression products. Such cell culture systems in which the anti-GPC-3 antibody polypeptides, variants, homologues, fragments and derivatives disclosed here are expressed may be used in assay systems to identify candidate substances which interfere with or enhance the functions of the polypeptides in the cell.

Polynucleotide Sequences

The variable regions, monoclonal antibody sequences and humanised antibody sequences may comprise polynucleotides. These may comprise DNA or RNA.

They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present document, it is to be understood that the polynucleotides described herein may be modified by any method available in the art. Such modifications may be carried out in order to enhance the in vivo activity or life span of polynucleotides.

Where the polynucleotide is double-stranded, both strands of the duplex, either individually or in combination, are encompassed by the methods and compositions described here. Where the polynucleotide is single-stranded, it is to be understood that the complementary sequence of that polynucleotide is also included.

Variants, Derivatives and Homologues

The terms "variant", "homologue" or "derivative" in relation to a nucleotide sequence described in this document include any substitution of, variation of, modification of, replacement of, deletion of or addition of one (or more) nucleotides from or to the sequence. The resulting sequence may be capable of encoding a polypeptide which has GPC-3 binding activity as described elsewhere in this document.

As indicated above, with respect to sequence identity, a "homologue" has such as at least 5% identity, at least 10% identity, at least 15% identity, at least 20% identity, at least 25% identity, at least 30% identity, at least 35% identity, at least 40% identity, at least 45% identity, at least 50% identity, at least 55% identity, at least 60% identity, at least 65% identity, at least 70% identity, at least 75% identity, at least 80% identity, at least 85% identity, at least 90% identity, or at least 95% identity to a relevant sequence.

There may be at least 95% identity, such as at least 96% identity, such as at least 97% identity, such as at least 98% identity, such as at least 99% identity. Nucleotide homology comparisons may be conducted as described above. A sequence comparison program such as the GCG Wisconsin Bestfit program described above may be used for this purpose. The default scoring matrix has a match value of 10 for each identical nucleotide and −9 for each mismatch. The default gap creation penalty is −50 and the default gap extension penalty is −3 for each nucleotide.

Hybridisation

We further describe nucleotide sequences that are capable of hybridising selectively to any of the sequences presented herein, such as a 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1 variable region, antibody and humanised antibody or any variant, fragment or derivative thereof, or to the complement of any of the above. Nucleotide sequences may be at least 15 nucleotides in length, such as at least 20, 30, 40 or 50 nucleotides in length.

The term "hybridisation" as used herein shall include "the process by which a strand of nucleic acid joins with a complementary strand through base pairing" as well as the process of amplification as carried out in polymerase chain reaction technologies.

Polynucleotides capable of selectively hybridising to the nucleotide sequences presented herein, or to their complement, will be generally at least 70%, such as at least 80 or 90% and such as at least 95% or 98% homologous to the corresponding nucleotide sequences presented herein over a region of at least 20, such as at least 25 or 30, for instance at least 40, 60 or 100 or more contiguous nucleotides.

The term "selectively hybridisable" means that the polynucleotide used as a probe is used under conditions where a target polynucleotide is found to hybridize to the probe at a level significantly above background. The background hybridization may occur because of other polynucleotides present, for example, in the cDNA or genomic DNA library being screened. In this event, background implies a level of signal generated by interaction between the probe and a non-specific DNA member of the library which is less than 10 fold, such as less than 100 fold as intense as the specific interaction observed with the target DNA. The intensity of interaction may be measured, for example, by radiolabelling the probe, e.g. with $^{32}$P.

Hybridisation conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical polynucleotide sequences while an intermediate (or low) stringency hybridisation can be used to identify or detect similar or related polynucleotide sequences.

We disclose nucleotide sequences that can hybridise to a nucleic acid, or a fragment, homologue, variant or derivative thereof, under stringent conditions (e.g. 65° C. and 0.1×SSC {1×SSC=0.15 M NaCl, 0.015 M Na$_3$ Citrate pH 7.0}).

Where a polynucleotide is double-stranded, both strands of the duplex, either individually or in combination, are encompassed by the present disclosure. Where the polynucleotide is single-stranded, it is to be understood that the complementary sequence of that polynucleotide is also disclosed and encompassed.

Polynucleotides which are not 100% homologous to the sequences disclosed here but fall within the disclosure can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of the disclosed sequences under conditions of medium to high stringency.

The polynucleotides described here may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, such as at least 20, for example at least 25, 30 or 40 nucleotides in length, and are also encompassed by the term polynucleotides as used herein. Fragments may be less than 500, 200, 100, 50 or 20 nucleotides in length.

Polynucleotides such as a DNA polynucleotides and probes may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve making a pair of primers (e.g. of about 15 to 30 nucleotides) flanking a region of the sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Glypican-3

Glypican-3 is also known as GPC3 and rat homologue of OCI-5. Its cytogenetic location is Xq26.2 and its genomic coordinates (GRCh38) are X:133,535,744-133,985,615

Members of the glypican family, including GPC3, are heparan sulfate proteoglycans that bind to the exocytoplasmic surface of the plasma membrane through a covalent glycosylphosphatidylinositol (GPI) linkage. The main function of membrane-attached glypicans is to regulate the signaling of WNTs, Hedgehogs, fibroblast growth factors, and bone morphogenetic proteins (Filmus et al., 2008).

To identify the molecular basis for Simpson-Golabi-Behmel syndrome (SGBS; see 312870), also called Simpson dysmorphia syndrome (SDYS), Pilia et al. (1996) adopted a positional cloning approach, using an X/autosome translocation. They used the cell line GM0097, which was deposited in the NIGMS repository in 1974. This cell line originated from a woman diagnosed with Beckwith-Wiedemann syndrome (BWS; 130650) and showed a karyotype with a de novo X; 1 translocation. The karyotype suggested that she was affected by the X-linked SGBS rather than BWS, which is determined by a mutation on 11p. They mapped the breakpoint in an existing contig assembled across Xq26 and found a gene, called GPC3 by them, which was interrupted by this translocation. The gene was interrupted in another female patient with overgrowth and an X; 16 translocation and exhibited deletions in 3 different SGBS families. The 2,130-bp cDNA encodes a deduced protein of 580 amino acids beginning 151 bp from the start of the sequence. GPC3 shares a number of features with the GPC1 gene (600395).

Filmus et al., 1988 isolated rat Gpc3 as a transcript developmentally regulated in intestine, and Filmus et al., 1995 showed that Gpc3, which they called Oci-5, is GPI-linked heparan sulfate proteoglycan.

Pilia et al. (1996) determined that the GPC3 gene contains 8 exons and encompasses approximately 500 kb.

By fluorescence in situ hybridization, Shen et al. (1997) mapped the GPC3 gene to human Xq26 and rat Xq36.

Using DNA microarrays to compare gene expression patterns in normal human placenta with those in other tissues, Sood et al. (2006) found that several genes involved in growth and tissue remodeling were expressed at relatively higher levels in the villus sections of placenta compared with other tissues. These included GPC3, CDKN1C (600856), and IGF2 (147470). The GPC3 and CDKN1C genes are mutated in patients with Simpson-Golabi-Behmel syndrome and Beckwith-Wiedemann syndrome (130650), respectively, both fetal-placental overgrowth syndromes. In contrast, loss of IGF2 is associated with fetal growth restriction in mice. The relatively higher expression of genes that both promote and suppress growth suggested to Sood et al. (2006) tight and local regulation of the pathways that control placental development.

Capurro et al. (2008) found that GPC3 inhibited soluble hedgehog activity in the medium of SHH (600725)-expressing mouse embryonic fibroblasts and IHH (600726)-expressing human embryonic kidney cells. GPC3 interacted with SHH, but not with the SHH receptor Patched (PTCH1; 601309), and it competed with Patched for SHH binding. Furthermore, GPC3 induced SHH endocytosis and degradation. The heparan sulfate chains of GPC3 were not required for its interaction with SHH, but membrane attachment via the GPI anchor was required.

Maurel et al. (2013) observed that expression of both microRNA-1291 (MIR1291; 615487) and GPC3 was upregulated in hepatocellular carcinoma. They found that MIR1291 did not directly bind to GPC3 mRNA, but rather enhanced its stability by binding to and directing degradation of IRE1A (ERN1; 604033), an endoribonuclease that functions in the endoplasmic reticulum unfolded protein response. In the absence of MIR1291, IRE1A bound a canonical site in the 3-prime UTR of GPC3 and cleaved the mRNA, causing its degradation via the unfolded protein response. Unlike most miRNAs, which typically bind complementary sequences in the 3-prime UTRs of target mRNAs, MIR1291 bound a complementary site in the 5-prime UTR of IRE1A to direct its degradation.

In the initial studies of Pilia et al. (1996) in which 6 of the 8 exons of the GPC3 gene were examined, deletions were identified in 3 of 6 patients with SGBS. This suggested that large scale deletions may be responsible for a considerable proportion of cases of Simpson-Golabi-Behmel syndrome. This might not be unexpected given the large region of genomic DNA covered by the GPC3 gene (approximately 500 kb) and the high proportion of deletions found in some other disorders involving large genes, for example, in the dystrophin gene (300377) in patients with Duchenne muscular dystrophy (310200). Lindsay et al. (1997) carried out studies to determine the proportion and type of deletions present in the GPC3 gene in 18 families with SGBS (approximately half of reported cases). Deletions were detected in only 5 families (1 of which had previously been reported). PCR analysis was carried out using primer pairs that amplified fragments from each of the 8 exons of the GPC3 gene and deletions were found in all exons of the gene except exon 3. The results suggested that large scale deletions may be less common in SGBS than was originally thought. One patient, with an exon 4 and 5 deletion, lacked the characteristic facial dysmorphic features. This raised the possibility of involvement of GPC3 gene defects in a wider range of overgrowth disorders.

Simpson-Golabi-Behmel Syndrome, Type 1

Veugelers et al. (2000) identified 1 SGBS patient with a deletion of GPC3 exon 7 (300037.0002). Six SGBS patients showed point mutations in GPC3: 1 frameshift, 3 nonsense, and 1 splice mutation (300037.0004) predicted a loss of function of the glypican-3 protein. One missense mutation, W296R (300037.0003), altered a conserved amino acid found in all glypicans identified to that time. A GPC3 protein that reproduced this mutation was poorly processed and failed to increase the cell surface expression of heparan sulfate, suggesting that this missense mutation is also a loss-of-function mutation.

Sakazume et al. (2007) identified mutations in the GPC3 gene in 7 Japanese boys with SGBS1. One of the boys had an affected younger brother. All the mutations were predicted to result in complete loss of function. Only 1 patient had a large deletion, and there were 5 nonsense and 1 frameshift mutations. There were no apparent genotype/phenotype correlations.

Wilms Tumor, Somatic

White et al. (2002) identified 2 nonconservative single base changes in the GPC3 gene in Wilms tumor (194070) tissue only (300037.0006-300037.0007), implying a possible role of GPC3 in Wilms tumor development. They pointed out that Wilms tumor has been found in a number of patients with Simpson-Golabi-Behmel syndrome (Hughes-Benzie et al., 1996; Xuan et al., 1999).

Capurro et al. (2008) stated that Gpc3-null mouse embryos show significant overgrowth by embryonic day 12.5. They found that embryos between days 10.5 and 13.5 displayed increased hedgehog signaling, as measured by elevated Patched and Gli1 (165220) mRNA levels.

The above text is adapted from the OMIM entry for Glypican-3 (https://www.omim org/entry/300037), contributors Patricia A. Hartz, Cassandra L. Kniffin, Victor A. McKusick, Anne M. Stumpf, Ada Hamosh, George E. Tiller and Michael J. Wright.

GPC-3 Polypeptides and Nucleic Acids

GPC-3 polypeptide homologues, variants, derivatives and fragments may be defined similarly, as set out in the previous paragraphs.

Where the context permits, a reference to GPC-3 polypeptide should be taken to include reference to a GPC-3 polypeptide homologue, variant, derivative or fragment. Similarly, where the context permits, a reference to an GPC-3 nucleic acid should be taken to include reference to an GPC-3 nucleic acid homologue, variant, derivative or fragment.

An example of a glypican-3 nucleic acid is the sequence having GenBank Accession Number NM_004484.4.

An example of a glypican-3 polypeptide is the sequence having GenBank Accession Number NP_004475.1.

Anti-GPC-3 Antibody Production

The anti-GPC-3 antibody can be produced by recombinant DNA methods or synthetic peptide chemical methods that are well known to those of ordinary skill in the art.

By way of example, the anti-GPC-3 antibody may be synthesized by techniques well known in the art, as exemplified by "Solid Phase Peptide Synthesis: A Practical Approach" E. Atherton and R. C. Sheppard, IRL Press, Oxford England. Similarly, multiple fragments can be synthesized which are subsequently linked together to form larger fragments. These synthetic peptide fragments can also be made with amino acid substitutions at specific locations in order to test for activity in vitro and in vivo.

The anti-GPC-3 antibody can be synthesized in a standard microchemical facility and purity checked with HPLC and mass spectrophotometry. Methods of peptide synthesis, HPLC purification and mass spectrophotometry are commonly known to those skilled in these arts.

The anti-GPC-3 antibody may also be expressed under in vitro and in vivo conditions in a transformed host cell into which has been incorporated the DNA sequences described here (such as variable sequences) or allelic variations thereof and which can be used in the prevention and/or treatment of cancers such as hepatocellular carcinoma.

The term "vector" includes expression vectors and transformation vectors. The term "expression vector" means a construct capable of in vivo or in vitro expression. The term "transformation vector" means a construct capable of being transferred from one species to another.

Vectors which may be used for expression include recombinant viral vectors, in particular recombinant retroviral vectors (RRV) such as lentiviral vectors, adenoviral vectors including a combination of retroviral vectors.

The term 'recombinant retroviral vector" (RRV) refers to a vector with sufficient retroviral genetic information to allow packaging of an RNA genome, in the presence of packaging components, into a viral particle capable of infecting a target cell. Infection of the target cell includes reverse transcription and integration into the target cell genome. The RRV carries non-viral coding sequences which are to be delivered by the vector to the target cell. An RRV is incapable of independent replication to produce infectious retroviral particles within the final target cell. Usually the RRV lacks a functional gag pol and/or env gene and/or other genes essential for replication. Vectors which may be used include recombinant pox viral vectors such as fowl pox virus (FPV), entomopox virus, vaccinia virus such as NYVAC, canarypox virus, MVA or other non-replicating viral vector systems such as those described for example in WO9530018.

Pox viruses may be engineered for recombinant gene expression and for the use as recombinant live vaccines in a dual immunotherapeutic approach. The principal rationale for using live attenuated viruses, such as viruses, as delivery vehicles and/or vector based vaccine candidates, stems from their ability to elicit cell mediated immune responses. The viral vectors, as outlined above, are capable of being employed as delivery vehicles and as vector based vaccine candidates because of the immunogenicity of their constitutive proteins, which act as adjuvants to enhance the immune response, thus rendering a nucleotide sequence of interest (NOI) such as a nucleotide sequence encoding an anti-GPC-3 antibody more immunogenic.

The pox virus vaccination strategies have used recombinant techniques to introduce NOIs into the genome of the pox virus. If the NOI is integrated at a site in the viral DNA which is non-essential for the life cycle of the virus, it is possible for the newly produced recombinant pox virus to be infectious, that is to say to infect foreign cells and thus to express the integrated NOI. The recombinant pox virus prepared in this way can be used as live vaccines for the prophylaxis and/or treatment of disease.

Other requirements for pox viral vector delivery systems include good immunogenicity and safety. MVA is a replication-impaired vaccinia strain with a good safety record. In most cell types and normal human tissue, MVA does not replicate. Limited replication of MVA is observed in a few transformed cell types such as BHK21 cells. Carroll et al (1997 Vaccine15: 387-394) have shown that the recombinant MVA is equally as good as conventional recombinant vaccinia vectors at generating a protective CD8+T cell response and is an efficacious alternative to the more commonly used replication competent vaccinia virus. The vaccinia virus strains derived from MVA, or independently developed strains having the features of MVA which make MVA particularly suitable for use in a vaccine, are also suitable for use as a delivery vehicle.

The nucleotide sequence of interest, and of which expression is desired, may operably linked to a transcription unit. The term "transcription unit" as described herein are regions of nucleic acid containing coding sequences and the signals for achieving expression of those coding sequences independently of any other coding sequences. Thus, each transcription unit generally comprises at least a promoter, an optional enhancer and a polyadenylation signal. The term "promoter" is used in the normal sense of the art, e.g. an RNA polymerase binding site. The promoter may contain an enhancer element. The term "enhancer" includes a DNA sequence which binds to other protein components of the transcription initiation complex and thus facilitates the initiation of transcription directed by its associated promoter. The term "cell" includes any suitable organism. The cell may comprise a mammalian cell, such as a human cell.

The term "transformed cell" means a cell having a modified genetic structure. For example, as described here, a cell has a modified genetic structure when a vector such as an expression vector has been introduced into the cell. The term "organism" includes any suitable organism. The organism may comprise a mammal such as a human.

Here the term "transgenic organism" means an organism comprising a modified genetic structure. For example, the organism may have a modified genetic structure if a vector such as an expression vector has been introduced into the organism.

Antibody Expression

We further describe a method comprising transforming a host cell with a or the nucleotide sequences described in this document, such as 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1 variable regions, antibody sequences or humanized antibody sequences.

We also provide a method comprising culturing a transformed host cell-which cell has been transformed with a or the such nucleotide sequences under conditions suitable for the expression of the anti-GPC-3 antibody encoded by said nucleotide sequences.

We further provide a method comprising culturing a transformed host cell-which cell has been transformed with a or the such nucleotide sequences under conditions suitable for the expression of the anti-GPC-3 antibody encoded by said nucleotide sequences; and then recovering said anti-GPC-3 antibody from the transformed host cell culture.

Thus, anti-GPC-3 antibody encoding nucleotide sequences, fusion proteins or functional equivalents thereof, may be used to generate recombinant DNA molecules that direct the expression thereof in appropriate host cells.

By way of example, anti-GPC-3 antibody may be produced in recombinant E. coli, yeast or mammalian expression systems, and purified with column chromatography.

In certain circumstances there are advantages of using antibody fragments, rather than whole antibodies. The smaller size of the fragments allows for rapid clearance, and may lead to improved neutralization of viral activity, infection, progression, etc. Fab, Fv, ScFv antibody fragments can all be expressed in and secreted from E. coli, thus allowing the production of large amounts of the such fragments.

The nucleotide sequences encoding the anti-GPC-3 antibody may be operably linked to a promoter sequence capable of directing expression of the anti-GPC-3 antibody encoding nucleotide sequences in a suitable host cell. When inserted into the host cell, the transformed host cell may be cultured under suitable conditions until sufficient levels of the anti-GPC-3 antibody are achieved after which the cells may be lysed and the anti-GPC-3 antibody is isolated.

Host cells transformed with the anti-GPC-3 antibody encoding nucleotide sequences may be cultured under conditions suitable for the expression and recovery of the anti-GPC-3 antibody from cell culture. The protein produced by a recombinant cell may be secreted or may be contained intracellularly depending on the sequence and/or the vector used. As will be understood by those of skill in the art, expression vectors containing the anti-GPC-3 antibody encoding nucleotide sequences can be designed with signal sequences which direct secretion of the anti-GPC-3 antibody encoding nucleotide sequences through a particular prokaryotic or eukaryotic cell membrane. Other recombinant constructions may join the anti-GPC-3 antibody encoding nucleotide sequence to a nucleotide sequence encoding a polypeptide domain which will facilitate purification of soluble proteins (Kroll D J et al (1993) DNA Cell Biol 12:441-5 3', see also the discussion below on vectors containing fusion proteins).

The anti-GPC-3 antibody may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals (Porath J (1992) Protein Expr Purif 3-26328 1), protein A domains that allow purification on immobilized immunoglobulin, and the domain utilized in the FLAGS extension/affinity purification system (Immunex Corp, Seattle, WA). The inclusion of a cleavable linker sequence such as Factor XA or enterokinase (Invitrogen, San Diego, CA) between the purification domain and the anti-GPC-3 antibody is useful to facilitate purification.

The nucleotide sequences described here may be engineered in order to alter a the anti-GPC-3 antibody encoding sequences for a variety of reasons, including but not limited to alterations which modify the cloning, processing and/or expression of the gene product. For example, mutations may be introduced using techniques which are well known in the art, e.g., site-directed mutagenesis to insert new restriction sites, to alter glycosylation patterns or to change codon preference.

In another embodiment, a or the natural, modified or recombinant anti-GPC-3 antibody encoding nucleotide sequences may be ligated to a heterologous sequence to encode a fusion protein. By way of example, fusion proteins comprising the anti-GPC-3 antibody or an enzymatically active fragment or derivative thereof linked to an affinity tag such as glutathione-S-transferase (GST), biotin, His6, ac-myc tag (see Emrich et al 1993 BiocemBiophys Res Commun 197(1): 21220), hemagglutinin (HA) (as described in Wilson et al (1984 Cell 37 767) or a FLAG epitope (Ford et al 1991 Protein Expr Purif April; 2 (2):95-107).

The fused recombinant protein may comprise an antigenic coprotein such as GST, beta-galactosidase or the lipoprotein D from Haemophillls influenzae which are relatively large co-proteins, which solubilise and facilitate production and purification thereof. Alternatively, the fused protein may comprise a carrier protein such as bovine serum albumin (BSA) or keyhole limpet haemocyanin (KLH). In certain embodiments, the marker sequence may comprise a hexa-histidine peptide, as provided in the pQE vector (Qiagen Inc) and described in Gentz et al (1989 PNAS 86: 821-824). Such fusion proteins are readily expressable in yeast culture (as described in Mitchell et al 1993 Yeast 5:715-723) and are easily purified by affinity chromatography. A fusion protein may also be engineered to contain a cleavage site located between the nucleotide sequence encoding the anti-GPC-3 antibody and the heterologous protein sequence, so that the anti-GPC-3 antibody may be cleaved and purified away from the heterologous moiety. In another embodiment, an assay for the target protein may be conducted using the entire, bound fusion protein. Alternatively, the co-protein may act as an adjuvant in the sense of providing a generalised stimulation of the immune system. The co-protein may be attached to either the amino or carboxy terminus of the first protein.

Although the presence/absence of marker gene expression suggests that the nucleotide sequence for anti-GPC-3 antibody is also present, its presence and expression should be confirmed. For example, if the anti-GPC-3 antibody encoding nucleotide sequence is inserted within a marker gene sequence, recombinant cells containing the anti-GPC-3 antibody coding regions may be identified by the absence of the marker gene function. Alternatively, a marker gene may be placed in tandem with a anti-GPC-3 antibody encoding nucleotide sequence under the control of a single promoter. Expression of the marker gene in response to induction or selection usually indicates expression of the anti-GPC-3 antibody as well.

Additional methods to quantitate the expression of a particular molecule include radiolabeling (Melby P C et al 1993 J Immunol Methods 159:235-44) or biotinylating (Duplaa C et al 1993 Anal Biochem 229-36) nucleotides, co amplification of a control nucleic acid. and standard curves onto which the experimental results are interpolated.

Quantitation of multiple samples may be speeded up by running the assay in an ELISA format where the anti-GPC-3 antibody of interest is presented in various dilutions and a spectrophotometric or calorimetric response gives rapid quantitation.

Altered anti-GPC-3 antibody nucleotide sequences which may be made or used include deletions, insertions or substitutions of different nucleotide residues resulting in a nucleotide sequence that encodes the same or a functionally equivalent anti-GPC-3 antibody. By way of example, the expressed anti-GPC-3 antibody may also have deletions, insertions or substitutions of amino acid residues which produce a silent change and result in a functionally equivalent anti-GPC-3 antibody. Deliberate amino acid substitutions may be made on the basis of similarity in polarity, charge, solubility, hydrophobicity, hydrophilicity, and/or the amphipathic nature of the residues as long as the binding affinity of the anti-GPC-3 antibody is retained. For example, negatively charged amino acids include aspartic acid and glutamic acid: positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Bi-Specific Antibodies

We disclose bi-specific antibodies or antigen-binding fragments capable of binding both GPC-3 as well as another antigen.

The second antigen may comprise a T-cell surface antigen. An example of a T-cell surface antigen is a CD protein, such as CD3 (GenBank Accession Number: NM_000733.4).

We specifically disclose an anti-GPC-3 bi-specific T cell-engaging antibody, which is capable of specifically recognising and binding to both GPC-3 and human CD3 molecules on the cell surface.

Such a bi-specific antibody may be constructed by replacing the Fab region of one arm of the antibody with sequences capable of binding to a T-cell surface antigen such as CD3. Such T-cell surface antigen binding sequences may for example comprise $V_H$ and $V_L$ regions of a known antibody against the T-cell surface antigen. They may be provided in the form of an anti-CD3 scFv fragment, for example.

A detailed protocol for constructing a bi-specific antibody capable of binding CD3 is set out in the Examples.

A bi-specific antibody or antigen-binding fragment may be capable of activating naïve T-cells, inducing cytokine release (such as of interferon-γ and IL-2) and/or of inducing cell death of GPC-3 expressing cells.

Chimeric Antigen Receptors (CARS)

Chimeric antigen receptors (CARs), also known as chimeric T cell receptors, artificial T cell receptors and chimeric immunoreceptors, are engineered receptors which graft an arbitrary specificity onto an immune effector cell.

In a classical CAR, the specificity of a monoclonal antibody is grafted on to a T cell. CAR-encoding nucleic acids may be transferred to T cells using, for example, retroviral vectors. In this way, a large number of cancer-specific T cells can be generated for adoptive cell transfer. Phase I clinical studies of this approach show efficacy.

The target-antigen binding domain of a CAR is commonly fused via a spacer and transmembrane domain to a signaling endodomain. When the CAR binds the target-antigen, this results in the transmission of an activating signal to the T-cell it is expressed on.

We disclose a CAR which comprises a glypican-3 binding domain which is based on any of the antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 or 1E1.

The CAR may comprise a glypican-3-binding domain which comprises
(a) a heavy chain variable region ($V_H$) having complementarity determining regions (CDRs) of any of the above antibodies, as set out in this document;
(b) a light chain variable region ($V_L$) having CDRs of any of the above antibodies, as set out in this document.

It may be possible to introduce one or more mutations (substitutions, additions or deletions) into the or each CDR without negatively affecting glypican-3-binding activity. Each CDR may, for example, have one, two or three amino acid mutations.

The CAR may comprise one of the following $V_H$ sequences SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47.

The CAR may comprise one of the following $V_L$ sequences SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48.

The CAR may comprise a variant of any of these sequences having at least 80, 85, 90, 95, 98 or 99% sequence identity, provided that the variant sequence retain the capacity to bind glypican-3 (when in conjunction with a complementary $V_L$ or $V_H$ domain, if appropriate).

The percentage identity between two polypeptide sequences may be readily determined by programs such as BLAST which is freely available at http://blast.ncbi.nlm.nih.gov.

Transmembrane Domain

The CAR may also comprise a transmembrane domain which spans the membrane. It may comprise a hydrophobic alpha helix. The transmembrane domain may be derived from CD28, which gives good receptor stability.

Intracellular T Cell Signaling Domain (ENDODOMAIN)

The endodomain is the signal-transmission portion of the CAR. After antigen recognition, receptors cluster and a signal is transmitted to the cell. The most commonly used endodomain component is that of CD3-zeta which contains 3 ITAMs. This transmits an activation signal to the T cell after antigen is bound. CD3-zeta may not provide a fully competent activation signal and additional co-stimulatory signaling may be needed. For example, chimeric CD28 and OX40 can be used with CD3-Zeta to transmit a proliferative/survival signal, or all three can be used together.

The endodomain of the CAR may comprise the CD28 endodomain and OX40 and CD3-Zeta endodomain.

A variant sequence may have at least 80%, 85%, 90%, 95%, 98% or 99% sequence identity to such an endodomain, provided that the sequence provides an effective transmembrane domain/intracellular T cell signaling domain.

Signal Peptide

The CAR may comprise a signal peptide so that when the CAR is expressed inside a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The CAR may have the general formula:

> Signal peptide–glypican-3-binding domain–spacer domain–transmembrane domain–intracellular T cell signaling domain.

Spacer

The CAR may comprise a spacer sequence to connect the glypican-3-binding domain with the transmembrane domain and spatially separate the glypican-3-binding domain from the endodomain. A flexible spacer allows to the glypican-3-binding domain to orient in different directions to enable glypican-3 binding.

The spacer sequence may, for example, comprise an IgG1 Fc region, an IgG1 hinge or a CD8 stalk, or a combination thereof. The spacer may alternatively comprise an alternative sequence which has similar length and/or domain spacing properties as an IgG1 Fc region, an IgG1 hinge or a CD8 stalk.

A human IgG1 spacer may be altered to remove Fc binding motifs.

Examples of amino acid sequences for these spacers are given below: hinge-CH2CH3 of human IgG1, human CD8 stalk, human IgG1 hinge, IgG1 Hinge-Fc and IgG1 Hinge-Fc modified to remove Fc receptor recognition motifs.

Diagnostic Kits

We also provide diagnostic kits for detecting cancer, including hepatocellular carcinoma in an individual, or susceptibility to such in an individual.

The diagnostic kit may comprise means for detecting expression, amount or activity of GPC-3 in the individual, by any means as described in this document. The diagnostic kit may therefore comprise any one or more of the following: an anti-GPC-3 antibody, an antibody capable of binding to the same epitope as monoclonal antibody 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 or 1E1, monoclonal antibody 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 or 1E1, Fab from 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 or 1E1, scFv from 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 or 1E1, an antibody comprising a variable region of antibody 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 or 1E1, or a humanised monoclonal antibody 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 or 1E1, etc The diagnostic kit may comprise instructions for use, or other indicia. The diagnostic kit may further comprise means for treatment or prophylaxis of cancer (for example hepatocellular carcinoma), such as any of the compositions described in this document, or any means known in the art for treating cancer (such as hepatocellular carcinoma). In particular, the diagnostic kit may comprise an anti-GPC-3 antibody as described, for example obtained by screening.

Hepatocellular Carcinoma/Liver Cancer

The anti-GPC-3 antibodies and binding agents disclosed in this document may be used for the treatment, prevention or alleviation of a cancer such as liver cancer.

Carcinoma of the liver (hepatocellular carcinoma, HCC) is the fifth most common malignancy worldwide and third highest cause of global cancer mortality (Ferley J, Bray F. Pisani P, Parkin D M. GLOBOCAN 2002: Cancer Incidence, Mortality and Prevalence Worldwide. IARC CancerBase No 5 version 20. IARCPress, Lyon, France; 2004).

Hepatocellular carcinoma (HCC) has replaced stomach cancer as the $3^{rd}$ highest ranking cancer among Singaporean males, accounting for 8.1% of all cancers diagnosed in 1998-2002 (Seow A, K. W., Chia K S, Shi L M, Lee H P, Shanmugaratnam K (2004). "Trends in Cancer Incidence in Singapore 1968-2002." *Singapore Cancer Registry* (Report no. 6)). In Asia, where about 250,000 new cases per year are reported in China alone, HCC is endemic. Worldwide, it is the leading cause of cancer mortality (Bosch, F. X., J. Ribes, et al. (2005). "Epidemiology of hepatocellular carcinoma." *Clin Liver Dis* 9(2): 191-211, v.). Even in countries like the USA and Europe where the prevalence of HCC is lower, the incidence of HCC is on the rise (El-Serag, H. B. and A. C.

Mason (1999). "Rising incidence of hepatocellular carcinoma in the United States." *N Engl J Med* 340(10): 745-50).

More than 90% of HCCs are diagnosed at an advanced stage and are often associated with liver cirrhosis. HCCs typically exhibit highly aggressive clinical behaviour with the majority of patients dying within 12 months of diagnosis (El-Serag H B. Hepatocellular carcinoma: an epidemiologic view. J Clin Gastroenterol 2002; 35 (5 Suppl 2):572-8).

Often, patients present at such advanced disease stages that surgery is not an option; in cases where surgical resections are performed the two-year recurrence rate is still as high as 50% (Nagasue N, Kohno H, Chang Y C, Taniura H, Yamanoi A, Uchida M, et al. Liver resection for hepatocellular carcinoma. Results of 229 consecutive patients during 11 years. Ann Surg 1993; 217:375-84; Yamamoto J, Kosuge T, Takayama T, Shimada K, Yamasaki S, Ozaki H, et al. Recurrence of hepatocellular carcinoma after surgery. Br J Surg 1996; 83:1219-22).

HCC is a relatively chemotherapy refractory cancer. There is no single agent or multi-agent chemotherapy that is particularly effective. Doxorubicin is the most commonly used chemotherapy agent in metastatic HCC with response rates of less than 20% (Johnson, P. J., R. Williams, et al. (1978). "Induction of remission in hepatocellular carcinoma with doxorubicin." *Lancet* 1 (8072): 1006-9) and statistically insignificant survival advantage. More recent results of a trial using 3-drug combination chemotherapy and interferon showed response rates of 20.9% and median survival of 8.67 months (Yeo, W., T. S. Mok, et al. (2005). "A randomized phase III study of doxorubicin versus cisplatin/interferon alpha-2b/doxorubicin/fluorouracil (PIAF) combination chemotherapy for unresectable hepatocellular carcinoma." *J Natl Cancer Inst* 97(20): 1532-8). This regimen did not show better survival compared to doxorubicin alone and was associated with more toxicities.

Recent results from randomized clinical trials have shown that standard chemotherapeutic regimens are minimally effective in prolonging HCC patient survival (Yeo W, Mok T S, Zee B, Leung T W, Lai P B, Lau W Y, et al. A randomized phase III study of doxorubicin versus cisplatin/interferon alpha-2b/doxorubicin/fluorouracil (PIAF) combination chemotherapy for unresectable hepatocellular carcinoma. J Natl Cancer Inst 2005; 97:1532-38).

Besides tumor recurrence and metastasis, peritoneal ascites is another significant cause of morbidity in advanced stage HCC patients, often arising as a result of compromised liver function, portal vein blockage, and increased endothelial cell permeability.

Prophylactic and Therapeutic Methods

The monoclonal antibodies 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1 may be used for treatment of disease in humans or other animals.

We show in the Examples that such anti-GPC-3 antibodies have anti-tumour activity. Specifically, the Examples indicate that the anti-GPC-3 antibodies may be used for treating and preventing hepatocellular carcinoma.

We disclose methods of treating cancers, including hepatocellular carcinoma. Methods of preventing cancer such as hepatocellular carcinoma (i.e., prophylaxis) also suitably employ the same or similar approaches.

Accordingly, we provide for the use of anti-GPC-3 antibodies in the treatment or prevention of a proliferative disease. The proliferative disease may comprise cancer. The anti-GPC-3 antibodies may be used as drugs or therapies to treat cancer such as hepatocellular carcinoma. They may be used to prevent such infection or progress of the disease.

In general terms, our methods involve manipulation of cells, by modulating (such as down-regulating) the expression, amount or activity of GPC-3. The treatment may comprise generally contacting a tumour cell, or a cell suspected of being a tumour cell, with an anti-GPC-3 antibody. The methods may involve exposing a patient to an anti-GPC-3 antibody or variant thereof as described here.

It may or in addition be exposed to an anti-cancer agent such as an antibody or other molecule known to have effect in preventing or treating cancer such as liver cancer. Where this is so, the cell may be exposed to both the antibody and the agent together, or individually in sequence. The exposure may be repeated a number of times. Any combination of anti-GPC-3 antibody and an other agent antibody in whatever amount or relative amount, in whatever timing of exposure, may be used.

We therefore provide for the use of combinations of anti-GPC-3 antibodies and anti-cancer agents, as described above, in the treatment of a cancer such as liver cancer.

The cell may be an individual cell, or it may be in a cell mass. The cell may be inside the body of an organism. The organism may be one which is known to be suffering from cancer, or it could be one in which cancer is suspected, or it could be one which is susceptible to cancer. The treatment may comprise administering the antibody or antibodies to the organism. As above, a single antibody may be administered, or a combination of anti-GPC-3 antibody and an anti-cancer agent may be administered. The administration may be simultaneous or sequential, as described above. Thus, the treatment may comprise administering an anti-GPC-3 antibody simultaneously or sequentially with an anti-cancer agent to the individual.

For this purpose, a number of criteria may be designated, which reflect the progress of treatment or prophylaxis or the well-being of the patient. Useful criteria in the case of cancer may include TNM staging, the Okuda system, CLIP score, BCLC staging as known the art. For example the measurement of tumor size and severity of cirrhosis, for example as measured by the amount of ascites, serum albumin, and bilirubin levels may be used in the assessment of treatment.

Treatment of liver cancer is described in detail in Liu et al (2015), *Cold Spring Harb Perspect Med.* 2015 September; 5(9).

Thus, as an example, a treated individual may show a decrease in such a symptom as measured by an appropriate assay or test. A treated individual may for example show a 1%, 2%, 3%, 4%, 5%, 6%, 7%, 8%, 9%, 10%, 15%, 20%, 25%, 30%, 40%, 50%, 60%, 70%, 80%, 90%, 100% or more decrease in one or more symptoms, compared to an individual who has not been treated.

For example, a patient disease may be defined as being "treated" if a condition associated with the disease is significantly inhibited (i.e., by 50% or more) relative to controls. The inhibition may be by at least 75% relative to controls, such as by 90%, by 95% or 100% relative to controls. By the term "treatment" we mean to also include prophylaxis or alleviation of cancer such as liver cancer.

The antibody approach to therapy involving use of anti-GPC-3 antibodies may be combined with other approaches for therapy of such disorders including conventional drug based approaches.

Treatment

The mainstay of treatment is supportive therapy. The patient is encouraged to keep up oral intake, especially of oral fluids. If the patient is unable to maintain oral intake, supplementation with intravenous fluids may be necessary to prevent dehydration and significant hemoconcentration. A platelet transfusion is indicated if the platelet level drops significantly.

Pharmaceutical Compositions

As disclosed herein, anti-GPC-3 antibodies may be used to treat or prevent cancer such as liver cancer.

Anti-GPC-3 antibodies can be administered in a variety of ways including enteral, parenteral and topical routes of administration. For example, suitable modes of administration include oral, subcutaneous, transdermal, transmucosal, iontophoretic, intravenous, intramuscular, intraperitoneal, intranasal, subdural, rectal, and the like.

In accordance with other embodiments, there is provided a composition comprising an anti-GPC-3 antibody, together with a pharmaceutically acceptable carrier or excipient for the treatment or prevention of cancer such as liver cancer.

Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-p-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference.

Pharmaceutical compositions containing an anti-GPC-3 antibody may be in any form suitable for the intended method of administration, including, for example, a solution, a suspension, or an emulsion. Liquid carriers are typically used in preparing solutions, suspensions, and emulsions. Liquid carriers contemplated for use in the practice include, for example, water, saline, pharmaceutically acceptable organic solvent (s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols.

Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions may also be in the form of microparticles, microcapsules, liposomal encapsulates, and the like, as well as combinations of any two or more thereof.

The anti-GPC-3 antibody may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrastemal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e. g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

In accordance with yet other embodiments, we provide methods for inhibiting any activity of GPC-3, in a human or animal subject, the method comprising administering to a subject an amount of an anti-GPC-3 antibody (or composition comprising such compound) effective to inhibit the relevant activity in the subject. Other embodiments provide methods for treating cancer such as liver cancer, in a human or animal subject, comprising administering to the cell or to the human or animal subject an amount of a compound or composition as described here effective to inhibit a GPC-3 activity in the cell or subject. The subject may be a human or non-human animal subject. Inhibition of protein activity includes detectable suppression of the relevant protein activity either as compared to a control or as compared to expected protein activity.

Effective amounts of the anti-GPC-3 antibody generally include any amount sufficient to detectably inhibit the relevant protein activity by any of the assays described herein, by other assays known to those having ordinary skill in the art or by detecting an alleviation of symptoms in a subject afflicted with cancer such as liver cancer.

Successful treatment of a subject in accordance may result in the inducement of a reduction or alleviation of symptoms in a subject afflicted with a medical or biological disorder to, for example, halt the further progression of the disorder, or the prevention of the disorder. Thus, for example, treatment cancer such as liver cancer can result in a reduction in symptoms as described above.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

A therapeutically effective dose will generally be from about 10 µg/kg/day to 100 mg/kg/day, for example from about 25 µg/kg/day to about 20 mg/kg/day or from about 50 µg/kg/day to about 2 mg/kg/day of an anti-GPC-3 antibody, which may be administered in one or multiple doses.

The anti-GPC-3 antibody can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound, stabilizers, preservatives, excipients, and the like. Lipids which may be used include the phospholipids and phosphatidyl cholines (lecithins), both natural and synthetic. Methods to form liposomes are known in the art. See, for example, Prescott, Ed., Methods in Cell Biology, Volume XIV, Academic Press, New York, N. W., p. 33 et seq (1976).

While the anti-GPC-3 antibody can be administered as the sole active pharmaceutical agent, they can also be used in combination with one or more other agents used in the treatment of disorders. Representative agents useful in combination with the anti-GPC-3 antibody for the treatment of cancer such as liver cancer include, for example, Sorafenib, Lenvatinib and Regorafenib.

When additional active agents are used in combination with the anti-GPC-3 antibody, the additional active agents may generally be employed in therapeutic amounts as indicated in the PHYSICIANS'DESK REFERENCE (PDR) 53rd Edition (1999), which is incorporated herein by reference, or such therapeutically useful amounts as would be known to one of ordinary skill in the art.

The anti-GPC-3 antibody and the other therapeutically active agents can be administered at the recommended maximum clinical dosage or at lower doses. Dosage levels of the active anti-GPC-3 antibody in the compositions may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

Bioavailability The compounds disclosed here (and combinations) are in some embodiments orally bioavailable. Oral bioavailablity refers to the proportion of an orally administered drug that reaches the systemic circulation. The factors that determine oral bioavailability of a drug are dissolution, membrane permeability and metabolic stability. Typically, a screening cascade of firstly in vitro and then in vivo techniques is used to determine oral bioavailablity.

Dissolution, the solubilisation of the drug by the aqueous contents of the gastro-intestinal tract (GIT), can be predicted from in vitro solubility experiments conducted at appropriate pH to mimic the GIT. The anti-GPC-3 antibody may in some embodiments have a minimum solubility of 50 mg/ml. Solubility can be determined by standard procedures known in the art such as described in Adv. Drug Deliv. Rev. 23, 3-25, 1997.

Membrane permeability refers to the passage of the compound through the cells of the GIT. Lipophilicity is a key property in predicting this and is defined by in vitro Log D7.4 measurements using organic solvents and buffer. The anti-GPC-3 antibody may have a Log $D_{7.4}$ of −2 to +4 or −1 to +2. The log D can be determined by standard procedures known in the art such as described in J. Pharm. Pharmacol. 1990, 42:144.

Cell monolayer assays such as $CaCO_2$ add substantially to prediction of favourable membrane permeability in the presence of efflux transporters such as p-glycoprotein, so-called caco-2 flux. The anti-GPC-3 antibody may have a caco-2 flux of greater than $2\times10^{-6}$ $cms^{-1}$, for example greater than $5\times10^{-6}$ $cms^{-1}$. The caco flux value can be determined by standard procedures known in the art such as described in J. Pharm. Sci, 1990, 79, 595-600.

Metabolic stability addresses the ability of the GIT or the liver to metabolise compounds during the absorption process: the first pass effect. Assay systems such as microsomes, hepatocytes etc are predictive of metabolic liability. The compounds of the Examples may in some embodiments show metabolic stability in the assay system that is commensurate with an hepatic extraction of less than 0.5. Examples of assay systems and data manipulation are described in Curr. Opin. Drug Disc. Devel., 201, 4, 36-44, Drug Met. Disp., 2000, 28, 1518-1523.

Because of the interplay of the above processes further support that a drug will be orally bioavailable in humans can be gained by in vivo experiments in animals. Absolute bioavailability is determined in these studies by administering the compound separately or in mixtures by the oral route. For absolute determinations (% absorbed) the intravenous route is also employed. Examples of the assessment of oral bioavailability in animals can be found in Drug Met. Disp., 2001, 29, 82-87; J. Med Chem, 1997, 40, 827-829, Drug Met. Disp., 1999, 27, 221-226.

The term "pharmaceutically acceptable carrier" as used herein generally refers to organic or inorganic materials, which cannot react with active ingredients. The carriers include but are not limited to sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oil, cotton seed oil, sesame oil, olive oil, corn oil and oil of theobroma; polyols such as propylene glycol, glycerine, sorbitol, mannitol, and polyethylene glycol; agar; alginic acids; pyrogen-free water; isotonic saline; and phosphate buffer solution; skim milk powder; as well as other non-toxic compatible substances used in pharmaceutical formulations. Wetting agents and lubricants such as sodium lauryl sulfate, as well as coloring agents, flavoring agents, lubricants, excipients, tabletting agents, stabilizers, anti-oxidants and preservatives, can also be present.

The term "therapeutically effective amount" as used herein generally refers to an amount of an agent, for example the amount of a compound as an active ingredient, that is sufficient to effect treatment as defined herein when administered to a subject in need of such treatment. A therapeutically effective amount of a compound, salt, derivative, isomer or enantiomer of the present invention will depend upon a number of factors including, for example, the age and weight of the subject, the precise condition requiring treatment and its severity, the nature of the formulation, and the route of administration, and will ultimately be at the discretion of the attendant physician or veterinarian. However, an effective amount of a compound of the present invention for the treatment of disorders associated with bacterial or viral infection, in particular bacterial meningitis, will generally be in the range of about 10 to about 40 mg/kg body weight of recipient (mammal) per day and more usually about 40 mg/kg body weight per day. Thus, for a 70 kg adult subject, the actual amount per day would typically be about 2,800 mg, and this amount may be given in a single dose per day or more usually in a number (such as two, three, four, five or six) of sub-doses per day such that the total daily dose is the same. An effective amount of a salt of the present invention may be determined as a proportion of the effective amount of the compound per se.

The term "treatment" as used herein refers to any treatment of a condition or disease in an animal, particularly a mammal, more particularly a human, and includes: preventing the disease or condition from occurring in a subject which may be predisposed to the disease but has not yet been diagnosed as having it; inhibiting the disease or condition, i.e. arresting its development; relieving the disease or condition, i.e. causing regression of the condition; or relieving the conditions caused by the disease, i.e. symptoms of the disease.

Chemical Derivative

The term "derivative" or "derivatised" as used herein includes chemical modification of a compound. Illustrative of such chemical modifications would be replacement of hydrogen by a halo group, an alkyl group, an acyl group or an amino group.

Chemical Modification

In one embodiment, the compound may be a chemically modified compound.

The chemical modification of a compound may either enhance or reduce hydrogen bonding interaction, charge interaction, hydrophobic interaction, Van Der Waals interaction or dipole interaction between the compound and the target.

In one aspect, the identified compound may act as a model (for example, a template) for the development of other compounds.

Individual

The compounds are delivered to individuals. As used herein, the term "individual" refers to vertebrates, particularly members of the mammalian species. The term includes but is not limited to domestic animals, sports animals, primates and humans.

EXAMPLES

Example 1. Discovery

Recombinant human GPC-3 protein was used to isolate binders from a library of Fab sequences constructed by SIgN, using phage display technology.

Out of 570 clones screened, 24 clones showing the highest binding to GPC-3 in ELISA were isolated and cloned into IgG$_1$ format for further characterisation: 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1.

Example 2. Binding Affinity for GPC-3

Figure 1:
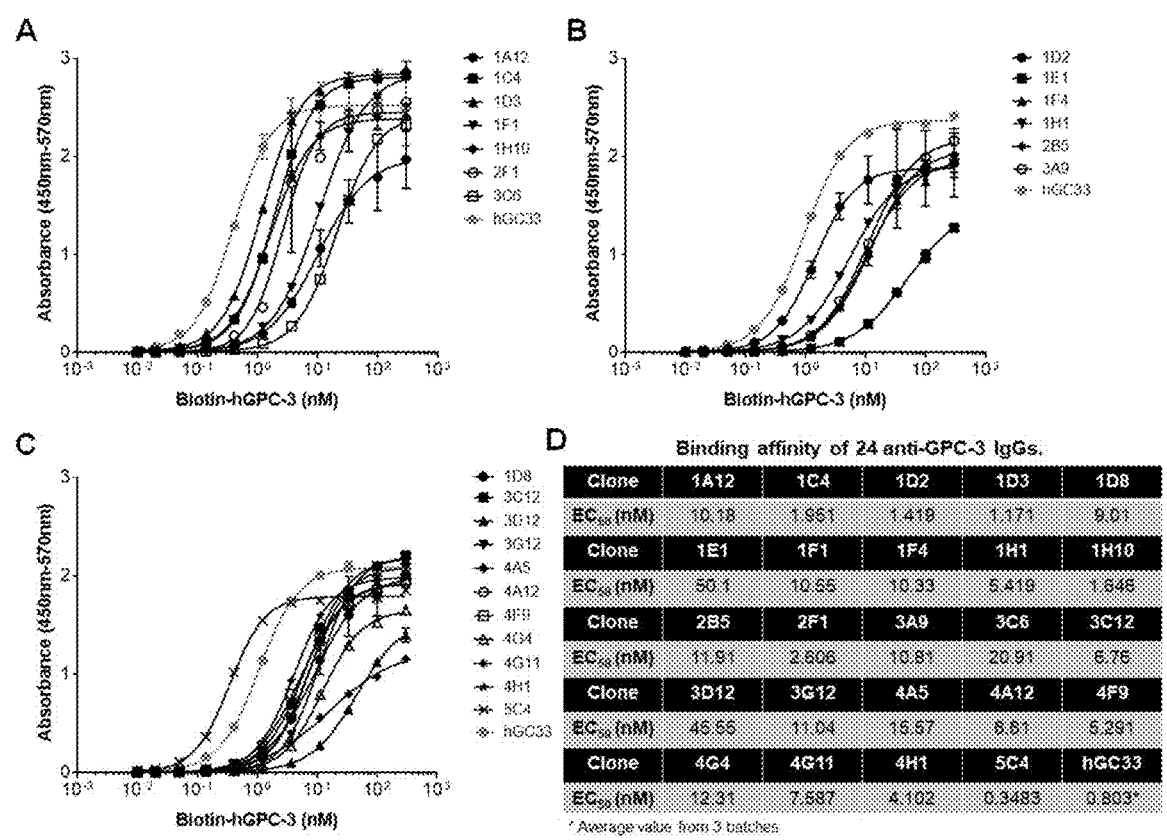
FIGS. 1A to 1D are drawings showing binding ELISA of 24 anti-GPC-3 IgG$_1$ clones. Binding ELISA experiments were performed in 3 batches (FIG. 1A, FIG. 1B, FIG. 1C) with humanized GC33 IgG$_1$ as the reference control. Calculated EC50 values were shown in a table (FIG. 1D).

The 24 antibody clones were tested in ELISA against recombinant human GPC-3 protein in 3 batches to assess binding affinity for the target, with the humanized GC33 clone (Chugai pharmaceutical, Roche) used as a reference control antibody (FIGS. 1A, 1B and 1C).

With the exception of clone 1E1 and 3D12, all other 22 clones showed medium to high affinity for human GPC-3 (FIG. 1D).

Example 3. Specific Binding of Anti-GPC-3 Antibodies to GPC-3 Expressing Cells

The ability of anti-GPC-3 antibodies to specifically recognize and bind GPC-3 on the surface of cells was measured using HepG2 (GPC-3$^{High}$), Hep3B (GPC-3$^{Medium}$) and SK-Hep1 (GPC-3$^{Negative}$) cells. HepG2 and Hep3B cells constitutively express GPC-3, while SK-Hep1 cells do not express GPC-3.

Briefly, HepG2 (GPC-3$^{High}$), Hep3B (GPC-3$^{Medium}$) and SK-Hep1 (GPC-3$^{Negative}$) cells were seeded in cell suspension at 50000 per well in 96-well round-bottom plate before incubation with different concentrations of anti-GPC-3 antibodies. Binding was measured by flow cytometry using a secondary labelled antibody.

Figure 2:
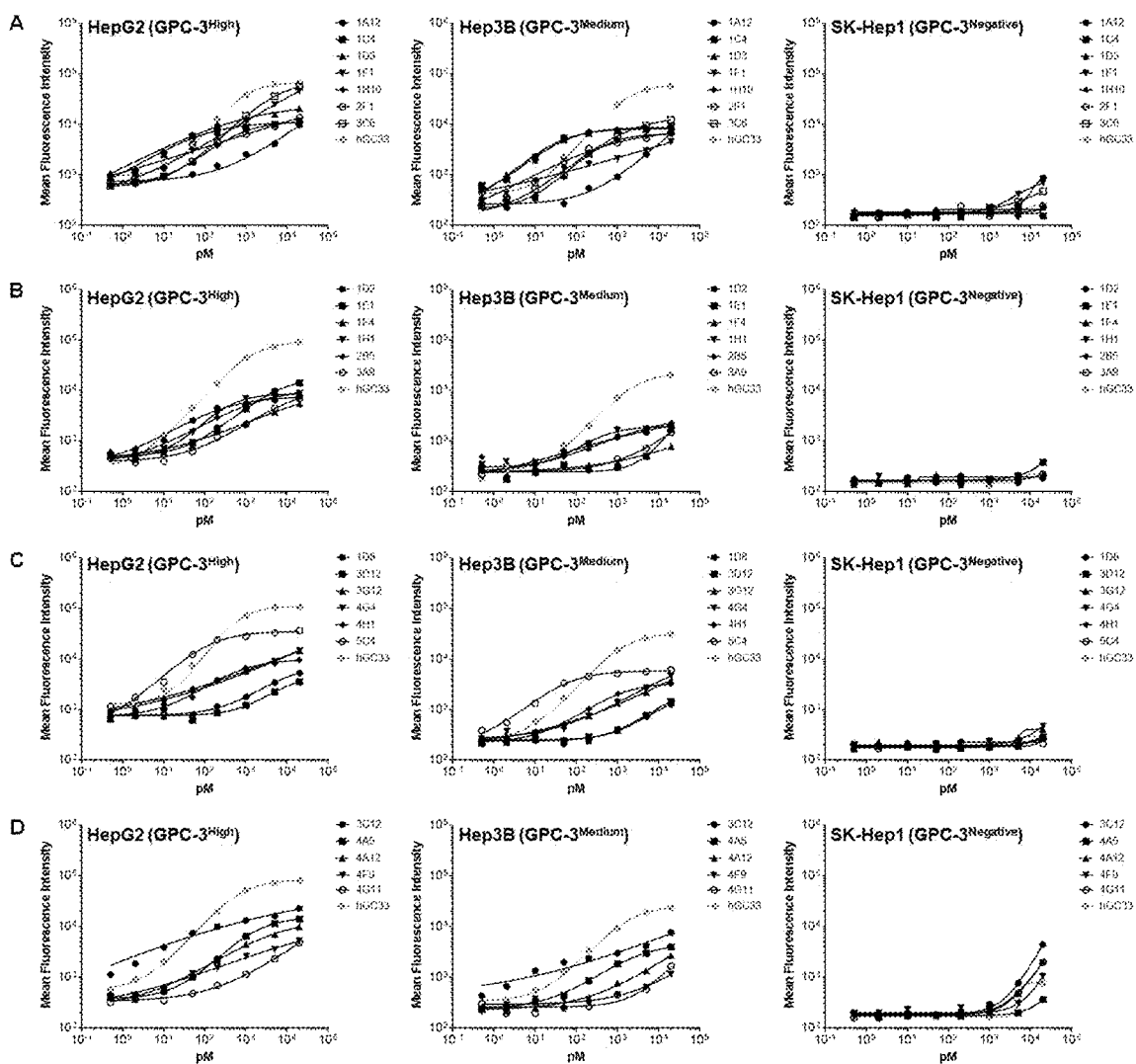
FIGS. 2A to 2D are drawings showing binding curves of 24 anti-GPC-3 clones onto GPC-3$^{High}$ HepG2 cells, GPC-3$^{Medium}$ Hep3B cells and GPC-3$^{Negative}$ SK-Hep1 cells at different antibody concentrations. Flow cytometry analyses were performed in 4 batches (FIG. 2A, FIG. 2B, FIG. 2C, FIG. 2D) with humanized GC33 IgG$_1$ as the reference control.

In this assay, most anti-GPC-3 antibodies bound strongly to the GPC-3 expressing HepG2 and Hep3B cells, but did not bind or weakly bound to GPC-3 negative SK-Hep1 cells (FIG. 2). Clone 1C4, 1D2, 1D3, 1D8, 1F4, 1H1, 1H10, 2B5, 2F1, 3A9, 3D12, 4A5, 4H1, and 5C4 showed highly specific binding to GPC-3 as they did not bind to SK-Hep1 cells even at the highest antibody concentration (20 nM). This suggests that these antibodies bind to surface of the cells in a highly specific manner dependent on GPC-3 expression.

Example 4. Cross Species Reactivity of Anti-GPC-3 Antibodies to Cynomolgus and Mouse GPC-3 Proteins As glypican-3 is a highly conserved gene, we performed cross-reactivity ELISA to assess the cross species reactivity of our anti-GPC-3 antibodies, where recombinant human, cynomolgus and mouse GPC-3 proteins were each biotinylated and used in a binding ELISA to test their bindings to each of the anti-GPC-3 IgG$_1$ clones.

Figure 3:
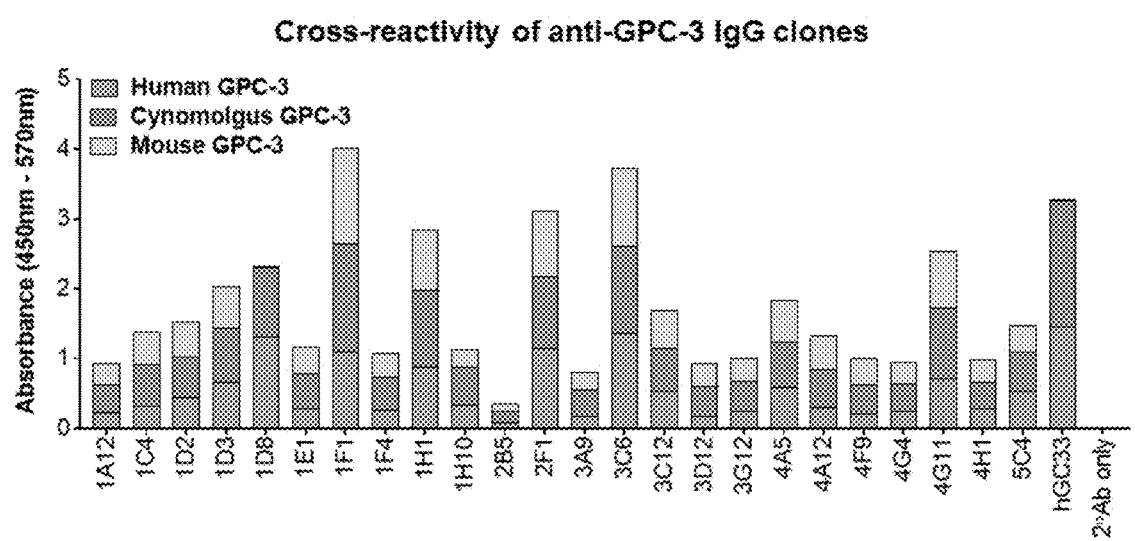
FIG. 3 is a drawing showing cross-reactivity binding ELISA of anti-GPC-3 IgG$_1$ clones to human, cynomolgus and mouse GPC-3 recombinant proteins. The humanized GC33 IgG$_1$ was used as a drawing control.

Except for clone 1D8 and the humanized GC33, all the other anti-GPC-3 IgG$_1$ clones exhibited cross-reactivity to cynomolgus GPC-3 and mouse GPC-3 (FIG. 3), indicating that these antibodies recognize common epitopes of GPC-3 protein across human, cynomolgus and mouse antigens.

Next, the ability of anti-GPC-3 antibodies to specifically recognize and bind mouse GPC-3 on the surface of cells was measured using mouse GPC-3 stably transduced Hepa1-6 cells (named as "Hepa1-6-mGPC-3") and the parental Hepa1-6 cells.

At the staining concentration of 20 nM, most anti-GPC-3 antibodies bound strongly to the Hepa1-6-mGPC-3 cells, but did not bind to the parental Hepa1-6 cells (FIG. 4A).

Clone 1C4, 1D2, 1D3, 1F1, 1H1, 1H10, 2B5, 2F1, 3A9, 3C6, 3G12, 4A12, 4G11, 4H1, and 5C4 showed highly specific binding to mouse GPC-3 as they did not show high percentage of cell binding to the parental Hepa1-6 cells (FIG. 4B).

Figure 4:
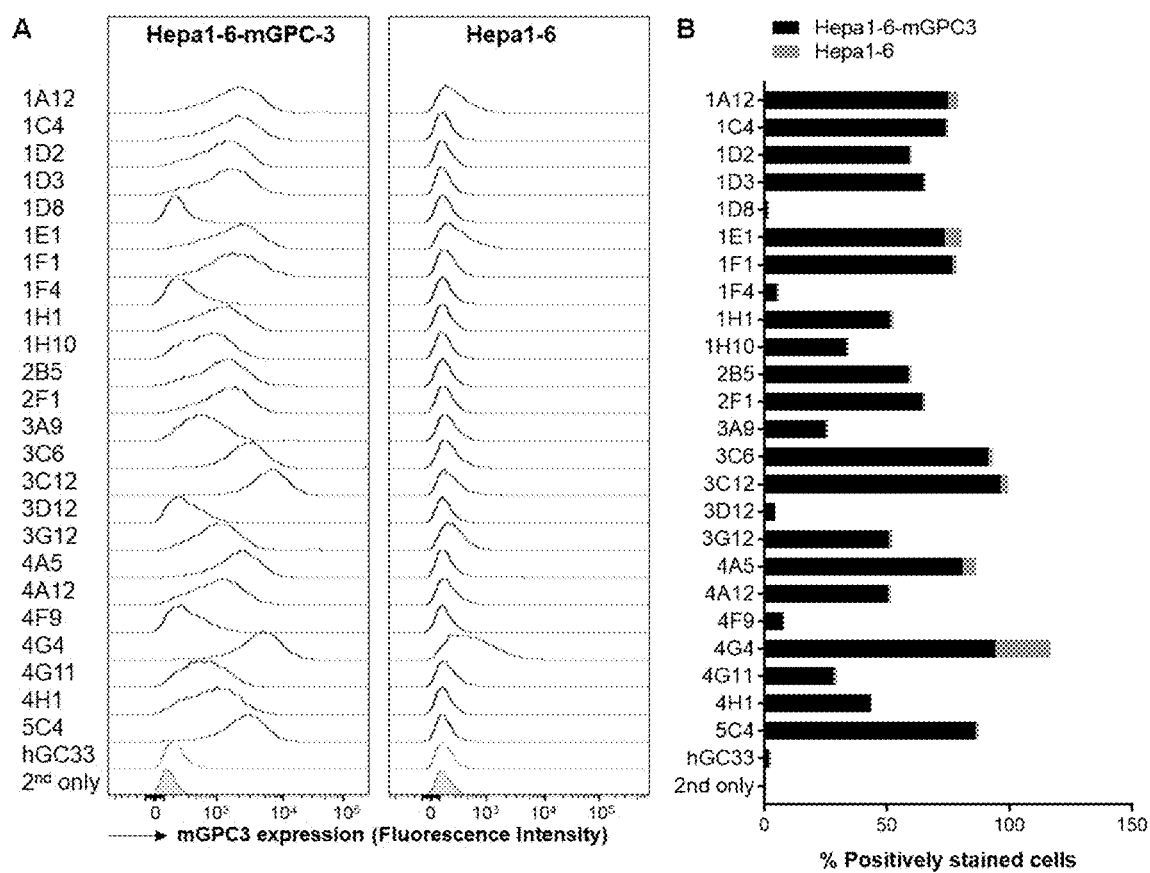
FIGS. 4A and 4B are drawings showing binding of 24 anti-GPC-3 clones onto the mouse GPC-3 transduced Hepa1-6 cells (Hepa1-6-mGPC-3), and the parental Hepa1-6 cells at the antibody concentration of 20 nM, with humanized GC33 IgG$_1$ as the reference control.

Interestingly, although clone 1F4, 3D12, and 4F9 exhibited positive binding signal in the cross-reactivity binding ELISA (FIG. 3), they could not efficiently stain the mouse GPC-3 antigen expressed on the cell surface (FIG. 4).

Example 5. In Vitro Activity: Induction of Antibody-Dependent Cell-Mediated Cytotoxicity (ADCC)

To assess the ability of the anti-GPC-3 antibodies to induce ADCC, GPC-3 positive HepG2 cells were mixed with naïve natural killer (NK) cells at a ratio of 1:2.5 (E:T ratio=2.5:1) in the absence or presence of each different anti-GPC-3 IgG$_1$ clones (2.5 µg/ml).

Figure 5:
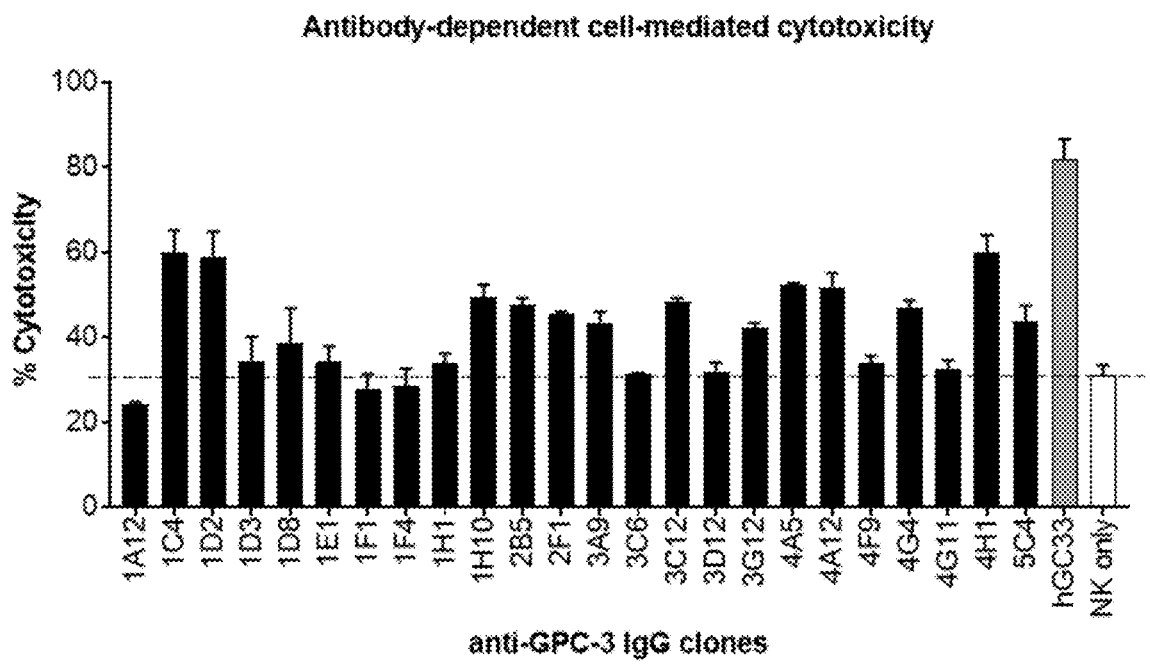
FIG. 5 is a drawing showing specific killing of GPC-3$^{High}$ HepG2 cells in ADCC assay in the presence of different anti-GPC-3 IgG$_1$ clones. Shown are mean cytotoxicity±SD in triplicates. The humanized GC33 IgG$_1$ was used as a reference control.

The cell index values were then measured continuously using xCelligence RTCA system at an interval of 15 minutes for 44 hours. In this assay, cell index values of tumour cells are measured by the impedance of current across the transistor plate caused by tumour cell adherence. The end-point cytotoxicity was calculated and shown in FIG. 5.

Compared to the cytotoxicity induced by NK cells alone, significant increase in killing was observed in more than half of the anti-GPC-3 antibody clones, with clone 1C4, 1D2 and 4H1 showing the highest antibody-dependent cell-mediated cytotoxicity.

Example 6. Use in a Chimeric Antigen Receptor (CAR) T Cell Construct

The sequences of the antibodies can also be used to construct anti-GPC-3 CAR T cells.

15 clones were chosen to be expressed as CAR in a second-generation CAR format (CD3zeta plus 4-1BB intracellular domain).

To assess the function of these anti-GPC-3 CAR T cells, T cells from healthy donors were activated by TransAct™ (CD3/CD28 agonists) in the presence of IL-2 (50 unit/ml) for 24 hours and CAR gene was introduced by lentiviral based transduction process. 72 hours post transduction, the potency of these anti-GPC-3 CAR T cells were subjected to T cell-mediated cytotoxicity assay using xCELLigence RTCA system.

The CAR T cells were proved to be highly efficient in killing tumour cells.

Figure 6:
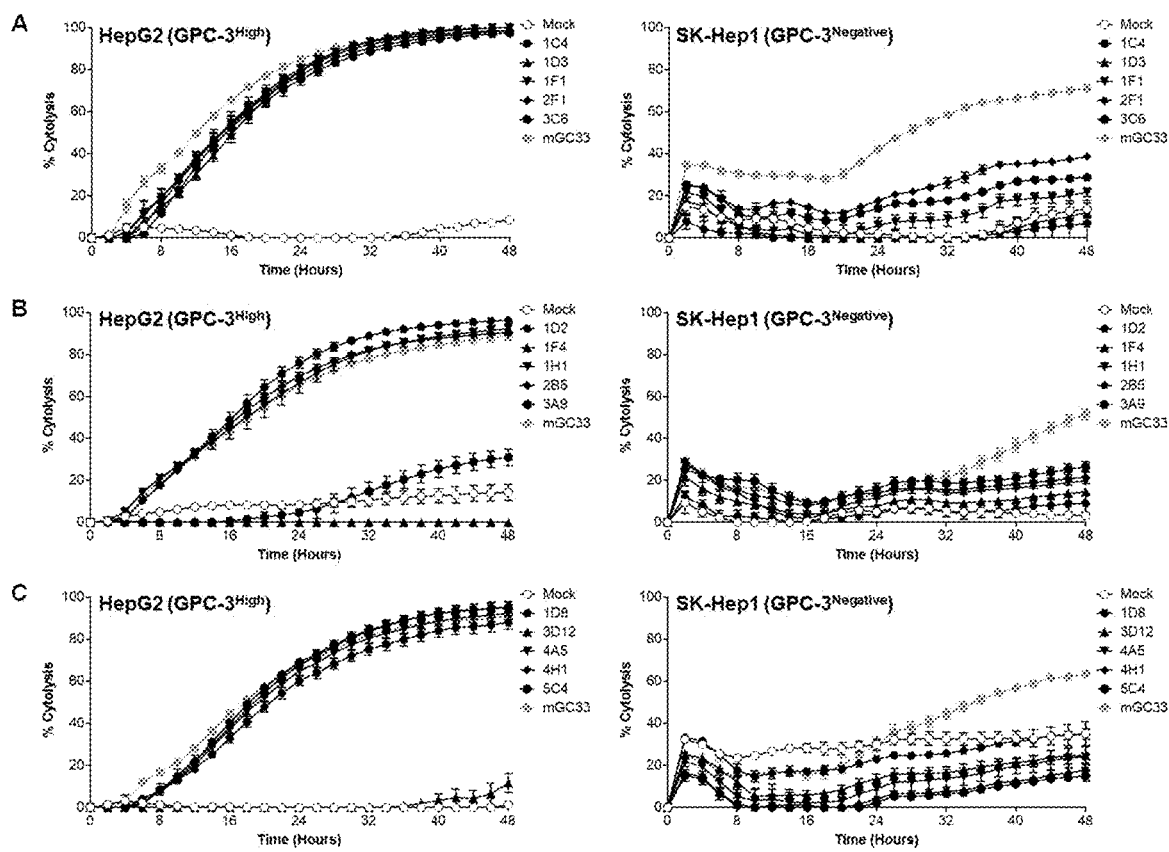
FIGS. 6A to 6C are drawings showing specific cytolysis of GPC-3$^{High}$ HepG2 cells and GPC-3$^{Negative}$ SK-Hep1 cells by anti-GPC-3 CAR-T cells with time-course measurement using xCelligence impedance assay for 48 hours. Assays were performed in 3 batches (FIG. 6A, FIG. 6B, FIG. 6C) using CAR-T cells generated from different donors. Shown are mean % cytolysis±SD in triplicates. Anti-GPC-3 CAR-T cells generated from scFv sequence using the mouse GC33 clone were used as a reference control.

While mock transduced T cells showed 10-15% cytolysis of GPC-3 expressing HepG2 cells, anti-GPC-3 CAR T cells were able to kill 30-100% of HepG2 cells (FIG. 6). Within 48 hours of co-culture, clone 1C4, 1D3, 1F1, 2F1, 3C6, 1D2, 1H1, 2B5, 1D8, 4A5, 4H1, and 5C4 based anti-GPC-3 CAR T cells could lyse 90-100% of GPC-3$^{High}$ HepG2 cells. The killing by these CAR T cells was highly specific to antigen expression, as the same CAR T cells only showed very minimal background killing of GPC-3$^{Negative}$ SK-Hep1 cells (10-30%).

In addition, 24 and 48 hours post co-culture of anti-GPC-3 CAR T cells with GPC-3$^{High}$ HepG2 cells or GPC-3$^{Negative}$ SK-Hep1 cells, cell culture supernatants were collected and subjected to ELISA to assess the cytokine release of interferon-γ and IL-2 from anti-GPC-3 CAR T cells. When co-cultured with GPC-3$^{High}$ HepG2 cells, anti-GPC-3 CAR T cells based on clone 1C4, 1D3, 1F1, 2F1, 3C6, 1D2, 1H1, 2B5, 1D8, 4A5, 4H1 and 5C4 secreted a large amount of interferon-γ and IL-2. However, levels of interferon-γ and IL-2 secretion were minimal when the anti-GPC-3 CAR T cells were added to GPC-3$^{Negative}$ SK-Hep1 cells, indicating the superior specificity of these anti-GPC-3 CAR T cells in responding to and killing of GPC-3 expressing cells (FIG. 7).

Figure 7:
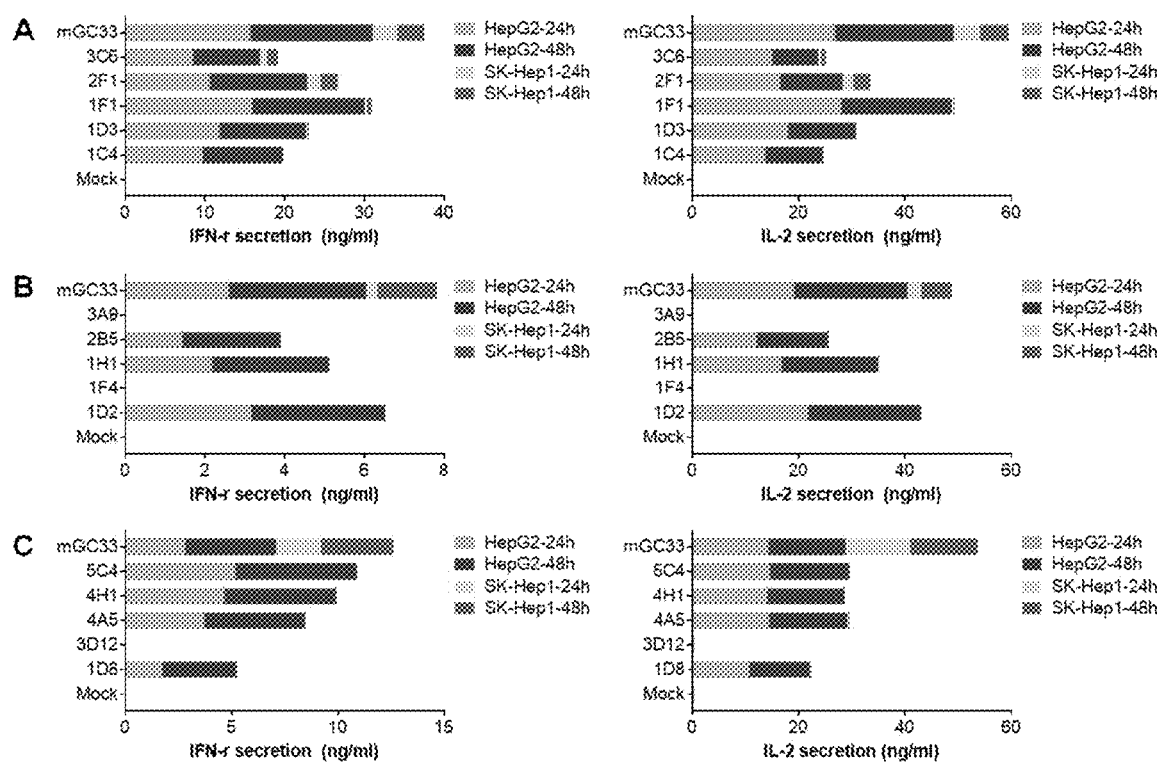
FIGS. 7A to 7C are drawings showing ELISA measurement of interferon-γ and IL-2 secretion from anti-GPC-3 CAR-T cells after 24 and 48 hours of co-culture with either GPC-3$^{High}$ HepG2 cells or GPC-3$^{Negative}$ SK-Hep1 cells. Assays were performed in 3 batches (FIG. 7A, FIG. 7B, FIG. 7C) using CAR-T cells generated from different donors. Anti-GPC-3 CAR-T cells generated from scFv sequence using the mouse GC33 clone were used as a reference control.

Interestingly, both FIG. 6 and FIG. 7 showed a moderate degree of non-specific off-target reactivity of anti-GPC-3 CAR T cells expressing mouse GC33 clone.

Example 7. Nucleotide and Amino Acid Sequences of Antibodies

Amino acid and nucleotide sequences for 24 fully human monoclonal antibodies and their derivatives, able to specifically bind glypican-3 and trigger killing of the cells expressing the antigen are set out below.

The antibodies are 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1.

Sequences
Amino-Acid Sequences
CDRs are in bold and highlighted in bold (CDR1), italic (CDR2) or underline (CDR3).

| Clone | Heavy Chain (V$_H$) Amino Acid Sequence | Light Chain (V$_L$) Amino Acid Sequence |
|---|---|---|
| 5C4 | SEQ ID NO: 1 | SEQ ID NO: 2 |
| 4H1 | SEQ ID NO: 3 | SEQ ID NO: 4 |
| 1D2 | SEQ ID NO: 5 | SEQ ID NO: 6 |
| 1C4 | SEQ ID NO: 7 | SEQ ID NO: 8 |
| 2B5 | SEQ ID NO: 9 | SEQ ID NO: 10 |
| 1F1 | SEQ ID NO: 11 | SEQ ID NO: 12 |
| 1H1 | SEQ ID NO: 13 | SEQ ID NO: 14 |
| 4A5 | SEQ ID NO: 15 | SEQ ID NO: 16 |
| 1D8 | SEQ ID NO: 17 | SEQ ID NO: 18 |
| 1D3 | SEQ ID NO: 19 | SEQ ID NO: 20 |
| 2F1 | SEQ ID NO: 21 | SEQ ID NO: 22 |
| 3C6 | SEQ ID NO: 23 | SEQ ID NO: 24 |
| 3D12 | SEQ ID NO: 25 | SEQ ID NO: 26 |
| 3A9 | SEQ ID NO: 27 | SEQ ID NO: 28 |
| 1F4 | SEQ ID NO: 29 | SEQ ID NO: 30 |
| 1H10 | SEQ ID NO: 31 | SEQ ID NO: 32 |
| 3C12 | SEQ ID NO: 33 | SEQ ID NO: 34 |
| 4G11 | SEQ ID NO: 35 | SEQ ID NO: 36 |
| 4A12 | SEQ ID NO: 37 | SEQ ID NO: 38 |
| 1A12 | SEQ ID NO: 39 | SEQ ID NO: 40 |
| 3G12 | SEQ ID NO: 41 | SEQ ID NO: 42 |
| 4F9 | SEQ ID NO: 43 | SEQ ID NO: 44 |
| 4G4 | SEQ ID NO: 45 | SEQ ID NO: 46 |
| 1E1 | SEQ ID NO: 47 | SEQ ID NO: 48 |

TABLE D1

Heavy Chain and Light Chain Amino Acid Sequence ID Numbers (sequences set out below)

HEAVY CHAIN VARIABLE DOMAIN AMINO ACID SEQUENCES FOR HUMAN IGG1 (V$_H$)

SEQ ID NO: 1: Heavy Chain Variable Domain Amino Acid Sequence of 5C4
QVQLQESGGGLVKPGGSLRLSCAASGFTFSSYSMNWVRQAPGKGLEWVAV*ISYDGSNK*
YYADSVKGRFTISRDNSKNTLYLQMNSLRTEDTAVYYCAR<u>GAGPFTGFNWFDPW</u>GQGTL SEQ ID NO: 3: Heavy Chain Variable Domain Amino Acid Sequence of 4H1
EVQLVQSGGGVVQPGRSLRLSCAASGFTFSSYAMHWVRQAPGKGLEWVAV*ISYDGSNK*
YYADSVKGRFTISRDNSKNTLYLQMNSLRAEDTAVYYCAR<u>APGLEDY</u>WGQGTL TABLE D1-continued Heavy Chain and Light Chain Amino Acid Sequence ID Numbers
(sequences set out below)

SEQ ID NO: 5: Heavy Chain Variable Domain Amino Acid Sequence of 1D2
EVQLVQSGAEVKKPGSSVKVSCKASGGTFSSYAISWVRQAPGQGLEWMGGI*IPIFGTA*
NYAQKFQGRVTITADKSTSTAYMELSSLRSEDTAVYYCAR<u>EWQQQLVPLGYMDVWGKGTT</u>

SEQ ID NO: 7: Heavy Chain Variable Domain Amino Acid Sequence of 1C4
QVQLVQSGGGLVKPGRSLRLSCTASGFTFGDYAMHWVRQAPGKGLEWVAVI*SYDGSNK*
YYADSVKGRFTISRDNSKNTLYLQMNSLRAEDTAVYYCARD<u>YGDYYRPYGMDVWGQGTT</u>

SEQ ID NO: 9: Heavy Chain Variable Domain Amino Acid Sequence of 2B5
QVQLQESGGGVVQPGRSLRLSCAASGFTFSSYAMHWVRQAPGKGLEWVAVI*SYDGSNK*
YYADSVKGRFTISRDNSKNTLYLQMNSLRAEDTAVYYCAK<u>EGTYYYDSSGYWDYYYGMDVWGQ
GTT</u>

SEQ ID NO: 11: Heavy Chain Variable Domain Amino Acid Sequence of 1F1
QVQLVQSGAEVKKPGASVKVSCKASGYTFTSYGISWVRQAPGQRLEWMGWI*NAGNGNT*
*KYSQKFQG*RVTITRDTSASTAYMELSSLRSEDTAVYYCAT<u>VVYWGQGTL</u>

SEQ ID NO: 13: Heavy Chain Variable Domain Amino Acid Sequence of 1H1
QVQLQESGAGLLRPSETLSLTCAVYGGSFSGYYWSWIRQPPGKGLEWLGEI*SHSGSTN*
YNPSLKSRVTISVDTSKNQFSLKLSSVTAADAAVYYCAR<u>WVWSGYYNGEGYFDLWGRGTL</u>

SEQ ID NO: 15: Heavy Chain Variable Domain Amino Acid Sequence of 4A5
EVQLVQSGAEVKKPGASVKVSCKASGYTFTSYGISWVRQAPGQGLEWMGWI*SAYNGNT*
NYAQKLQGRVTMTTDTSTSTAYMELRSLRSDDTAVYYCARD<u>GLSSSWFYYYYGMDVWGQGTT</u>

SEQ ID NO: 17: Heavy Chain Variable Domain Amino Acid Sequence of 1D8
QVQLVQSGAEVKKPGASVKVSCKASGYTFTSYGISWVRQAPGQGLEWMGWI*SAYNGNT*
NYAQKLQGRVTMTTDTSTSTAYMELRSLRSDDTAVYYCARD<u>GGLIAAAFGYYYYGMDVWGQGT
T</u>

SEQ ID NO: 19: Heavy Chain Variable Domain Amino Acid Sequence of 1D3
QVQLVQSGAEVKKPGASVKVSCKASGYTFTGYYMHWVRQAPGQGLEWMGWI*NPNSGGT*
NYAQNFQGRVTITRDTSASTAYMELSSLRSEDTAVYYCAR<u>GSWQTGSFDIWGQGTT</u>

SEQ ID NO: 21: Heavy Chain Variable Domain Amino Acid Sequence of 2F1
EVQLVQSGAEVKKPGSSVKVSCKASGGTFSSYAISWVRQAPGQGLEWMGGI*IPIFGTA*
NYAQKFQGRVTITADESTSTAYMELSSLRSEDTAVYYCARD<u>SPYYYYMDVWGKGTT</u>

SEQ ID NO: 23: Heavy Chain Variable Domain Amino Acid Sequence of 3C6
QVQLQESGGGVVQPGRSLRLSCAASGFTFSSYAMHWVRQAPGKGLEWVAVI*SYDGSNK*
YYADSVKGRFTISRDNSKNTLYLQMNSLRAEDTAVYYCAY<u>GRYNWNLYFDYWGQGTL</u>

SEQ ID NO: 25: Heavy Chain Variable Domain Amino Acid Sequence of 3D12
EVQLVQSGAEVKKPGSSVKVSCKASGGTFSSYAISWVRQAPGQGLEWMGGI*IPIFGTA*
NYAQKFQGRVTITADKSTSTAYMELSSLRSEDTAVYYCARG<u>IAARPSYYYYMDVWGKGTT</u>

SEQ ID NO: 27: Heavy Chain Variable Domain Amino Acid Sequence of 3A9
QVQLQQWGAGLLKPSETLSLTCAVYGGSFSGYYWSWIRQPPGKGLEWIGEI*NHSGSTN*
YNPSLKSRVTISVDTSKNQFSLKLSSVTAADTAVYYCARL<u>YKRRPFDYWGQGTL</u>

SEQ ID NO: 29: Heavy Chain Variable Domain Amino Acid Sequence of 1F4
QVQLQQWGAGLLKPSETLSLTCAVYGGSFSGYYWSWIRQPPGKGLEWIGEI*NHSGSTN*
YNPSLKSRVTISVDTSKNQFSLKLSSVTVADTAVYYCARL<u>YKRRPFDYWGQGTL</u>

SEQ ID NO: 31: Heavy Chain Variable Domain Amino Acid Sequence of 1H10
QLQLQESGGGLVQPGGSLRLSCAASGFTFSSYVMSWVRQAPGKGLEWVSTI*SGSGGS*T
YYADSVKGRFTISRDNSKNTLYLQMSSLRAEDTAVYYCVM<u>GWYFDLWGRGTL</u>

SEQ ID NO: 33: Heavy Chain Variable Domain Amino Acid Sequence of 3C12
QVTLKESGPTLVKPTQTLTLTCTFSGFSLSTSGVGVGWIRQPPGKALEWLALI*YWNDD*
KRYSPSLKSRLTITKDTSKNQVVLTMTNMDPVDTATYYCAHS<u>RIAARRVLDYWGQGTL</u>

SEQ ID NO: 35: Heavy Chain Variable Domain Amino Acid Sequence of 4G11
QVQLQESGPGLVKPSGTLSLTCAVSGGSISSSNWWSWVRQPPGKGLEWIGEI*YHSGST*
NYNPSLKSRVTISVDKSKNQFSLKLSSVTAADTAVYYCARD<u>TSGVAFDYWGQGTL</u>

SEQ ID NO: 37: Heavy Chain Variable Domain Amino Acid Sequence of 4A12
DVQLVESGGGLVQPGGSLRLSCAASGFTFSSYAMSWVRQAPGKGLEWVSAI*SGSGGS*T
YYADSVKGRFTISRDNSKNTLYLQMNSLRAEDTAVYYCAE<u>GRIQLDYWGQGTL</u>

SEQ ID NO: 39: Heavy Chain Variable Domain Amino Acid Sequence of 1A12
QVQLQQWGAGLLKPSETLSLTCAAYGGSFSGYYWSWIRQPPGKGLEWIGEI*NHSGSTN*
YNPSLKSRVTISVDTSKNQFSLKLSSVTAADTAVYYCARL<u>YKRRPFDYWGQGTL</u>

SEQ ID NO: 41: Heavy Chain Variable Domain Amino Acid Sequence of 3G12
QVQLQQWGAGLLKPSETLSLICAVYGGSFSGYYWSWIRQPPGKGLEWIGEI*NHSGSTN*
YNPSLKSRVTISVDTSKNQFSLKLSSVTAADTAVYYCARL<u>YKRRPFDYWGQGTL</u>

TABLE D1-continued

Heavy Chain and Light Chain Amino Acid Sequence ID Numbers
(sequences set out below)

SEQ ID NO: 43: Heavy Chain Variable Domain Amino Acid Sequence of 4F9
EVQLVQSGAEVKKPGASVKVSCKASGYTFRNYGISWVRQAPGQGLEWMGWI*SAYNGNT*
NYAQKLQGRVTMTTDTSTSTAYMELRSLRSDDTAVYYCARADSSSWYVGTYYYYGMDVWGQG
TT SEQ ID NO: 45: Heavy Chain Variable Domain Amino Acid Sequence of 4G4
QVQLQQWGAGLLKPSETLSLICAVYGGSFSGYYWSWIRQPPGKGLEWIGEI*NHSGS*TN
YNPSLKSRVTISVDTSKNQFSLKLSSVTAADTAVYYCARLYKRRPFDYWGQGTL SEQ ID NO: 47: Heavy Chain Variable Domain Amino Acid Sequence of 1E1
QVQLQQWGAGLLKPSETLSLICAVYGGSFSGYYWSWIRQPPGKGLEWIGEI*NHSGS*TN
YNPSLKSRVTISVDTSKNQFSLKLSSVTAADTAVYYCARLYKRRPFDYWGQGTL

LIGHT CHAIN VARIABLE DOMAIN AMINO ACID SEQUENCES FOR HUMAN IGG1 (V$_L$)

SEQ ID NO: 2: Light Chain Variable Domain Amino Acid Sequence of 5C4
EIVLTQSPATLSVSPGERATLSCRASQSVDSYLAWYQQKPGQAPRLLIY*SASTRATGI*
PARFSGTGSGTEFTLTISSLQSEDFAVYYCQQYKRWPTWTFGLGTR SEQ ID NO: 4: Light Chain Variable Domain Amino Acid Sequence of 4H1
DIQMTQSPSSLSASVGDRVTITCRASQSISSYLNWYQQKPGTAPKLLIY*AASSSLQSG*
VPSRFSGSGSGTDFALTISSLQPEDFATYYCLQDYNYPLTFGGGTK SEQ ID NO: 6: Light Chain Variable Domain Amino Acid Sequence of 1D2
ETTLTQSPGTLSLSPGERATLSCRASHSVSSNFLAWYQQKPGQAPRLLIY*AASSRTT*G
VPDRFSGSGSGTDFTLTISRLEPEDSAVYYCQQYGYSPLYTFGQGTK SEQ ID NO: 8: Light Chain Variable Domain Amino Acid Sequence of 1C4
DIQMTQSPSTLSASVGDRVTITCRASQSISKWLAWYQHKPGKAPKVLIY*KASTLQSG*V
PSRFSGSGSGTEFTLTISSLQPEDFATYYCQQLNSYPLTFGGGTK SEQ ID NO: 10: Light Chain Variable Domain Amino Acid Sequence of 2B5
DVVMTQSPLSLPVTPGEPASISCRSSQSLLDSDGYNFLDWYVQKPGQSPQRLIY*LGSI*
*RAS*GVPDRFSGSGSGTDFTLKISRVEADDVGVYYCMQALQTPWTFGQGTK SEQ ID NO: 12: Light Chain Variable Domain Amino Acid Sequence of 1F1
EIVLTQSPLSLPVTPGEPASISCRSSQSLLHSNGYNYLDWYLQKPGQSPQILIY*LGSH*
*RAS*GVPDRFSGSASGTDFTLKISRVEAEDVGVYYCMQALQTPLTFGGGTK SEQ ID NO: 14: Light Chain Variable Domain Amino Acid Sequence of 1H1
ETTLTQSPGTLSLSPGERATLSCRASQSVSSSYLAWYQQKPGQAPRLLIY*GASSRA*TG
IPDRFSGRGSGTDFTLTITRLEPEDFAVYYCQYYGSSPRTFGQGTK SEQ ID NO: 16: Light Chain Variable Domain Amino Acid Sequence of 4A5
DVVMTQSPLSLPVTPGEPASISCRSSQSLLHSNGYNYLDWYLQKPGQSPQLLIY*LGSN*
*RAS*GVPDRFSGSGSGTDFTLKISRVEAEDVGVYYCMQALQTFGQGTK SEQ ID NO: 18: Light Chain Variable Domain Amino Acid Sequence of 1D8
EIVLTQSPGTLSLSPGERATLSCRASQSVSSYLAWYQQKPGQAPRLLIY*GASSRA*TGI
PDRFSGSGSGTDFTLTISRLEPEDFAVYYCQQYERPPTFGGGTK SEQ ID NO: 20: Light Chain Variable Domain Amino Acid Sequence of 1D3
SYELTQPPSVSGTPGQSVTISCSGSNSNLGSNYVYWYQVVPGTAPKLVIY*RNKYRPP*G
VPDRFSGSKSGTSASLAISGLRSDDEAEYYCSGWDDSLSGRLFGGGTK SEQ ID NO: 22: Light Chain Variable Domain Amino Acid Sequence of 2F1
DVVMTQSPLFLPVTLGQPASISCRSSQSLVYSDGNTYLSWFQQRPGQSPRRLVY*KVSS*
*RDS*GVPDRFSGSGSGTDFTLKISRVEAEDVGVYYCMQGTHWPRTFGQGTK SEQ ID NO: 24: Light Chain Variable Domain Amino Acid Sequence of 3C6
NFMLTQPHSVSESPGKTVTISCTGSSGSIASNYVQWYQQRPGSVPTIVIY*EDNQRPS*G
VPDRFSGSIDSSSNSASLTISGLKTEDEADYYCQSFDSSNYWVFGGGTK SEQ ID NO: 26: Light Chain Variable Domain Amino Acid Sequence of 3D12
DIQMTQSPSSLSASVGDRVTITCRASQNISSYLNWYQQKPGKAPKLLIY*AASSLQSG*V
PSRFSGSGSGTDFILTISSLQPEDFATYYCQQSYSTPPTFGQGTR SEQ ID NO: 28: Light Chain Variable Domain Amino Acid Sequence of 3A9
ETTLTQSPGTLSLSPGERATLSCRASQSVSSSYLAWYQQKPGQAPRLLIY*GASSRA*TG
IPDRFSGSGSGTDFTLTISRLEPEDFAVYYCQQYGSSPITFGQGTR SEQ ID NO: 30: Light Chain Variable Domain Amino Acid Sequence of 1F4
ETTLTQSPGTLSLSPGERATLSCRASQSVSSTYLAWYQQKPGQAPRLLIY*GASSRA*TG
SPERFSGGGSGTDFTLTISRLEPEDFAVYYCQHYGNSPGTFGQGTK TABLE D1-continued Heavy Chain and Light Chain Amino Acid Sequence ID Numbers
(sequences set out below)

SEQ ID NO: 32: Light Chain Variable Domain Amino Acid Sequence of 1H10
EIVLTQSPGTLSLSPGERATLSCRASQSVSSSYLAWYQQKPGQAPRLLIY*DASNRA*TG
IPARFSGSGSGTDFTLTISSLEPEDFAVYYC<u>QQRSNWPPRAT</u>FGQGTR SEQ ID NO: 34: Light Chain Variable Domain Amino Acid Sequence of 3C12
QSVLIQPPSASVAPGKTARITCGGNNIGSKSVHWYQQKPGQSPVLVIY*QDTKRPS*GIP
ERFSGSNSGNTATLTISGAQPMDEADYYC<u>QAWYSTIMV</u>FGGGTK SEQ ID NO: 36: Light Chain Variable Domain Amino Acid Sequence of 4G11
EIVLIQSPGILSLSPGERATLSCRASQSVSSSYLAWYQQKPGQAPRLLIY*GASSRA*TG
IPDRFSGGGSGTDFTLTISRLEPEDSAVYYC<u>QQYDHSPT</u>FGQGTK SEQ ID NO: 38: Light Chain Variable Domain Amino Acid Sequence of 4A12
LPVLTQPPSVSVSPGQTARITCSGYELGDKYAFWYQQKPGQSPVLVIY*QDTKRPS*GIP
ERFSGSSSGDTATLIISGTQILDEADYYC<u>QAWDSSTHVV</u>FGGGTK SEQ ID NO: 40: Light Chain Variable Domain Amino Acid Sequence of 1A12
ETTLIQSPGTLSLSPGERATLSCRASQSISSIYLAWYQQKPGQAPRLLIY*GASRRA*TG
IPDRFSGSGSGTDFTLTISRLEPEDFAVYYC<u>QQYGSSLRT</u>FGQGTK SEQ ID NO: 42: Light Chain Variable Domain Amino Acid Sequence of 3G12
ETTLTQSPGTLSLSPGERATLSCRASQSVSSSYLAWYQQKRGQAPRLLIY*GASRRA*TG
IPDRFSGSGSGSDFTLTISRLEPEDFAVYYC<u>QQYGSSPST</u>FGQGTK SEQ ID NO: 44: Light Chain Variable Domain Amino Acid Sequence of 4F9
DVVMTQSPLSLPVTPGESASISCRSSQSLLHSNGYNYLDWYLQKPGQSPQLLIY*LGSN
RAS* GVPDRFSGSGSGTDFTLKISRVGAEDVGVYYC<u>MQVLQTPWT</u>FGQGTK SEQ ID NO: 46: Light Chain Variable Domain Amino Acid Sequence of 4G4
ETTLTQSPGTLSLSPGERATLSCRASQSVSSSYLAWYQQKPGQAPRLLIY*NASRRA*TG
IPDRFSGSGSGADFTLTISRLDPEDFAVYFC<u>QQYGSSPQT</u>FGQGTK SEQ ID NO: 48: Light Chain Variable Domain Amino Acid Sequence of 1E1
VTTLTQSPGTLSLSPGERATLSCRASESVSSRYLAWYQQRPGQAPRLLIY*GASRRA*TG
SPERFSGGGSGTDFTLTISRLEPEDFAVYYC<u>QHYGNSPGT</u>FGQGTK Nucleotide Sequences
CDRs are in bold and highlighted in bold (CDR1), italic (CDR2) or underline (CDR3).

| Clone | Heavy Chain (V$_H$) Nucleic Acid Sequence | Light Chain (V$_L$) Nucleic Acid Sequence |
|---|---|---|
| 5C4 | SEQ ID NO: 49 | SEQ ID NO: 50 |
| 4H1 | SEQ ID NO: 51 | SEQ ID NO: 52 |
| 1D2 | SEQ ID NO: 53 | SEQ ID NO: 54 |
| 1C4 | SEQ ID NO: 55 | SEQ ID NO: 56 |
| 2B5 | SEQ ID NO: 57 | SEQ ID NO: 58 |
| 1F1 | SEQ ID NO: 59 | SEQ ID NO: 60 |
| 1H1 | SEQ ID NO: 61 | SEQ ID NO: 62 |
| 4A5 | SEQ ID NO: 63 | SEQ ID NO: 64 |
| 1D8 | SEQ ID NO: 65 | SEQ ID NO: 66 |
| 1D3 | SEQ ID NO: 67 | SEQ ID NO: 68 |
| 2F1 | SEQ ID NO: 69 | SEQ ID NO: 70 |
| 3C6 | SEQ ID NO: 71 | SEQ ID NO: 72 |
| 3D12 | SEQ ID NO: 73 | SEQ ID NO: 74 |
| 3A9 | SEQ ID NO: 75 | SEQ ID NO: 76 |
| 1F4 | SEQ ID NO: 77 | SEQ ID NO: 78 |
| 1H10 | SEQ ID NO: 79 | SEQ ID NO: 80 |
| 3C12 | SEQ ID NO: 81 | SEQ ID NO: 82 |
| 4G11 | SEQ ID NO: 83 | SEQ ID NO: 84 |
| 4A12 | SEQ ID NO: 85 | SEQ ID NO: 86 |
| 1A12 | SEQ ID NO: 87 | SEQ ID NO: 88 |
| 3G12 | SEQ ID NO: 89 | SEQ ID NO: 90 |
| 4F9 | SEQ ID NO: 91 | SEQ ID NO: 92 |
| 4G4 | SEQ ID NO: 93 | SEQ ID NO: 94 |
| 1E1 | SEQ ID NO: 95 | SEQ ID NO: 96 |

TABLE D2

Heavy Chain and Light Chain Nucleic Acid Sequence ID Numbers
(sequences set out below)

HEAVY CHAIN VARIABLE DOMAIN NUCLEIC ACID SEQUENCES FOR HUMAN IGG1 (V$_H$)

SEQ ID NO: 49: Heavy Chain Variable Domain Nucleic Acid Sequence of 5C4
CAGGTGCAGCTGCAGGAGTCGGGGGGAGGCCTGGTCAAGCCTGGGGGGTCCCTGAGAC
TCTCCTGTGCAGCCTCTGGATTCACCTTCAGTAGCTATAGCATGAACTGGGTCCGCCAGGCTC
CAGGGAAGGGGCTGGAGTGGGTGGCAGTTATA*TCATATGATGGAAGTAATAAATACTATGCAG
ACTCCGTGAAGGGCCGATTCACCATCTCCAGAGACAATTCCAAGAACACGCTGTATCTGCAAA
TGAACAGCCTGAGAACTGAGGACACGGCTGTGTATTACTGTGCGAGGGGCGCGGGGCCTTTTA
CGGGATTCAACTGGTTCGACCCCTGGGGCCAGGGAACCCTG TABLE D2-continued Heavy Chain and Light Chain Nucleic Acid Sequence ID Numbers
(sequences set out below)

SEQ ID NO: 51: Heavy Chain Variable Domain Nucleic Acid Sequence of 4H1
GAGGTCCAGCTGGTACAGTCTGGGGGAGGCGTGGTCCAGCCTGGGAGGTCCCTGAGAC
TCTCCTGTGCAGCCTCTGGATTCACCTTCAGTAGCTATGCTATGCACTGGGTCCGCCAGGCTC
CAGGCAAGGGGCTGGAGTGGGTGGCAGTTATA*TCATATGATGGAAGCAATAAATACTACGCAG*
ACTCCGTGAAGGGCCGATTCACCATCTCCAGAGACAATTCCAAGAACACGCTGTATCTGCAAA
TGAACAGCCTGAGAGCTGAGGACACGGCTGTGTATTACTGTGCGAGA<u>GCCCCTGGGTTGGAGG
ACTACTGGGGCCAGGGAACCCTG</u>

SEQ ID NO: 53: Heavy Chain Variable Domain Nucleic Acid Sequence of 1D2
GAGGTCCAGCTGGTGCAGTCTGGGGCTGAGGTGAAGAAGCCTGGGTCCTCGGTGAAGG
TCTCCTGCAAGGCTTCTGGAGGCACCTTCAGCAGCTATGCTATCAGCTGGGTGCGACAGGCCC
CTGGACAAGGGCTTGAGTGGATGGGAGGGATC*ATCCCTATCTTTGGTACAGCAAACTACGCAC*
AGAAGTTCCAGGGCAGAGTCACGATTACCGCGGACAAATCCACGAGCACAGCCTACATGGAGC
TGAGCAGCCTGAGATCTGAGGACACGGCCGTGTATTACTGTGCGAGA<u>GAGTGGCAGCAGCAGC
TGGTACCCCTCGGCTACATGGACGTCTGGGGCAAAGGGACCACG</u>

SEQ ID NO: 55: Heavy Chain Variable Domain Nucleic Acid Sequence of 1C4
CAGGTCCAGCTGGTGCAGTCTGGGGGAGGCTTGGTAAAGCCAGGGCGGTCCCTGAGAC
TCTCCTGTACAGCTTCTGGATTCACCTTTGGTGATTATGCTATGCACTGGGTCCGCCAGGCTC
CAGGCAAGGGGCTGGAGTGGGTGGCAGTTATA*TCATATGATGGAAGCAATAAATACTATGCAG*
ACTCCGTGAAGGGCCGATTCACCATCTCCAGAGACAATTCCAAGAACACGCTGTATCTGCAAA
TGAACAGCCTGAGAGCTGAGGACACGGCTGTGTATTACTGTGCGAGA<u>GATTACGGTGATTACT
ATCGGCCCTACGGTATGGACGTCTGGGGCCAAGGGACCACG</u>

SEQ ID NO: 57: Heavy Chain Variable Domain Nucleic Acid Sequence of 2B5
CAGGTGCAGCTGCAGGAGTCCGGGGGAGGCGTGGTCCAGCCTGGGAGGTCCCTGAGAC
TCTCCTGTGCAGCCTCTGGATTCACCTTCAGTAGCTATGCTATGCACTGGGTCCGCCAGGCTC
CAGGCAAGGGGCTGGAGTGGGTGGCAGTTATA*TCATATGATGGAAGCAATAAATACTACGCAG*
ACTCCGTGAAGGGCCGATTCACCATCTCCAGAGACAATTCCAAGAACACGCTGTATCTGCAAA
TGAACAGCCTGAGAGCTGAGGACACGGCTGTGTATTACTGTGCGAAA<u>GAGGGAACGTATTACT
ATGATAGTAGTGGTTATTGGGACTACTACTACGGTATGGACGTCTGGGGCCAAGGGACCACG</u>

SEQ ID NO: 59: Heavy Chain Variable Domain Nucleic Acid Sequence of 1F1
CAGGTCCAGCTGGTGCAGTCTGGAGCTGAGGTGAAGAAGCCTGGGGCCTCAGTGAAGG
TCTCCTGCAAGGCTTCTGGTTACACCTTTACCAGCTATGGTATCAGCTGGGTGCGACAGGCCC
CCGGACAAAGGCTTGAGTGGATGGGATGGATC*AACGCTGGCAATGGTAACA*CAAATATTCAC
AGAAGTTCCAGGGCAGAGTCACCATTACCAGGGACACATCCGCGAGCACAGCCTACATGGAGC
TGAGCAGCCTGAGATCTGAAGACACGGCTGTGTATTACTGTGCGACC<u>GTTGTCTACTGGGGCC
AGGGCACCCTG</u>

SEQ ID NO: 61: Heavy Chain Variable Domain Nucleic Acid Sequence of 1H1
CAGGTGCAGCTGCAGGAGTCCGGCGCAGGACTGTTGAGGCCTTCGGAGACCCTGTCCC
TCACTTGCGCTGTCTATGGTGGGTCCTTCAGTGGTTACTACTGGAGCTGGATCCGCCAGCCCC
CAGGGAAGGGGCTGGAGTGGCTTGGGGAAATC*AGTCATAGTGGAAGCACCAACTACAACCCGT
CCCTCAAGAGTCGAGTCACCATATCAGTTGACACGTCCAAGAACCAGTTCTCCCTGAAGCTGA
GCTCTGTGACCGCCGCGGACGCGGCTGTATATTACTGTGCGAGA<u>TGGGTTTGGAGTGGTTATT
ATAACGGTGAGGGGTACTTCGATCTC*TGGGGCCGTGGCACCCTG</u>

SEQ ID NO: 63: Heavy Chain Variable Domain Nucleic Acid Sequence of 4A5
GAGGTCCAGCTGGTGCAGTCTGGAGCTGAGGTGAAGAAGCCTGGGGCCTCAGTGAAGG
TCTCCTGCAAGGCTTCTGGTTACACCTTTACCAGCTACGGTATCAGCTGGGTGCGACAGGCCC
CTGGACAAGGGCTTGAGTGGATGGGATGGATC*AGCGCTTACAATGGTAACA*CAAACTATGCAC
AGAAGCTCCAGGGCAGAGTCACCATGACCACAGACACATCCACGAGCACAGCCTACATGGAGC
TGAGGAGCCTGAGATCTGACGACACGGCCGTGTATTACTGTGCGAGA<u>GACGGATTAAGCAGCA
GCTGGTTCTACTACTACTACGGTATGGACGTCTGGGGCCAAGGGACCACG</u>

SEQ ID NO: 65: Heavy Chain Variable Domain Nucleic Acid Sequence of 1D8
CAGGTCCAGCTGGTACAGTCTGGAGCTGAGGTGAAGAAGCCTGGGGCCTCAGTGAAGG
TCTCCTGCAAGGCTTCTGGTTACACCTTTACCAGCTACGGTATCAGCTGGGTGCGACAGGCCC
CTGGACAAGGGCTTGAGTGGATGGGATGGATC*AGCGCTTACAATGGTAACA*CAAACTATGCAC
AGAAGCTCCAGGGCAGAGTCACCATGACCACAGACACATCCACGAGCACAGCCTACATGGAGC
TGAGGAGCCTGAGATCTGACGACACGGCCGTGTATTACTGTGCGAGA<u>TGGGGGACTTATAG
CAGCAGCTTTCGGTTACTACTACTACGGTATGGACGTCTGGGGCCAAGGGACCACG</u>

SEQ ID NO: 67: Heavy Chain Variable Domain Nucleic Acid Sequence of 1D3
CAGGTGCAGCTGGTGCAGTCTGGGGCTGAGGTGAAGAAGCCTGGGGCCTCAGTGAAGG
TCTCCTGCAAGGCTTCTGGATACACCTTCACCGGCTACTATATGCACTGGGTGCGACAGGCCC
CTGGACAAGGGCTTGAGTGGATGGGATGGATC*AACCCTAACAGTGGTGGCA*CAAACTATGCAC
AGAACTTTCAGGGCAGAGTCACCATTACCAGGGACACATCCGCGAGCACAGCCTACATGGAGC
TGAGCAGCCTGAGATCTGAGGACACGGCCGTGTATTACTGTGCGAGG<u>GGATCGTGGCAAACGG
GTTCTTTTGATATCTGGGGCCAAGGAACCACG</u>

SEQ ID NO: 69: Heavy Chain Variable Domain Nucleic Acid Sequence of 2F1
GAGGTCCAGCTGGTGCAGTCTGGGGCTGAGGTGAAGAAGCCTGGGTCCTCGGTGAAGG
TCTCCTGCAAGGCTTCTGGAGGCACCTTCAGCAGCTATGCTATCAGCTGGGTGCGACAGGCCC
CTGGACAAGGGCTTGAGTGGATGGGAGGGATC*ATCCCTATCTTTGGTACAGCAAACTACGCAC*
AGAAGTTCCAGGGCAGAGTCACGATTACCGCGGACGAATCCACGAGCACAGCCTACATGGAGC TABLE D2-continued Heavy Chain and Light Chain Nucleic Acid Sequence ID Numbers
(sequences set out below)

TGAGCAGCCTGAGATCTGAGGACACGGCCGTGTATTACTGTGCGAGA<u>GACAGCCCCTACTACT
ACTACATGGACGTCTGGGGCAAAGGGACCACG</u>

SEQ ID NO: 71: Heavy Chain Variable Domain Nucleic Acid Sequence of 3C6
CAGGTGCAGCTGCAGGAGTCGGGGGGAGGCGTGGTCCAGCCTGGGAGGTCCCTGAGAC
TCTCCTGTGCAGCCTCTGGATTCACCTTCAGTAGCTATGCTATGCACTGGGTCCGCCAGGCTC
CAGGCAAGGGGCTGGAGTGGGTGGCAGTTATA*TCATATGATGGAAGTAATAAATACTACGCAG
ACTCCGTGAAGGGCCGATTCACCATCTCCAGAGACAATTCCAAGAACACGCTGTATCTGCAAA
TGAACAGCCTGAGAGCTGAGGACACGGCTGTGTATTACTGTGCGTAC<u>GGTAGATACAACTGGA
ATCTTTACTTTGACTAC</u>TGGGGCCAGGGAACCCTG SEQ ID NO: 73: Heavy Chain Variable Domain Nucleic Acid Sequence of 3D12
GAAGTGCAGCTGGTGCAGTCTGGGGCTGAGGTGAAGAAGCCTGGGTCCTCGGTGAAGG
TCTCCTGCAAGGCTTCTGGAGGCACCTTCAGCAGCTATGCTATCAGCTGGGTGCGACAGGCCC
CTGGACAAGGGCTTGAGTGGATGGGAGGGATC*ATCCCTATCTTTGGTACAGCAAACTACGCAC
AGAAGTTCCAGGGCAGAGTCACGATTACCGCGGACAAATCCACGAGCACAGCCTACATGGAGC
TGAGCAGCCTGAGATCTGAGGACACGGCCGTGTATTACTGTGCGAGA<u>GGCATAGCAGCTCGTC
CGAGCTACTACTACTACATGGACGTC</u>TGGGGCAAAGGGACCACG SEQ ID NO: 75: Heavy Chain Variable Domain Nucleic Acid Sequence of 3A9
CAGGTGCAGCTACAGCAGTGGGGCGCAGGACTGTTGAAGCCTTCGGAGACCCTGTCCC
TCACCTGCGCTGTCTATGGTGGGTCCTTCAGTGGTTACTACTGGAGCTGGATCCGCCAGCCCC
CAGGGAAGGGGCTGGAGTGGATTGGGGAAATCA*ATCATAGTGGAAGCACCAACTACAACCCGT
CCCTCAAGAGTCGAGTCACCATATCAGTAGACACGTCCAAGAACCAGTTCTCCCTGAAGCTGA
GCTCTGTGACCGCCGCGGACACGGCTGTGTATTACTGTGCGAGA<u>CTTTATAAAAGGAGGCCCT
TTGACTAC</u>TGGGGCCAGGGCACCCTG SEQ ID NO: 77: Heavy Chain Variable Domain Nucleic Acid Sequence of 1F4
CAGGTGCAGCTACAGCAGTGGGGCGCAGGACTGTTGAAGCCTTCGGAGACCCTGTCCC
TCACCTGCGCTGTCTATGGTGGGTCCTTCAGTGGTTACTACTGGAGCTGGATCCGCCAGCCCC
CAGGGAAGGGGCTGGAGTGGATTGGGGAAATCA*ATCATAGTGGAAGCACCAACTACAACCCGT
CCCTCAAGAGTCGAGTCACCATATCAGTAGACACGTCCAAGAACCAGTTCTCCCTGAAGCTGA
GCTCTGTGACCGTCGCGGACACGGCTGTGTATTACTGTGCGAGA<u>CTTTATAAAAGGAGGCCCT
TTGACTAC</u>TGGGGCCAGGGAACCCTG SEQ ID NO: 79: Heavy Chain Variable Domain Nucleic Acid Sequence of 1H10
CAGCTGCAGCTGCAGGAGTCCGGGGGAGGCTTGGTACAGCCTGGGGGGTCCCTGAGAC
TCTCCTGTGCAGCCTCTGGATTCACCTTTAGCAGCTATGTCATGAGCTGGGTCCGCCAGGCTC
CAGGGAAGGGGCTGGAGTGGGTCTCAACTATC*AGTGGTAGTGGTGGGAGCACATACTACGCAG
ACTCCGTGAAGGGCAGATTCACCATCTCCAGAGACAATTCCAAGAACACGCTGTATCTTCAAA
TGAGCAGTCTGAGAGCTGAGGACACGGCTGTGTATTATTGTGTGATG<u>GGCTGGTACTTCGATC
TC</u>TGGGGCCGTGGAACCCTG SEQ ID NO: 81: Heavy Chain Variable Domain Nucleic Acid Sequence of 3C12
CAGGTCACCTTGAAGGAGTCTGGTCCTACGCTGGTGAAACCCACACAGACCCTCACGC
TGACCTGCACCTTCTCTGGGTTCTCACTCAGCACTAGTGGAGTGGGTGTGGGCTGGATCCGTC
AGCCCCCAGGAAAGGCCCTGGAGTGGCTTGCACTCATT*TATTGGAATGATGATAAGCGCTACA
GCCCATCTCTGAAGAGCAGGCTCACCATCACCAAGGACACCTCCAAAAACCAGGTGGTCCTTA
CAATGACCAACATGGACCCTGTGGACACAGCCACATATTACTGTGCACAC<u>AGCCGTATAGCAG
CTCGTCGGGTGCTTGACTAC</u>TGGGGCCAGGGAACCCTG SEQ ID NO: 83: Heavy Chain Variable Domain Nucleic Acid Sequence of 4G11
CAGGTGCAGCTGCAGGAGTCGGGCCCAGGACTGGTGAAGCCTTCGGGGACCCTGTCCC
TCACCTGCGCTGTCTCTGGTGGCTCCATCAGCAGTAGTAACTGGTGGAGTTGGGTCCGCCAGC
CCCCAGGGAAGGGGCTGGAGTGGATTGGGGAAATC*TATCATAGTGGGAGCACCAACTACAACC
CGTCCCTCAAGAGTCGAGTCACCATATCAGTAGACAAGTCCAAGAACCAGTTCTCCCTGAAGC
TGAGCTCTGTGACCGCCGCGGACACGGCCGTGTATTACTGTGCGAGA<u>GATACTTCTGGGGTTG
CTTTTGACTAC</u>TGGGGCCAGGGCACCCTG SEQ ID NO: 85: Heavy Chain Variable Domain Nucleic Acid Sequence of 4A12
GACGTGCAGCTCGTGGAGTCTGGAGGAGGCTTGGTACAGCCTGGGGGGTCCCTGAGAC
TCTCCTGTGCAGCCTCTGGATTCACCTTTAGCAGCTATGCCATGAGCTGGGTCCGCCAGGCTC
CAGGGAAGGGGCTGGAGTGGGTCTCAGCTATT*AGTGGTAGTGGTGGTAGCACATACTACGCAG
ACTCCGTGAAGGGCCGGTTCACCATCTCCAGAGACAATTCCAAGAACACGCTGTATCTGCAAA
TGAACAGCCTGAGAGCCGAGGACACGGCCGTATATTACTGTGCGAGG<u>GGAGGATACAGCTTG
ACTAC</u>TGGGGCCAGGGAACCCTG SEQ ID NO: 87: Heavy Chain Variable Domain Nucleic Acid Sequence of 1A12
CAGGTGCAGCTACAGCAGTGGGGCGCAGGACTGTTGAAGCCTTCGGAGACCCTGTCCC
TCACCTGCGCTGCCTATGGTGGGTCCTTCAGTGGTTACTACTGGAGCTGGATCCGCCAGCCCC
CAGGGAAGGGGCTGGAGTGGATTGGGGAAATCA*ATCATAGTGGAAGCACCAACTACAACCCGT
CCCTCAAGAGTCGAGTCACCATATCAGTAGACACGTCCAAGAACCAGTTCTCCCTGAAGCTGA TABLE D2-continued Heavy Chain and Light Chain Nucleic Acid Sequence ID Numbers
(sequences set out below)

GCTCTGTGACCGCCGCGGACACGGCTGTGTATTACTGTGCGAGAC<u>TTTATAAAAGGAGGCCCT
TTGACTAC</u>TGGGGCCAGGGAACCCTG

SEQ ID NO: 89: Heavy Chain Variable Domain Nucleic Acid Sequence of 3G12
CAGGTGCAGCTACAGCAGTGGGGCGCAGGACTGTTGAAGCCTTCGGAGACCCTGTCCC
TCACCIGCGCTGTCTATGGTGGGTCCTTCAGTGGTTACTACTGGAGCTGGATCCGCCAGCCCC
CAGGGAAGGGGCTGGAGTGGATTGGGGAAATC*AATCATAGTGGAAG*CACCAACTACAACCCGT
CCCTCAAGAGTCGAGTCACCATATCAGTAGACACGTCCAAGAACCAGTTCTCCCTGAAGCTGA
GCTCTGTGACCGCCGCGGACACGGCTGTGTATTACTGTGCGAGAC<u>TTTATAAAAGGAGGCCCT
TTGACTAC</u>TGGGGCCAGGGCACCCTG SEQ ID NO: 91: Heavy Chain Variable Domain Nucleic Acid Sequence of 4F9
GAGGTCCAGCTGGTGCAGTCTGGAGCTGAGGTGAAGAAGCCTGGGGCCTCAGTGAAAG
TCTCCTGCAAGGCTTCTGGTTACACCTTTCGTAACTATGGTATCAGTTGGGTGCGACAGGCCC
CIGGACAAGGGCTIGAGIGGAIGGGAIGGATC*AGCGCTTACAATGG*TAACACAAACTATGCAC
AGAAGCTCCAGGGCAGAGTCACCATGACCACAGACACATCCACGAGCACCAGCCTACATGGAGC
TGAGGAGCCTGAGATCTGACGACACGGCCGTGTATTACTGTGCGAGAG<u>CGGATAGCAGCAGCT
GGTACGTCGGGACTTACTACTACTACTACGGTATGGACGTC</u>TGGGGCCAAGGGACCACG SEQ ID NO: 93: Heavy Chain Variable Domain Nucleic Acid Sequence of 4G4
CAGGTGCAGCTACAGCAGTGGGGCGCAGGACTGTTGAAGCCTTCGGAGACCCTGTCCC
TCACCTGCGCTGTCTATGGTGGGTCCTTCAGTGGTTACTACTGGAGCTGGATCCGCCAGCCCC
CAGGGAAGGGGCTGGAGTGGATTGGGGAAATC*AATCATAGTGGAAG*CACCAACTACAACCCGT
CCCTCAAGAGTCGAGTCACCATATCAGTAGACACGTCCAAGAACCAGTTCTCCCTGAAGCTGA
GCTCTGTGACCGCCGCGGACACGGCTGTGTATTACTGTGCGAGAC<u>TTTATAAAAGGAGGCCCT
TTGACTAC</u>TGGGGCCAGGGCACCCTG SEQ ID NO: 95: Heavy Chain Variable Domain Nucleic Acid Sequence of 1E1
CAGGTGCAGCTACAGCAGTGGGGCGCAGGACTGTTGAAGCCTTCGGAGACCCTGTCCC
TCACCTGCGCTGTCTATGGTGGGTCCTTCAGTGGTTACTACTGGAGCTGGATCCGCCAGCCCC
CAGGGAAGGGGCTGGAGTGGATTGGGGAAATC*AATCATAGTGGAAG*CACCAACTACAACCCGT
CCCTCAAGAGTCGAGTCACCATATCAGTAGACACGTCCAAGAACCAGTTCTCCCTGAAGCTGA
GCTCTGTGACCGCCGCGGACACGGCTGTGTATTACTGTGCGAGAC<u>TTTATAAAAGGAGGCCCT
TTGACTAC</u>TGGGGCCAGGGCACCCTG

LIGHT CHAIN VARIABLE DOMAIN NUCLEIC ACID SEQUENCES FOR HUMAN IGG1 (V$_L$)

SEQ ID NO: 50: Light Chain Variable Domain Nucleic Acid Sequence of 5C4
GAAATTGTGTTGACACAGTCTCCAGCCACCCTGTCTGTGTCTCCAGGGGAGAGAGCCA
CCCTCTCCTGCAGGGCCAGTCAGAGTGTTGACAGCTACTTAGCCTGGTACCAGCAGAAACCTG
GCCAGGCTCCCCGGCTCCTCATCTATA*GTGCGTCCACGAGGGC*CACTGGTATCCCAGCCAGGT
TCAGTGGCACTGGGTCTGGGACAGAGTTCACTCTCACCATCAGCAGCCTGCAGTCTGAAGATT
TTGCAGTTTACTACTGTC<u>AGCAGTATAAGAGGTGGCCCACGTGGACGTT</u>CGGTCTAGGGACCA
GG SEQ ID NO: 52: Light Chain Variable Domain Nucleic Acid Sequence of 4H1
GACATCCAGATGACCCAGTCTCCATCCTCCCTGTCTGCATCTGTAGGAGACAGAGTCA
CCATCACTTGCCGGGCAAGTCAGAGCATTAGCAGCTATTTAAATTGGTATCAGCAGAAACCAG
GGACAGCCCCTAAGCTCCTGATCTATG*CTGCATCATCCAGTTTACAAAGT*GGGGTCCCATCAA
GGTTCAGCGGCAGTGGATCTGGCACAGATTTCGCTCTCACCATCAGCAGCCTGCAGCCTGAAG
ATTTTGCAACTTATTACTGT<u>CTACAAGATTACAATTACCCTCTCACTTT</u>CGGCGGAGGGACCA
AG SEQ ID NO: 54: Light Chain Variable Domain Nucleic Acid Sequence of 1D2
GAAACGACACTCACGCAGTCTCCAGGCACCCTGTCTTTGTCTCCAGGGGAAAGAGCCA
CCCTCTCCTGTAGGGCCAGTCACAGTGTTAGCAGCAACTTCTTAGCCTGGTACCAGCAGAAAC
CTGGCCAGGCTCCCAGGCTCCTCATCTATG*CTGCATCCAGCAGGAC*CACTGGCGTCCCAGACA
GGTTCAGTGGCAGTGGGTCTGGGACAGACTTCACTCTCACCATCAGCAGACTGGAGCCTGAAG
ATTCTGCAGTGTATTACTGT<u>CAGCAATATGGTTACTCACCCCTGTACACT</u>TTTGGCCAGGGGA
CCAAG SEQ ID NO: 56: Light Chain Variable Domain Nucleic Acid Sequence of 1C4
GACATCCAGATGACCCAGTCTCCTTCCACCCTGTCTGCCTCTGTAGGAGACAGAGTCA
CCATCACTTGTCGGGCCAGTCAGAGTATTAGTAAGTGGTTGGCCTGGTATCAGCATAAACCAG
GGAAAGCCCCTAAAGTCCTGATCTATA*AGGCGTCTACTTTACAAAGT*GGGGTCCCGTCGAGGT
TCAGCGGCAGTGGATCTGGGACAGAATTCACTCTCACAATCAGCAGCCTGCAGCCTGAAGATT
TTGCAACTTATTACTGT<u>CAACAGCTTAATAGTTACCCGCTCACTTT</u>CGGCGGAGGGACCAAG SEQ ID NO: 58: Light Chain Variable Domain Nucleic Acid Sequence of 2B5
GATGTTGTGATGACTCAGTCTCCACTCTCCCTGCCCGTCACCCCTGGAGAGCCGGCCT
CCATCTCCTGCAGGTCTAGCCAGAGCCTCCTGGATAGTGACGGATACAACTTTTTGGATTGGT
ATGTGCAGAAGCCAGGGCAGTCTCCACAGCGCCTGATCTATT*TGGGCTCTATT*CGGGCCTCCG
GGGTCCCTGACAGGTTCAGTGGCAGTGGATCAGGCACAGATTTTACACTGAAAATCAGCAGAG
TGGAGGCTGACGATGTTGGGGTTTATTATTGC<u>ATGCAAGCTCTACAAACTCCTTGGACGTT</u>CG
GCCAAGGGACCAAG TABLE D2-continued Heavy Chain and Light Chain Nucleic Acid Sequence ID Numbers
(sequences set out below)

SEQ ID NO: 60: Light Chain Variable Domain Nucleic Acid Sequence of 1F1
GAAATTGTGCTGACTCAGTCTCCACTCTCCCTGCCCGTCACCCCTGGAGAGCCGGCCT
CCATCTCCTGCAGGTCTAGTCAGAGCCTCCTGCATAGTAATGGATACAACTATTTGGATTGGT
ACCTGCAGAAGCCAGGGCAGTCTCCACAGATCCTGATCTAC*TTGGGTTCTCATCGGGCCTCCG*
GGGTCCCTGACAGGTTCAGTGGCAGTGCATCAGGCACAGATTTTACACTGAAAATCAGCAGAG
TGGAGGCTGAGGATGTTGGGGTTTATTACTGCATGCAAGCTCTACAAACTCCCCTCACTTTCG
GCGGAGGGACCAAG SEQ ID NO: 62: Light Chain Variable Domain Nucleic Acid Sequence of 1H1
GAAACGACACTCACGCAGTCTCCTGGCACCCTGTCTTTGTCTCCAGGTGAAAGAGCCA
CCCTCTCCTGTAGGGCCAGTCAGAGTGTTAGCAGCAGCTACTTAGCCTGGTACCAGCAGAAGC
CTGGCCAGGCTCCCAGGCTCCTCATCTAT*GGTGCATCCAGCAGGGCC*ACTGGCATCCCAGACA
GGTTCAGTGGCCGTGGGTCTGGGACAGACTTCACTCTCACTATCACCAGACTGGAGCCTGAAG
ATTTTGCAGTGTATTACTGTCAGTACTATGGTAGCTCACCTCGGACTTTTGGCCAGGGGACCA
AG SEQ ID NO: 64: Light Chain Variable Domain Nucleic Acid Sequence of 4A5
GATGTTGTGATGACTCAGTCTCCACTATCCCTGCCCGTCACCCCTGGAGAGCCGGCCT
CCATCTCCTGCAGGTCTAGTCAGAGCCTCCTGCATAGTAATGGATACAACTATTTGGATTGGT
ACCTGCAGAAGCCAGGGCAGTCTCCACAGCTCCTGATCTAT*TTGGGTTCTAATCGGGCCTCCG*
GGGTCCCTGACAGGTTCAGTGGCAGTGGATCAGGCACAGATTTTACACTGAAAATCAGCAGAG
TGGAGGCTGAGGATGTTGGGGTTTATTACTGCATGCAAGCTCTACAAACTTTTGGCCAGGGGA
CCAAG SEQ ID NO: 66: Light Chain Variable Domain Nucleic Acid Sequence of 1D8
GAAATTGTGTTGACGCAGTCTCCAGGCACCCTGTCTTTGTCTCCAGGGGAAAGAGCCA
CCCTCTCCTGCAGGGCCAGTCAGAGTGTTAGCAGCTACTTAGCCTGGTACCAGCAGAAACCTG
GCCAGGCTCCCAGGCTCCTCATCTAT*GGTGCATCCAGCAGGGCC*ACTGGCATCCCAGACAGGT
TCAGTGGCAGTGGGTCTGGGACAGACTTCACTCTCACCATCAGCAGACTGGAGCCTGAAGATT
TTGCAGTGTACTACTGTCAACAGTATGAGAGGCCCCCACTTTCGGCGGGGGGACCAAG SEQ ID NO: 68: Light Chain Variable Domain Nucleic Acid Sequence of 1D3
TCCTATGAGCTGACTCAGCCACCCTCAGTGTCTGGGACCCCCGGGCAGAGTGTCACCA
TCTCTTGTTCTGGGAGCAACTCCAACCTCGGATCTAATTATGTGTACTGGTACCAGGTGGTCC
CAGGCACGGCCCCCAAACTCGTCATCTATA*GAAATAAATAT*CGGCCCCCAGGGGTCCCTGACC
GATTCTCTGGCTCCAAGTCTGGCACCTCAGCCTCCCTGGCCATCAGTGGGCTCCGGTCCGACG
ATGAGGCTGAATATTATTGTTCCGGATGGGATGACAGCCTGAGTGGTCGACTATTCGGCGGAG
GGACCAAG SEQ ID NO: 70: Light Chain Variable Domain Nucleic Acid Sequence of 2F1
GATGTTGTGATGACTCAGTCTCCGCTCTTCCTGCCCGTCACCCCTGGACAGCCGGCCT
CCATCTCCTGCAGGTCTAGTCAAAGCCTCGTATACAGTGATGGAAACACCTACTTGAGTTGGT
TTCAGCAGAGGCCAGGCCAATCTCCAAGGCGCCTAGTTTATA*AGGTTTCTAGCCGGGACTCTG*
GGGTCCCAGACAGATTCAGCGGCAGTGGGTCAGGCACTGATTTCACACTGAAAATCAGCAGGG
TGGAGGCTGAGGATGTTGGGGTTTATTACTGCATGCAAGGTACACACTGGCCTCGGACGTTCG
GCCAAGGGACCAAG SEQ ID NO: 72: Light Chain Variable Domain Nucleic Acid Sequence of 3C6
AATTTTATGCTGACTCAGCCCCACTCTGTGTCGGAGTCTCCGGGGAAGACGGTTACCA
TCTCCTGCACCGGCAGCAGTGGCAGCATTGCCAGCAACTATGTGCAGTGGTACCAGCAGCGCC
CGGGCAGTGTCCCCACCACTGTGATCTAT*GAGGATAACCAAAGACCC*TCTGGGGTCCCTGATC
GGTTCTCTGGCTCCATCGACAGCTCCTCCAACTCTGCCTCCCTCACCATCTCTGGACTGAAGA
CTGAGGACGAGGCTGACTACTACTGTCAGTCTTTTGATAGCAGCAATTATTGGGTGTTCGGCG
GAGGGACCAAG SEQ ID NO: 74: Light Chain Vari-
able Domain Nucleic Acid Sequence of 3D12
GACATCCAGATGACCCAGTCTCCATCCTCCCTGTCTGCATCTGTAGGAGACAGAGTCA
CCATCACTTGCCGGGCAAGTCAGAACATTAGCAGCTATTTAAATTGGTATCAGCAGAAACCAG
GGAAAGCCCCTAAGCTCCTGATCTAT*GCTGCATCCAGTTTGCAAAGT*GGAGTCCCATCAAGGT
TCAGTGGCAGTGGATCTGGGACAGATTTCATTCTCACCATCAGCAGTCTGCAACCTGAAGATT
TTGCAACTTACTACTGTCAACAGAGTTACAGTACCCCCCCCACCTTCGGCCAAGGGACACGA SEQ ID NO: 76: Light Chain Variable Domain Nucleic Acid Sequence of 3A9
GAAACGACACTCACGCAGTCTCCAGGCACCCTGTCTTTGTCTCCAGGGGAAAGAGCCA
CCCTCTCCTGCAGGGCCAGTCAGAGTGTTAGCAGCAGCTACTTAGCCTGGTACCAGCAGAAAC
CTGGCCAGGCTCCCAGGCTCCTCATCTAT*GGTGCATCCAGAAGGGCC*ACTGGCATCCCAGACA
GGTTCAGCGGCAGTGGGTCTGGGACAGACTTCACTCTCACCATCAGCAGACTGGAGCCTGAAG
ATTTTGCAGTGTATTACTGTCAGCAGTATGGTAGCTCACCGATCACCTTCGGCCAAGGGACAC
GA SEQ ID NO: 78: Light Chain Variable Domain Nucleic Acid Sequence of 1F4
GAAACGACACTCACGCAGTCTCCAGGCACCCTGTCTTTGTCTCCAGGGGAAAGAGCCA
CCCTCTCCTGCAGGGCCAGTCAGAGTGTTAGCAGCACCTACTTAGCCTGGTACCAGCAGAAAC
CTGGCCAGGCTCCCAGGCTCCTCATTTAC*GGTGCATCCAGGCGGGCC*ACTGGCTCCCCAGAGA TABLE D2-continued Heavy Chain and Light Chain Nucleic Acid Sequence ID Numbers
(sequences set out below)

GGTTCAGTGGCGGTGGGTCTGGGACAGACTTCACTCTCACCATCAGTAGACTGGAGCCCGAAG
ATTTCGCAGTCTATTACTGTCAACATTATGGTAACTCACCGGGGACGTTCGGCCAAGGGACCA
AG

SEQ ID NO: 80: Light Chain Vari-
able Domain Nucleic Acid Sequence of 1H10
GAAATTGTGCTGACTCAGTCTCCAGGCACCCTGTCTTTGTCTCCAGGGGAAAGAGCCA
CCCTCTCCTGCAGGGCCAGTCAGAGTGTTAGCAGCAGCTACTTAGCCTGGTACCAGCAGAAAC
CTGGCCAGGCTCCCAGGCTCCTCATCTAT*GATGCATCCAACAGGGCC*ACTGGCATCCCAGCCA
GGTTCAGTGGCAGTGGGTCTGGGACAGACTTCACTCTCACCATCAGCAGCCTAGAGCCTGAAG
ATTTTGCAGTTTATTACTGTCAGCAGCGTAGCAACTGGCCCCCGAGGGCCACCTTCGGCCAAG
GGACACGA SEQ ID NO: 82: Light Chain Vari-
able Domain Nucleic Acid Sequence of 3C12
CAGTCTGTGCTGACTCAGCCACCCTCGGCGTCAGTGGCCCCAGGAAAGACGGCCAGGA
TTACCTGTGGGGGAAACAACATTGGAAGTAAAAGTGTGCACTGGTACCAGCAGAAGCCAGGCC
AGTCCCCTGTGCTGGTCATCTAT*CAAGATACCAAGCGGCCCT*CAGGGATCCCTGAGCGATTCT
CTGGCTCCAACTCTGGGAACACAGCCACTCTGACCATCAGCGGAGCCCAGCCTATGGATGAGG
CTGACTATTACTGTCAGGCGTGGTACAGCACCATTATGGTATTTGGCGGAGGGACCAAG SEQ ID NO: 84: Light Chain Vari-
able Domain Nucleic Acid Sequence of 4G11
GAAATTGTGCTGACTCAGTCTCCAGGCACCCTGTCTTTGTCTCCAGGGGAAAGAGCCA
CCCTCTCCTGCAGGGCCAGTCAGAGTGTTAGCAGCAGCTACTTAGCCTGGTACCAGCAGAAAC
CTGGCCAGGCTCCCAGGCTCCTCATCTAT*GGTGCATCCAGCAGGGCC*ACTGGCATCCCAGACA
GGTTCAGTGGCGGTGGGTCTGGGACAGACTTCACTCTCACCATCAGCAGACTGGAGCCTGAAG
ATTCTGCAGTGTATTACTGTCAGCAATATGATCATTCACCCACTTTTGGCCAGGGGACCAAG SEQ ID NO: 86: Light Chain Vari-
able Domain Nucleic Acid Sequence of 4A12
CTGCCTGTGCTGACTCAGCCCCCCTCAGTGTCCGTGTCCCCAGGACAGACAGCCAGGA
TCACCTGCTCTGGATATGAATTGGGGGATAAATATGCTTTCTGGTATCAGCAGAAGCCAGGCC
AGTCCCCTGTTCTGGTCATTTAT*CAAGATACCAAGCGGCCCT*CAGGGATCCCTGAGCGATTCT
CTGGCTCCAGCTCTGGGGACACAGCCACTCTGATCATCAGCGGGACCCAAATTTTGGATGAGG
CTGACTATTACTGTCAGGCGTGGGACAGCAGCACCCATGTGGTATTCGGCGGAGGGACCAAG SEQ ID NO: 88: Light Chain Vari-
able Domain Nucleic Acid Sequence of 1A12
GAAACGACACTCACGCAGTCTCCAGGCACCCTGTCTTTGTCTCCAGGGGAAAGAGCCA
CCCTCTCCTGCAGGGCCAGTCAGAGTATTAGCAGCATCTACTTAGCCTGGTACCAGCAGAAAC
CTGGCCAGGCTCCCAGGCTCCTCATTTAT*GGTGCATCCAGGAGGGCC*ACTGGCATCCCAGACA
GGTTCAGTGGCAGTGGGTCTGGGACAGACTTCACTCTCACCATCAGCAGACTGGAGCCTGAAG
ATTTTGCAGTGTATTACTGTCAGCAGTATGGTAGCTCACTTCGGACGTTCGGCCAAGGGACCA
AG SEQ ID NO: 90: Light Chain Vari-
able Domain Nucleic Acid Sequence of 3G12
GAAACGACACTCACGCAGTCTCCAGGCACCCTGTCTTTGTCTCCAGGGGAAAGAGCCA
CCCTCTCCTGCAGGGCCAGTCAGAGTGTTAGCAGCAGCTACTTAGCCTGGTACCAGCAGAAAC
GTGGCCAGGCTCCCAGGCTCCTCATCTAT*GGTGCATCCCGCAGGGCC*ACTGGCATCCCAGACA
GGTTCAGTGGCAGTGGGTCTGGGTCAGACTTCACTCTCACCATCAGCAGACTGGAGCCTGAAG
ATTTTGCAGTGTATTACTGTCAGCAGTATGGTAGCTCACCCTCGACGTTCGGCCAAGGGACCA
AG SEQ ID NO: 92: Light Chain Variable Domain Nucleic Acid Sequence of 4F9
GATGTTGTGATGACTCAGTCTCCACTCTCCCTGCCCGTCACCCCTGGAGAGTCGGCCT
CCATCTCCTGCAGGTCTAGTCAGAGCCTCCTGCATAGTAATGGATACAACTATTTGGATTGGT
ACCTGCAGAAGCCAGGGCAGTCTCCACAGCTCCTGATCTATT*TGGGTTCTAATCGGGCCT*CCG
GGGTCCCTGACAGGTTCAGTGGCAGTGGATCAGGCACAGATTTTACACTGAAAATCAGCAGAG
TGGGGGCTGAGGATGTTGGGGTTTATTACTGTATGCAAGTTCTACAAACTCCCTGGACGTTCG
GCCAAGGGACCAAA SEQ ID NO: 94: Light Chain Variable Domain Nucleic Acid Sequence of 4G4
GAAACGACACTCACGCAGTCTCCAGGCACCCTGTCTTTGTCTCCAGGGGAAAGAGCCA
CCCTCTCCTGCAGGGCCAGTCAGAGTGTTAGCAGCAGCTACTTAGCCTGGTATCAACAAAAC
CTGGCCAGGCTCCCAGGCTCCTCATCTAT*AATGCGTCCAGGAGGGCC*ACTGGCATCCCAGACA
GGTTCAGTGGCAGTGGGTCTGGGGCAGACTTCACTCTCACCATCAGCAGACTGGATCCTGAAG
ATTTTGCAGTGTATTTCTGTCAGCAGTATGGTAGCTCACCTCAGACGTTCGGCCAAGGGACCA
AG SEQ ID NO: 96: Light Chain Variable Domain Nucleic Acid Sequence of 1E1
GTAACGACACTCACGCAGTCTCCAGGCACCCTGTCTTTGTCTCCAGGGGAAAGAGCCA
CCCTCTCCTGCAGGGCCAGTGAGAGTGTTAGCAGCAGGTACTTAGCCTGGTACCAGCAGAGAC
CTGGCCAGGCTCCCAGGCTCCTCATTTAC*GGTGCATCCAGGCGGGCC*ACTGGCTCCCCAGAGA TABLE D2-continued Heavy Chain and Light Chain Nucleic Acid Sequence ID Numbers
(sequences set out below)

GGTTCAGTGGCGGTGGGTCTGGGACAGACTTCACTCTCACCATCAGTAGACTGGAGCCCGAAG
ATTTCGCAGTCTATTACTGTCAACATTATGGTAACTCACCGGGGACGTTCGGCCAAGGGACCA
AG

Example 8. Use as Anti-GPC-3 Bi-Specific T Cell-Engaging Antibodies

The anti-GPC-3 antibodies were used to construct anti-GPC-3 bi-specific T cell-engaging antibodies. In these constructs, the Fab region of one arm from each of the 5 anti-GPC-3 antibody clones (1C4, 1D2, 2B5, 4H1, 5C4) was replaced by the anti-CD3 scFv fragment, as shown below.

| Clone | Heavy Chain (V$_H$) Amino Acid Sequence | Light Chain (V$_L$) Amino Acid Sequence |
|---|---|---|
| Anti-CD3 | SEQ ID NO: 97 | SEQ ID NO: 98 |

TABLE D3

Anti-CD3 Heavy Chain and Light Chain Amino Acid Sequence ID Numbers (sequences set out below)

ANTI-CD3 HEAVY CHAIN VARIABLE DOMAIN AMINO ACID SEQUENCE (V$_H$)

SEQ ID NO: 97: Heavy Chain Variable Domain Amino Acid Sequence of Anti-CD3
DVQLVQSGAEVKKPGASVKVSCKASGYTFTRYTMHWVRQAPGQGLEWIGY
INPSRGYTNYADSVKGRFTITTDKSTSTAYMELSSLRSEDTATYYCARYY
DDHYCLDYWGQGTTVTVSS

ANTI-CD3 LIGHT CHAIN VARIABLE DOMAIN AMINO ACID SEQUENCE (V$_L$)

SEQ ID NO: 98: Light Chain Variable Domain Amino Acid Sequence of Anti-CD3
DIVLTQSPATLSLSPGERATLSCRASQSVSYMNWYQQKPGKAPKRWIYDT
SKVASGVPARFSGSGSGTDYSLTINSLEAEDAATYYCQQWSSNPLTFGGG
TKVEIK

| Clone | Heavy Chain (V$_H$) Nucleic Acid Sequence | Light Chain (V$_L$) Nucleic Acid Sequence |
|---|---|---|
| Anti-CD3 | SEQ ID NO: 99 | SEQ ID NO: 100 |

TABLE D4

Anti-CD3 Heavy Chain and Light Chain Nucleic Acid Sequence ID Numbers (sequences set out below)

ANTI-CD3 HEAVY CHAIN VARIABLE DOMAIN NUCLEIC ACID SEQUENCE (V$_H$)

SEQ ID NO: 99: Heavy Chain Variable Domain Nucleic Acid Sequence of Anti-CD3
gatgtgcagctggtgcagagcggggcagaggtgaaaaagcctggggcaag
cgtcaaagtcagttgtaaagcctccggctacacattcactaggtatacta
tgcactgggtgcgccaggcccctggccaggggctggagtggatcggctac
attaacccaagcagagggtacacaaattatgctgactccgtgaaaggcag
gtttactatcaccaccgataagtccacctctacagcatacatggagctga TABLE D4-continued Anti-CD3 Heavy Chain and Light Chain Nucleic Acid Sequence ID Numbers (sequences set out below)

gcagcctgcgaagcgaagacactgcaacctactattgcgccggtactat
gacgatcattactgtctggattattggggacagggcactaccgtgacagt
ctctagt

ANTI-CD3 LIGHT CHAIN VARIABLE DOMAIN NUCLEIC ACID SEQUENCE (V$_L$)

SEQ ID NO: 100: Heavy Chain Variable Domain Nucleic Acid Sequence of Anti-CD3
Gatattgtgctgacccagtctccagccacactgagtctgtcacccggcga
acgagccaccctgagctgccgggccagccagtccgtctcttacatgaact
ggtatcagcagaagcccggaaaagcccctaagcggtggatctacgacaca
agcaaagtggcttccggcgtccccgcacgattcagtggctcagggagcgg
aactgactattctctgaccattaatagtctggaggctgaagatgccgcta
cctactattgtcagcagtggtcaagcaaccctctgacattcggggggga
actaaagtggaaatcaag

ANTI-CD3 SCFV AMINO ACID SEQUENCE

SEQ ID NO: 101: Amino Acid Sequence of Anti-CD3 scFv
DVQLVQSGAEVKKPGASVKVSCKASGYTFTRYTMHWVRQAPGQGLEWIGY
INPSRGYTNYADSVKGRFTITTDKSTSTAYMELSSLRSEDTATYYCARYY
DDHYCLDYWGQGTTVTVSSGEGTSTGSGGSGGSGGADDIVLTQSPATLSL
SPGERATLSCRASQSVSYMNWYQQKPGKAPKRWIYDTSKVASGVPARFSG
SGSGTDYSLTINSLEAEDAATYYCQQWSSNPLTFGGGTKVEIK

ANTI-CD3 SCFV NUCLEIC ACID SEQUENCE

Figure 8:
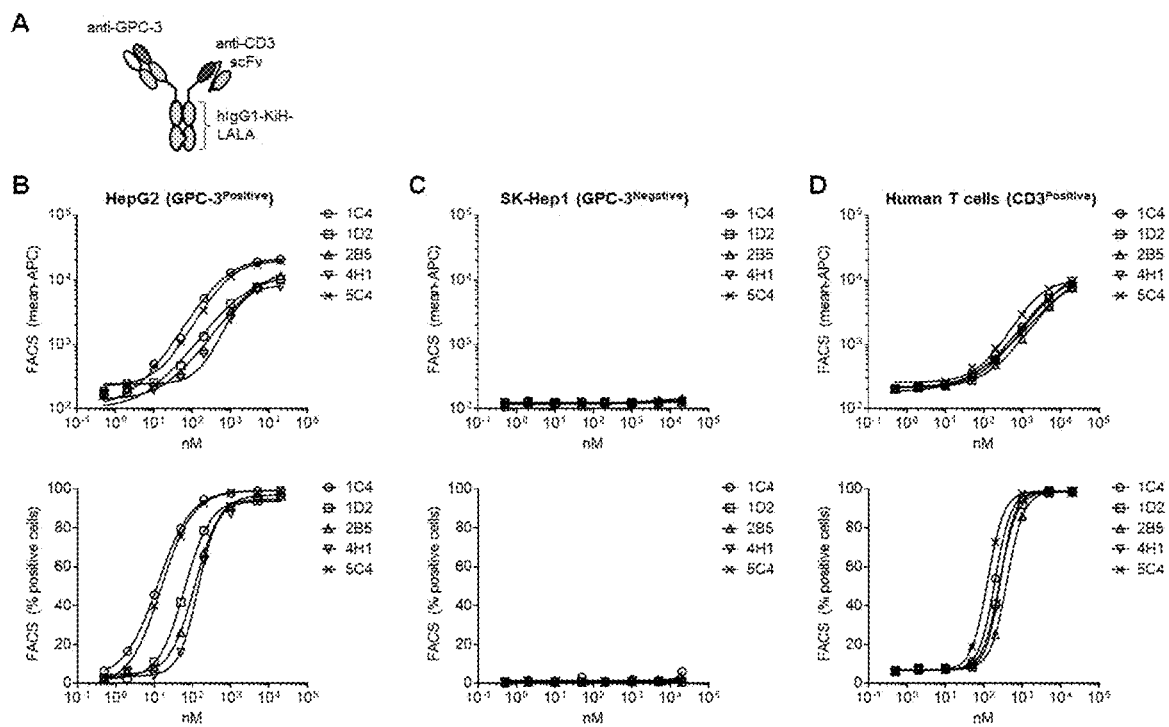
Fig. 8A is a drawing of an anti-GPC-3 bi-specific T cell-engaging antibody.
FIGS. 8B to 8D are drawings showing binding curves of 5 anti-GPC-3 bi-specific T cell-engaging antibodies to (FIG. 8B) GPC-3$^{Positive}$ HepG2 cells, (FIG. 8C) GPC-3$^{Negative}$ SK-Hep1 cells and (FIG. 8D) CD3$^{Positive}$ human T cells at different antibody concentrations. Top panels show the mean fluorescence intensity of anti-GPC-3 bi-specific T cell-engaging antibodies binding to different cells, while bottom panels show the percentage of cells positively stained by the anti-GPC-3 bi-specific T cell-engaging antibodies.

SEQ ID NO: 102: Nucleic Acid Sequence of Anti-CD3 scFv
gatgtgcagctggtgcagagcggggcagaggtgaaaaagcctggggcaag
cgtcaaagtcagttgtaaagcctccggctacacattcactaggtatacta
tgcactgggtgcgccaggcccctggccaggggctggagtggatcggctac
attaacccaagcagagggtacacaaattatgctgactccgtgaaaggcag
gtttactatcaccaccgataagtccacctctacagcatacatggagctga
gcagcctgcgaagcgaagacactgcaacctactattgcgccggtactat
gacgatcattactgtctggattattggggacagggcactaccgtgacagt
ctctagtgggagggaacatccactgggtctggagggagtggaggctcag
gaggagcagacgatattgtgctgacccagtctccagccacactgagtctg
tcacccggcgaacgagccaccctgagctgccgggccagccagtccgtctc
ttacatgaactggtatcagcagaagcccggaaaagcccctaagcggtgga
tctacgacacaagcaaagtggcttccggcgtccccgcacgattcagtggc
tcagggagcggaactgactattctctgaccattaatagtctggaggctga
agatgccgctacctactattgtcagcagtggtcaagcaaccctctgacat
tcggggggggaactaaagtggaaatcaag Knob-in-hole mutations were introduced to facilitate correct heavy-chain pairing and LALA mutations to remove Fcγ receptor binding (FIG. 8A).

The ability of these anti-GPC-3 bi-specific T cell-engaging antibodies to specifically recognize and bind to both GPC-3 and human CD3 molecules on cell surface was measured using HepG2 (GPC-3$^{Positive}$), SK-Hep1 (GPC-3$^{Negative}$) and human T cells (CD3$^{Negative}$) cells. HepG2 cells and human T cells constitutively express high level of GPC-3 and CD3, respectively, while SK-Hep1 cells do not express GPC-3 or CD3.

Briefly, HepG2 (GPC-3$^{Positive}$), SK-Hep1 (GPC-3$^{Negative}$) and human T cells (CD3$^{Positive}$) were seeded in cell suspension at 100000 per well in 96-well round-bottom plate prior to incubation with different concentrations of anti-GPC-3 bi-specific T cell-engaging antibodies. Binding was measured by flow cytometry using a secondary labelled antibody. In this assay, all 5 anti-GPC-3 bi-specific T-cell engaging antibodies bound strongly to the GPC-3 expressing cell HepG2 (FIG. 8B) as well as human T cells expressing CD3 (FIG. 8D). However, these antibodies did not bind to GPC-3 negative SK-Hep1 cells (FIG. 8C). This suggests that these anti-GPC-3 bi-specific T cell-engaging antibodies bind to surface of the cells in a highly specific manner dependent on GPC-3 and CD3 expression.

To assess the function of these anti-GPC-3 bi-specific T-cell engaging antibodies, T cells from healthy donors were isolated and incubated with either HepG2 (GPC-3$^{Positive}$) or SK-Hep1 (GPC-3$^{Negative}$) cells in the presence of anti-GPC-3 bi-specific T-cell engaging antibodies at 3 different concentrations of 2.5 nM, 312.5 pM and 39 pM. 24 hours later, T cells were harvested and analysed for their activation status by assessing the surface expression of T cell activation markers CD25 and CD69.

Figure 9:
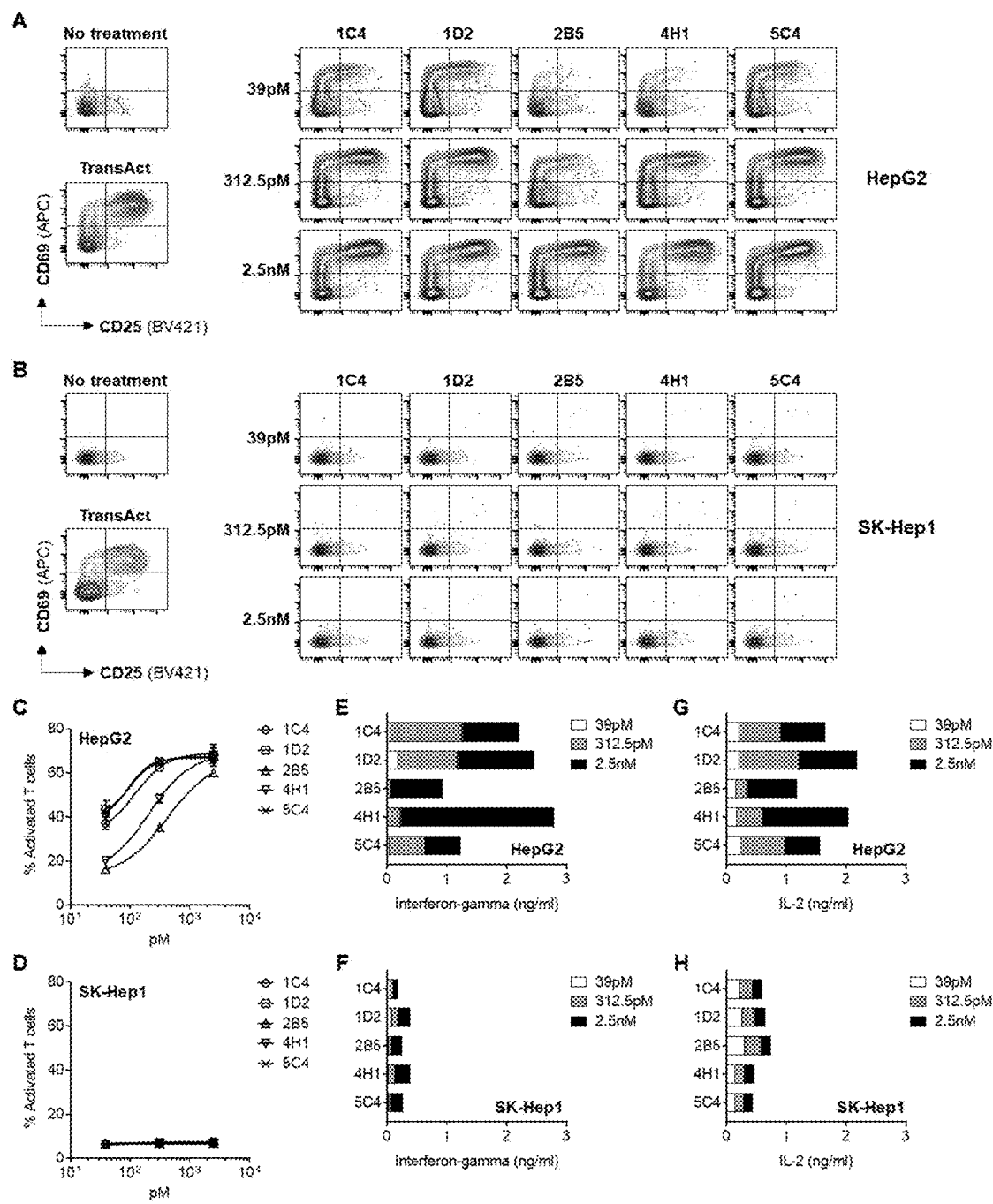
FIGS. 9A to 9H are drawings showing anti-GPC-3 bi-specific T cell-engaging antibodies activate human T cells when co-cultured with GPC-3$^{Positive}$ HepG2 cells. 24 hours post co-culture of naïve human T cells with either (FIG. 9A) HepG2 cells or (FIG. 9B) SK-Hep1 cells in the presence of different anti-GPC-3 bi-specific T cell-engaging antibodies at 3 different concentrations, T cells were harvested and stained with antibodies against T cell activation marker CD25 and CD69 for flow cytometry analysis. T cells treated with T cell activator, TransAct™ (Miltenyi Biotec), was included as a positive control.

The results showed that all five anti-GPC-3 bi-specific T-cell engaging antibodies could strongly activate human naïve T cells when co-cultured with GPC-3$^{Positive}$ HepG2 cells (FIG. 9A and FIG. 9C) but not with GPC-3$^{Negative}$ SK-Hep1 cells (FIG. 9B and FIG. 9D).

In addition, cell culture supernatants were collected and subjected to ELISA to assess the cytokine release of interferon-γ and IL-2 from anti-GPC-3 bi-specific T-cell engaging antibodies treated T cells.

When co-cultured with GPC-3$^{Positive}$ HepG2 cells in the presence of anti-GPC-3 bi-specific T-cell engaging antibodies (clone 1C4, 1D2, 2B5, 4H1 and 5C4), activated human T cells secreted remarkably higher amount of interferon-γ and IL-2 (FIG. 9E and FIG. 9G). However, release of interferon-γ and IL-2 remained low when co-cultured with GPC-3$^{Negative}$ SK-Hep1 cells (FIG. 9F and FIG. 9H), indicating the superior specificity of these anti-GPC-3 bi-specific T-cell engaging antibodies.

Efficacy of these anti-GPC-3 bi-specific T-cell engaging antibodies was further examined by subjecting them to the antibody dependent T cell mediated cytotoxicity assay.

Briefly, GPC-3$^{Positive}$ HepG2 cells (T: Target cells) were seeded onto the xCelligence E-plate and cultured for overnight with cell index values measured. The next day, immediately after addition of anti-GPC-3 bi-specific T-cell engaging antibodies at various concentrations, primary T cells isolated from human PBMCs (E: Effector cells) were added to the target cells at Effector to Target ratio of 4 to 1 (E:T=4:1). The assay was continued for a further 72 hours to measure the target cell index values using xCelligence RTCA system.

Figure 10:
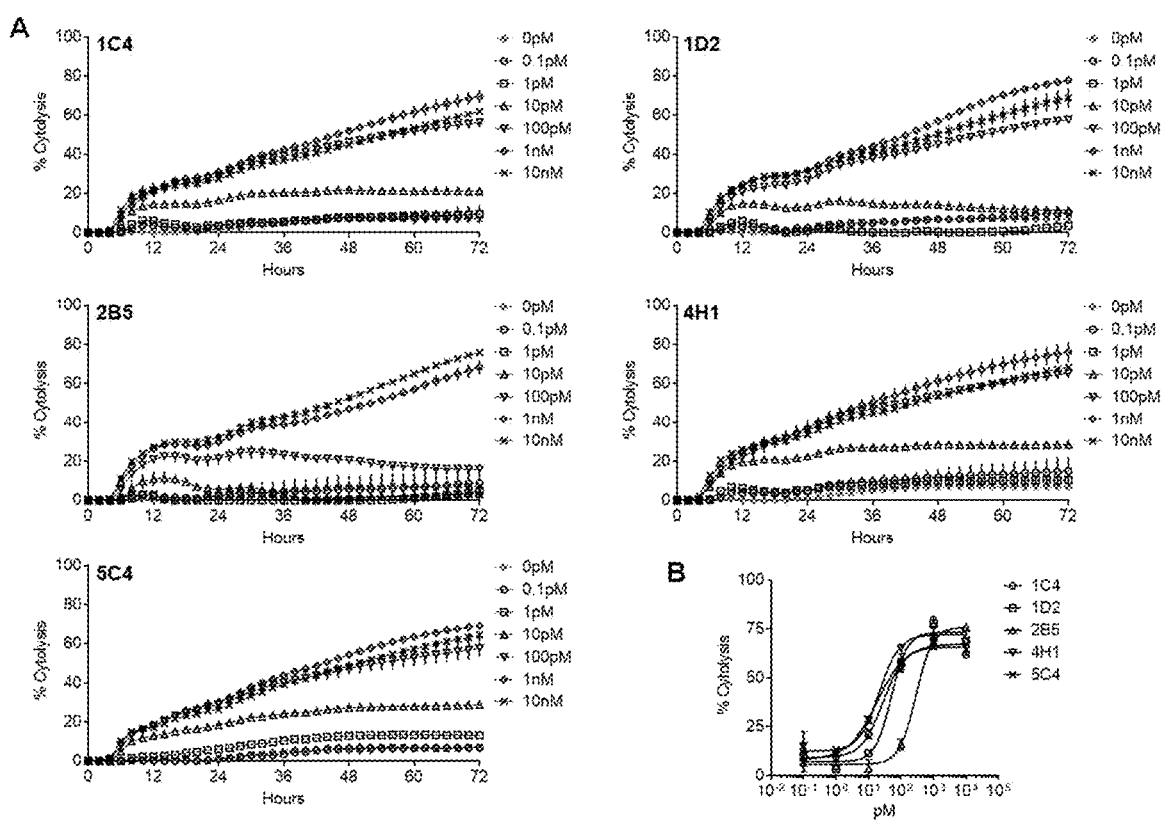
FIGS. 10A and 10B are drawings showing T cell mediated cytotoxicity of GPC-3$^{Positive}$ HepG2 cells by anti-GPC-3 bi-specific T cell-engaging antibodies.

Except for clone 2B5, which only induce profound cytolysis of target cell HepG2 (GPC-3$^{Positive}$) at high concentration of 10 nM and 1 nM, all the other anti-GPC-3 bi-specific T-cell engaging antibodies (clone 1C4, 1D2, 4H1 and 5C4) were able to kill 50-70% of HepG2 cells within 72 hours at a concentration as low as 0.1 nM (FIG. 10A and FIG. 10B).

In summary, results from the above assays showcased the use of our anti-GPC-3 antibodies in the format of bi-specific T cell engaging antibody with high specificity and potency in inducing cell death of GPC-3 expressing cells.

Example 9. Use in a Chimeric Antigen Receptor (CAR) T Cell Construct

Figure 11:
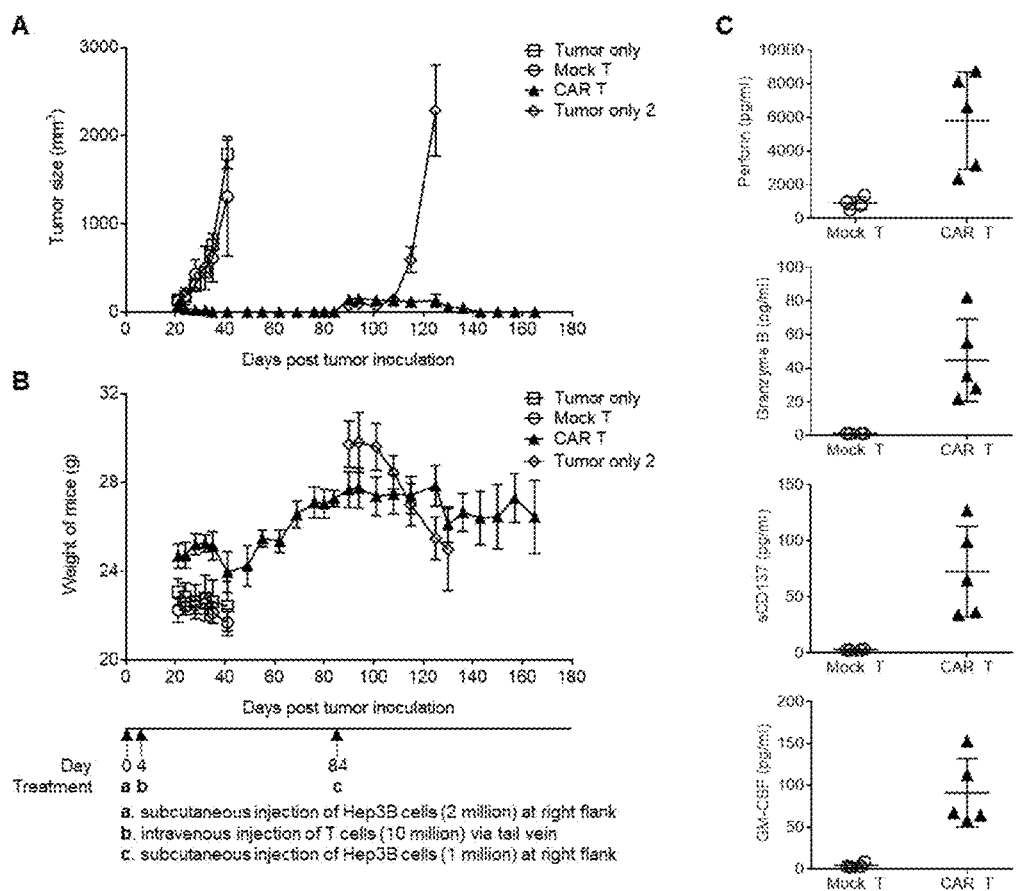
FIGS. 11A to 11C are drawings showing that anti-GPC-3 CAR T cells prevented GPC-3$^{Positive}$ HCC tumor formation in xenograft models. Two million of GPC-3$^{Positive}$ Hep3B cells were subcutaneously injected into the right flanks of NSG mice. Four days later, mice were randomly grouped (4-5 mice per group) and ten million of anti-GPC-3 CAR T cells (clone 5C4 scFv) or Mock T cells were intravenously injected into these mice via tail vein. Eighty-four days post initial tumor inoculation, all tumor-free mice from the CAR T group were re-challenged with one million of Hep3B cells via subcutaneous injection. Tumor size (FIG. 11A) and weight of each mouse (FIG. 11B) were measured and recorded every 3-7 days.

The in vivo activity of anti-GPC-3 CAR T cells was first assessed with a preventive model using immunocompromised NSG (NOD-scid IL2Rgamma$^{null}$) mice (FIG. 11).

On day 0, two million Hep3B cells were subcutaneously injected into the right flanks of NSG mice (female only). Four days later when there is no measurable tumor observed, mice were randomly grouped and injected with ten million of either anti-GPC-3 CAR T cells (clone 5C4) or Mock T cells. All mice from both "Tumor only" group (no T cells injected) and "Mock T" group developed big tumors and were sacrificed on day 41, whereas all mice from "CAR T" group remained tumor-free. Eighty-four days post initial tumor inoculation, all tumor-free mice from the CAR T group (4 mice) together with a group of naïve mice (5 mice, "Tumor only 2") were challenged with one million of Hep3B cells subcutaneously injected into the right flanks and their tumor growth and body weights were continuously monitored. While all five mice from "Tumor only 2" group developed into sizable tumors, two mice from CAR T group remained tumor free until day 165 (81 days post re-challenge) (FIG. 11A).

These data indicated that 5C4 CAR T cells prevented GPC-3$^{Positive}$ HCC tumor formation in xenograft models and also provided long-term protection to the NSG mice from developing GPC-3$^{Positive}$ HCC tumors upon tumor re-challenge. In addition, the anti-GPC-3 CAR T cells (clone 5C4) did not induce severe toxicity to the NSG mice as there was no significant drop in mouse body weight upon anti-GPC-3 CAR T treatment (FIG. 11B). The efficacy of the anti-GPC-3 CAR T cells was also reflected by the up-regulated blood serum level of T cell associated cytokines (Perforin, Granzyme B, sCD137, GM-CSF) from the "CAR T" group compared to the basal levels detected from the "Mock T" group after 6 days of T cell injection (FIG. 11C).

To test if the anti-GPC-3 CAR T cells are capable to suppress the growth of established tumors in vivo, we chose 3 different anti-GPC-3 antibody clones to generate anti-GPC-3 CAR constructs (clone 1D2, 4H1, and 5C4). Regardless of different clones, 20% of CAR expression was achieved by lentivirus transduction (FIG. 12A).

Figure 12:
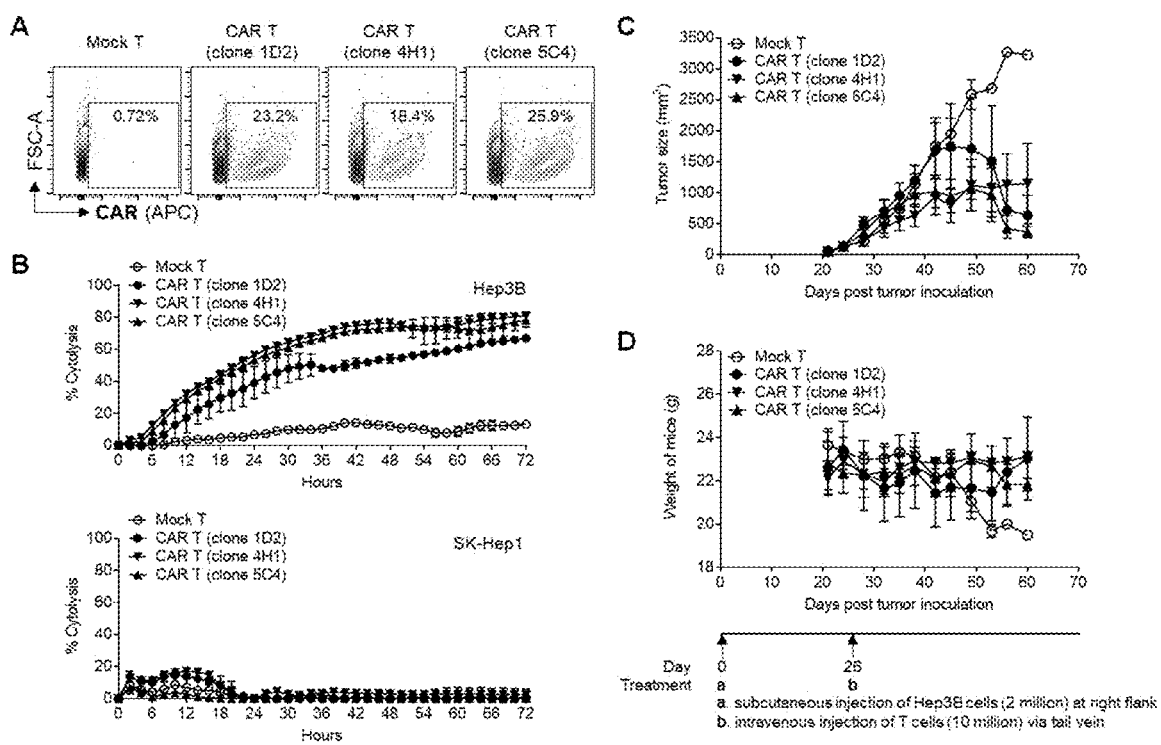
FIGS. 12A to 12D are drawings showing that anti-GPC-3 CAR T cells suppressed the growth of Hep3B xenografts in vivo.

These anti-GPC-3 CAR T cells exhibited strong and specific in vitro target cell cytotoxicity as they killed 70-80% of GPC-3$^{Positive}$ Hep3B cells but not GPC-3$^{Negative}$ SK-Hep1 cells in an xCelligence cell impedance assay (FIG. 12B). Twenty-six days after subcutaneously inoculation of NSG mice (female only) with 2 million of GPC-3$^{Positive}$ Hep3B cells, the mice were grouped according to the measurable tumor size for CAR T cell injection. Ten million of different anti-GPC-3 CAR T cells (4 mice per group) or Mock T cells (3 mice) were intravenously injected into these mice via tail vein On day 45 (19 days post CAR T cell injection), tumors in the mice treated with 1D2 CAR T cells at an average size of 1749 mm$^3$ started to shrink, to an average of 643 mm$^3$ on day 60. Tumors in the mice treated with 4H1 CAR T cells or with 5C4 CAR T cells grew much slower than Mock T treated mice and a further decrease in tumor size was observed for 5C4 CAR T group from Day 53 onwards (FIG. 12C).

Interestingly, while the body weights of Mock T group of mice dropped significantly after 45 days of tumor inoculation when average tumor size exceeded 2000 mm$^3$, the body weights of all CAR T injected mice remained stable (FIG. 12D).

These data suggested that our anti-GPC-3 CAR T cells potently suppressed growth of GPC-3$^{Positive}$ HCC xenograft in vivo without inducing severe toxicity.

Next, we aimed to test if our anti-GPC-3 CAR T cell therapy is effective with a combinatorial use of immune checkpoint blockade antibodies, such as anti-PD1 antibodies.

Similarly, two million Hep3B cells were subcutaneously injected into the right flank of NSG mice (female only). Twenty-four days later, mice were grouped according to the measurable tumor size and injected intravenously with either anti-GPC-3 CAR T cells (clone 5C4) or Mock T cells via tail vein. Ten days after CAR T cell injection when both groups developed tumors exceeding an average size of 1000 mm$^3$, all mice were intraperitoneal injected with anti-PD1 IgG$_4$ antibodies for a total of 5 times with an interval of 3 to 5 days.

Mock T group of mice did not respond to anti-PD1 antibodies, and as a result tumors continued to grow. In contrast, within 5 days of the Pt anti-PD1 antibody injection, tumors from the CAR T group of mice exhibited a sharp drop in size and continued to shrink until the average tumor size reached less than 100 mm$^3$ and lasted for more than 20 days (FIG. 13A).

The body weight from both Mock T and CAR T group of mice remained stable though a slight fluctuation was observed in CAR T group (FIG. 13B).

As a result of the potent tumor suppression by combinatorial use of anti-GPC-3 CAR T and anti-PD1 antibodies, 75% of mice treated with the anti-GPC-3 CAR T cells followed by anti-PD1 antibodies survived for longer than 70 days, while the median survival durations of the Mock T followed by anti-PD1 antibodies treated mice were only 45 days (FIG. 13C).

Interestingly, on the day after the second anti-PD1 antibody injection (Day40, 16 days after CAR T cell infusion), the total number of human T cells from mice of the CAR T group was significantly higher than that of mice treated with Mock T cells (FIG. 13D). In addition, the persistence of peripheral CAR+CD3+ T cells, CD4+CD3+ T cells, and CD8+CD3+ T cells was consistent with the total T cells (FIG. 13E). Moreover, the efficacy of the combination therapy of anti-GPC-3 CAR T cells and anti-PD1 antibodies was also observed by the up-regulation in blood serum level of T cell associated cytokines (Perforin, Granzyme B, sCD137, GM-CSF) in the anti-GPC-3 CAR T cell treated group (FIG. 13F).

Since most of the anti-GPC-3 antibodies clones can cross-react with the mouse homolog of GPC-3 protein, we injected CAR T cells derived from 8 different mouse cross-reacting anti-GPC-3 clones (1C4, 1D2, 1F1, 1H1, 2B5, 4A5, 4H1, and 5C4) and 1 anti-GPC-3 clone, 1D8, which does not cross-react with mouse GPC-3, into NSG mice (6 mice per group, mixed genders). We tested the potential toxicity of these anti-GPC-3 CAR T cells against the normal mouse tissues in the absence of tumor cells expressing high level of GPC-3 proteins, by monitoring the body weight as well as other abnormal physiological changes or behaviours of each mouse. The results clearly showed that similar to "No treatment" group (FIG. 14A), Mock T group (FIG. 14B), and 1D8 CAR T group (FIG. 14E), the 8 different anti-GPC-3 CAR T cells which could bind to mouse GPC-3 expressing cells, did not induce noticeable toxicity in vivo up to the time point of 5 weeks (FIG. 14C, FIG. 14D, FIG. 14F, FIG. 14G, FIG. 14H, FIG. 14I, FIG. 14J and FIG. 14K), beyond which GvHD may happen anytime.

This indicated that either mouse GPC-3 did not express in normal mouse tissues, or the affinities between the mouse GPC-3 protein and the scFv fragment derived from the 8 anti-GPC-3 clones were at an optimal level that the low expression of mouse GPC-3 on normal mouse tissues would not induce strong activation of these anti-GPC-3 CAR T cells.

Finally, to examine if the use of CAR T cell therapy can be extended to the mouse system, we first stained parental MC38 cells and mouse GPC-3 stably transduced MC38 cells (named as "MC38-mGPC-3") using a representative anti-GPC-3 IgG clone 5C4 followed by flow cytometry analysis (FIG. 15A).

A mouse CAR T construct based on clone 5C4 was designed by replacing the human T cell activation domains to their counterpart of mouse homologs and cloned into a retrovirus-based vector. Anti-GPC-3 mouse CAR T cells were generated from mouse T cells isolated from mouse splenocytes by retroviral transduction process and the mouse CAR expression was detected by flow cytometry analysis (FIG. 15B). The in vitro activity of these mouse CAR T cells was verified by more than 80% cytotoxicity of the MC38-mGPC-3 cells within 96 hours using xCelligence impedance assay (FIG. 15C). To test the in vivo therapeutic efficacy of mouse anti-GPC-3 CAR T cells, 0.8 million MC38-mGPC-3 cells were subcutaneously injected into WT C57BL/6 mice. When the tumors grow to a measurable size (~100 mm$^3$), the mice were re-grouped and intravenously injected with anti-GPC-3 mouse CAR T cells (clone 5C4) or Mock T cells or left untreated ("Tumor only").

By day 33 (21 days post CAR T cell infusion), all mice from both Mock T group and Tumor only group developed big sizes of tumors, while mice from anti-GPC-3 mouse CAR T cell injected group grew very small tumors with 1 mouse remained tumor-free (FIG. 15D). Monitoring of mouse body weights revealed that these mouse CAR T cells did not induce noticeable toxicity both in the presence (FIG. 15E) or in the absence of MC38-mGPC-3 tumor cells expressing mGPC-3 protein (FIG. 15F).

These experiments not only demonstrated the efficacy of mouse anti-GPC-3 CAR T cells both in vitro and in vivo, but also shed light on the extended use of the anti-GPC-3 antibody sequences for future research of anti-GPC-3 CAR T therapy in syngeneic mouse models, as a format of mouse CAR T construct.

Example 10. Binding Affinity of Anti-GPC-3 IgG$_1$ Antibodies

Affinity of 24 anti-GPC-3 IgG$_1$ antibodies was measured via Surface Plasmon Resonance (SPR) analysis using Biacore™ T200 system and shown in Table E3 (below).

TABLE E3

| Clone | $K_D$ (nM) | Ka (1/Ms) | Kd (1/s) |
|---|---|---|---|
| 1A12 | 27.64 | $1.141 \times 10^5$ | $3.155 \times 10^{-3}$ |
| 1C4 | 14.08 | $9.49 \times 10^5$ | $1.336 \times 10^{-2}$ |
| 1D2 | 4.177 | $6.147 \times 10^5$ | $2.567 \times 10^{-3}$ |
| 1D3 | 17.21 | $1.704 \times 10^5$ | $2.932 \times 10^{-3}$ |
| 1D8 | 13.65 | $3.880 \times 10^5$ | $5.295 \times 10^{-3}$ |
| 1E1 | 16.16 | $1.445 \times 10^5$ | $2.334 \times 10^{-3}$ |
| 1F1 | 13.85 | $3.986 \times 10^5$ | $5.520 \times 10^{-3}$ |
| 1F4 | 7.201 | $1.793 \times 10^5$ | $1.291 \times 10^{-3}$ |
| 1H1 | 33.87 | $1.758 \times 10^5$ | $5.955 \times 10^{-3}$ |
| 1H10 | 19.67 | $7.480 \times 10^5$ | $1.467 \times 10^{-2}$ |
| 2B5 | 12.45 | $3.056 \times 10^5$ | $3.804 \times 10^{-3}$ |
| 2F1 | 14.69 | $1.235 \times 10^5$ | $1.814 \times 10^{-3}$ |
| 3A9 | 12.4 | $1.513 \times 10^5$ | $1.876 \times 10^{-3}$ |
| 3C6 | 8.176 | $5.774 \times 10^4$ | $4.721 \times 10^{-4}$ |
| 3C12 | 31.22 | $2.509 \times 10^5$ | $7.835 \times 10^{-3}$ |
| 3D12 | 32.4 | $1.081 \times 10^5$ | $3.501 \times 10^{-3}$ |
| 3G12 | 12.54 | $1.347 \times 10^5$ | $1.688 \times 10^{-3}$ |
| 4A5 | 12.5 | $7.569 \times 10^4$ | $9.459 \times 10^{-4}$ |
| 4A12 | 22.87 | $2.664 \times 10^5$ | $6.094 \times 10^{-3}$ |
| 4F9 | 10.49 | $1.644 \times 10^5$ | $1.725 \times 10^{-3}$ |

TABLE E3-continued

| Clone | $K_D$ (nM) | Ka (1/Ms) | Kd (1/s) |
|---|---|---|---|
| 4G4 | 12.94 | $1.508 \times 10^5$ | $1.952 \times 10^{-3}$ |
| 4G11 | 15.5 | $1.474 \times 10^5$ | $2.285 \times 10^{-3}$ |
| 4H1 | 44.17 | $3.108 \times 10^5$ | $1.373 \times 10^{-2}$ |
| 5C4 | 9.015 | $1.788 \times 10^5$ | $1.612 \times 10^{-3}$ |

Binding affinity ($K_D$), association rate (Ka) and dissociation rate (Kd) of 24 anti-GPC-3 IgG1 antibodies to human GPC-3 protein measured by SPR analysis.

All 24 antibody clones exhibited binding affinity to the recombinant GPC-3 protein at the nanomolar scales ranging from the lowest affinity at 44.17 nM (clone 4H1) to the highest affinity at 4.177 nM (clone 1D2).

REFERENCES

1. Capurro, M. I., Xu, P., Shi, W., Li, F., Jia, A., Filmus, J. Glypican-3 inhibits Hedgehog signaling during development by competing with Patched for Hedgehog binding. Dev. Cell 14: 700-711, 2008.
2. Filmus, J., Capurro, M., Rast, J. Glypicans Genome Biol. 9: 224, 2008. Note: Electronic Article.
3. Filmus, J., Church, J. G., Buick, R. N. Isolation of a cDNA corresponding to a developmentally regulated transcript in rat intestine. Molec. Cell Biol. 8: 4243-4249, 1988.
4. Filmus, J., Shi, W., Wong, Z. M., Wong, M. J. Identification of a new membrane-bound heparan sulphate proteoglycan. Biochem. J. 311: 561-565, 1995.
5. Hughes-Benzie, R. M., Pilia, G., Xuan, J. Y., Hunter, A. G. W., Chen, E., Golabi, M., Hurst, J. A., Kobori, J., Marymee, K., Pagon, R. A., Punnett, H. H., Schelley, S., Tolmie, J. L., Wohlferd, M. M., Grossman, T., Schlessinger, D., MacKenzie, A. E. Simpson-Golabi-Behmel syndrome: genotype/phenotype analysis of 18 affected males from 7 unrelated families Am. J. Med. Genet. 66: 227-234, 1996.
6. Lindsay, S., Ireland, M., O'Brien, O., Clayton-Smith, J., Hurst, J. A., Mann, J., Cole, T., Sampson, J., Slaney, S., Schlessinger, D., Burn, J., Pilia, G. Large scale deletions in the GPC3 gene may account for a minority of cases of Simpson-Golabi-Behmel syndrome. J. Med. Genet. 34: 480-483, 1997.
7. Maurel, M., Dejeans, N., Taouji, S., Chevet, E., Grosset, C. F. MicroRNA-1291-mediated silencing of IRE1-alpha enhances glypican-3 expression. RNA 19: 778-788, 2013.
8. Penisson-Besnier, I., Lebouvier, T., Moizard, M.-P., Ferre, M., Barth, M., Marc, G., Raynaud, M., Bonneau, D. Carotid artery dissection in an adult with the Simpson-Golabi-Behmel syndrome. Am. J. Med. Genet. 146A: 464-467, 2008.
9. Pilia, G., Hughes-Benzie, R. M., MacKenzie, A., Baybayan, P., Chen, E. Y., Huber, R., Neri, G., Cao, A., Forabosco, A., Schlessinger, D. Mutations in GPC3, a glypican gene, cause the Simpson-Golabi-Behmel overgrowth syndrome. Nature Genet. 12: 241-247, 1996.
10. Rodriguez-Criado, G., Magano, L., Segovia, M., Gurrieri, F., Neri, G., Gonzalez-Meneses, A., Gomez de Terreros, I., Valdez, R., Gracia, R., Lapunzina, P. Clinical and molecular studies on two further families with Simpson-Golabi-Behmel syndrome. Am. J. Med. Genet. 138A: 272-277, 2005.
11. Romanelli, V., Arroyo, I., Rodriguez, J. I., Magano, L., Arias, P., Incera, I., Gracia-Bouthelier, R., Lapunzina, P. Germinal mosaicism in Simpson-Golabi-Behmel syndrome. (Letter) Clin. Genet. 72: 384-386, 2007.
12. Sakazume, S., Okamoto, N., Yamamoto, T., Kurosawa, K., Numabe, H., Ohashi, Y., Kako, Y., Nagai, T., Ohashi, H. GPC3 mutations in seven patients with Simpson-Golabi-Behmel syndrome. Am. J. Med. Genet. 143A: 1703-1707, 2007.
13. Shen, T., Sonoda, G., Hamid, J., Li, M., Filmus, J., Buick, R. N., Testa, J. R. Mapping of the Simpson-Golabi-Behmel overgrowth syndrome gene (GPC3) to chromosome X in human and rat by fluorescence in situ hybridization. Mammalian Genome 8: 72 only, 1997.
14. Shi, W., Filmus, J. A patient with the Simpson-Golabi-Behmel syndrome displays a loss-of-function point mutation in GPC3 that inhibits the attachment of this proteoglycan to the cell surface. (Letter) Am. J. Med. Genet. 149A: 552-554, 2009.
15. Sood, R., Zehnder, J. L., Druzin, M. L., Brown, P. O. Gene expression patterns in human placenta. Proc. Nat. Acad. Sci. 103: 5478-5483, 2006.
16. Veugelers, M., De Cat, B., Muyldermans, S. Y., Reekmans, G., Delande, N., Frints, S., Legius, E., Fryns, J.-P., Schrander-Stumpel, C., Weidle, B., Magdalena, N., David, G. Mutational analysis of the GPC3/GPC4 glypican gene cluster on Xq26 in patients with Simpson-Golabi-Behmel syndrome: identification of loss-of-function mutations in the GPC3 gene. Hum. Molec. Genet. 9: 1321-1328, 2000.
17. White, G. R. M., Kelsey, A. M., Varley, J. M., Birch, J. M. Somatic glypican 3 (GPC3) mutations in Wilms' tumour. Brit. J. Cancer 86: 1920-1922, 2002.
18. Xuan, J. Y., Hughes-Benzie, R. M., MacKenzie, A. E. A small interstitial deletion in the GPC3 gene causes Simpson-Golabi-Behmel syndrome in a Dutch-Canadian family J Med. Genet. 36: 57-58, 1999.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention claimed is:

1. An antibody or antigen-binding fragment thereof comprising a heavy chain variable region (V$_H$) sequence and a light chain variable region (V$_L$) sequence of a clone selected from: 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1 and which specifically binds to glypican-3 (GPC-3).

2. The antibody or antigen-binding fragment according to claim 1, in which the V$_H$ and V$_L$ sequence are selected from: SEQ ID NO: 1 and SEQ ID NO: 2; SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; SEQ ID NO: 11 and SEQ ID NO: 12; SEQ ID NO: 13 and SEQ ID NO: 14; SEQ ID NO: 15 and SEQ ID NO: 16; SEQ ID NO: 17 and SEQ ID NO: 18; SEQ ID NO: 19 and SEQ ID NO: 20; SEQ ID NO: 21 and SEQ ID NO: 22; SEQ ID NO: 23 and SEQ ID NO: 24; SEQ ID NO: 25 and SEQ ID NO: 26; SEQ ID NO: 27 and SEQ ID NO: 28; SEQ ID NO: 29 and SEQ ID NO: 30; SEQ ID NO: 31 and SEQ ID NO: 32; SEQ ID NO: 33 and SEQ ID NO: 34; SEQ ID NO: 35 and SEQ ID NO: 36; SEQ ID NO: 37 and SEQ ID NO: 38; SEQ ID NO: 39 and SEQ ID NO: 40; SEQ ID NO: 41 and SEQ ID NO: 42; SEQ ID NO: 43 and SEQ ID NO: 44; SEQ ID NO: 45 and SEQ ID NO: 46; and SEQ ID NO: 47 and SEQ ID NO: 48.

3. The antibody or antigen-binding fragment according to claim 1, which binds to an epitope of human glypican-3

(GPC-3) with an affinity of 55 nM or less, 50 nM or less, 45 nM or less, 40 nM or less, 35 nM or less, nM or less, 25 nM or less, 20 nM or less, 15 nM or less, 10 nM or less, 5 nM or less, 1 nM or less, 0.9 nM or less, 0.8 nM or less, 0.7 nM or less, 0.6 nM or less, 0.5 nM or less, 0.4 nM or less, 0.3 nM or less, 0.2 nM or less or 0.1 nM or less, measured as a EC50 as determined by ELISA.

4. The antibody or antigen-binding fragment according to claim 1, which binds to a cell line selected from the group consisting of: GPC-3$^{High}$ HepG2 cells; and GPC-3$^{Medium}$ Hep3B cells.

5. The antibody or antigen-binding fragment according to claim 1, which is capable of inducing Antibody-Dependent Cell-mediated Cytotoxicity (ADCC) of a GPC-3 expressing cell in the presence of natural killer (NK) cells, wherein the antibody or antigen-binding fragment comprises a heavy variable chain region ($V_H$) sequence and a light chain variable region ($V_L$) sequence of a clone selected from the group consisting of 1C4 (SEQ ID NOs: 7 and 8, respectively), 1D2 (SEQ ID NOs: 5 and 6, respectively), 1D3 (SEQ ID NOs: 19 and 20, respectively), 1D8 (SEQ ID NOs: 17 and 18, respectively), 1E1 (SEQ ID NOS: 47 and 48, respectively), 1H1 (SEQ ID NOs: 13 and 14, respectively), 1H10 (SEQ ID NOs: 31 and 32, respectively), 2B5 (SEQ ID NOs: 9 and 10, respectively), 2F1 (SEQ ID NOs: 21 and 22, respectively), 3A9 (SEQ ID NOs: 27 and 28, respectively), 3C12 (SEQ ID NOs: 33 and 34, respectively), 3G12 (SEQ ID NOs: 41 and 42, respectively), 4A5 (SEQ ID NOs: 15 and 16, respectively), 4A12 (SEQ ID NOs: 37 and 38, respectively), 4F9 (SEQ ID NOs: 43 and 44, respectively), 4G4 (SEQ ID NOs: 45 and 46, respectively), 4H1 (SEQ ID NOs: 3 and 4, respectively), and 5C4 (SEQ ID Nos: 1 and 2, respectively).

6. The antibody or antigen-binding fragment according claim 1, which is a humanised antibody comprising a human constant region.

7. The antibody or antigen-binding fragment according to claim 1, which comprises a monoclonal antibody, a humanised monoclonal antibody, an Fv, F(ab'), F(ab')$_2$ or single-chain Fv (scFv) fragment.

8. The antibody or antigen-binding fragment according claim 1, which further comprises a heavy chain variable region ($V_H$) sequence and a light chain variable region ($V_L$) that binds to CD3.

9. The antibody or antigen-binding fragment according to claim 8, in which the heavy chain variable region ($V_H$) sequence and a light chain variable region ($V_L$) sequence that bind to CD3 comprise the sequences set out in SEQ ID NO: 97 and SEQ ID NO: 98.

10. The antibody or antigen-binding fragment according to claim 8, which activates T-cells.

11. A chimeric antigen receptor (CAR) comprising: (a) the antigen-binding fragment according to claim 1; (b) a transmembrane domain; and (c) a co-stimulatory intracellular signalling domain; or a chimeric antigen receptor T Cell (CAR T) expressing said chimeric antigen receptor.

12. A nucleic acid that encodes an antibody or antigen-binding fragment according claim 1, comprising sequences selected from the group consisting of: SEQ ID NO: 49 and SEQ ID NO: 50; SEQ ID NO: 51 and SEQ ID NO: 52; SEQ ID NO: 53 and SEQ ID NO: 54; SEQ ID NO: 55 and SEQ ID NO: 56; SEQ ID NO: 57 and SEQ ID NO: 58; SEQ ID NO: 59 and SEQ ID NO: 60; SEQ ID NO: 61 and SEQ ID NO: 62; SEQ ID NO: 63 and SEQ ID NO: 64; SEQ ID NO: 65 and SEQ ID NO: 66; SEQ ID NO: 67 and SEQ ID NO: 68; SEQ ID NO: 69 and SEQ ID NO: 70; SEQ ID NO: 71 and SEQ ID NO: 72; SEQ ID NO: 73 and SEQ ID NO: 74; SEQ ID NO: 75 and SEQ ID NO: 76; SEQ ID NO: 77 and SEQ ID NO: 78; SEQ ID NO: 79 and SEQ ID NO: 80; SEQ ID NO: 81 and SEQ ID NO: 82; SEQ ID NO: 83 and SEQ ID NO: 84; SEQ ID NO: 85 and SEQ ID NO: 86; SEQ ID NO: 87 and SEQ ID NO: 88; SEQ ID NO: 89 and SEQ ID NO: 90; SEQ ID NO: 91 and SEQ ID NO: 92; SEQ ID NO: 93 and SEQ ID NO: 94; and SEQ ID NO: 95 and SEQ ID NO: 96.

13. A host cell comprising the nucleic acid according to claim 12, in which the host cell comprises a Chinese Hamster Ovary (CHO) or a HEK293 cell.

14. A pharmaceutical composition comprising:
(a) an antibody or antigen-binding fragment thereof comprising a heavy chain variable region ($V_H$) sequence and a light chain variable region ($V_L$) sequence of a clone selected from: 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1 and which specifically binds to glypican-3 (GPC-3); or
(b) a CAR comprising: (i) the antigen-binding fragment according to (a); (ii) a transmembrane domain; and (iii) a co-stimulatory intracellular signalling domain; or a CAR T expressing said CAR; or
(c) a nucleic acid that encodes the antibody or antigen-binding fragment of (a), comprising sequences selected from the group consisting of: SEQ ID NO: 49 and SEQ ID NO: 50; SEQ ID NO: 51 and SEQ ID NO: 52; SEQ ID NO: 53 and SEQ ID NO: 54; SEQ ID NO: 55 and SEQ ID NO: 56; SEQ ID NO: 57 and SEQ ID NO: 58; SEQ ID NO: 59 and SEQ ID NO: 60; SEQ ID NO: 61 and SEQ ID NO: 62; SEQ ID NO: 63 and SEQ ID NO: 64; SEQ ID NO: 65 and SEQ ID NO: 66; SEQ ID NO: 67 and SEQ ID NO: 68; SEQ ID NO: 69 and SEQ ID NO: 70; SEQ ID NO: 71 and SEQ ID NO: 72; SEQ ID NO: 73 and SEQ ID NO: 74; SEQ ID NO: 75 and SEQ ID NO: 76; SEQ ID NO: 77 and SEQ ID NO: 78; SEQ ID NO: 79 and SEQ ID NO: 80; SEQ ID NO: 81 and SEQ ID NO: 82; SEQ ID NO: 83 and SEQ ID NO: 84; SEQ ID NO: 85 and SEQ ID NO: 86; SEQ ID NO: 87 and SEQ ID NO: 88; SEQ ID NO: 89 and SEQ ID NO: 90; SEQ ID NO: 91 and SEQ ID NO: 92; SEQ ID NO: 93 and SEQ ID NO: 94; and SEQ ID NO: 95 and SEQ ID NO: 96.

15. A compound comprising the antibody or antigen-binding fragment thereof according to claim 1 linked to a cytotoxic agent.

16. The compound according to claim 15, in which the compound comprises an antibody-drug conjugate.

17. A method of producing an antibody or antigen-binding fragment, the method comprising expressing the nucleic acid according to claim 12 in a host cell.

18. A method of detecting a hepatocellular carcinoma (HCC) cell, the method comprising detecting modulation of expression, amount or activity of glypican-3 (GPC-3) in or of the cell, by means of the antibody or antigen-binding fragment according to claim 1.

19. A method of diagnosing hepatocellular carcinoma (HCC) in an individual, in which the method comprises detecting, in a cell of the individual:
a modulated expression level of glypican-3 (GPC-3) by contacting the cell with the antibody or antigen-binding fragment according to claim 1;
as compared to the expression level of glypican-3 in a cell of an individual known not to be suffering from hepatocellular carcinoma (HCC);

in which an increased expression level of the glypican-3 indicates that the individual is suffering, or is likely to be suffering, from hepatocellular carcinoma (HCC).

20. A diagnostic kit for hepatocellular carcinoma (HCC), the kit comprising the antibody or antigen-binding fragment according to claim 1 or a nucleic acid according to claim 12 together with instructions for use.

21. A method of treating or alleviating a cancer-in a subject, comprising administering to the subject:
- (a) an antibody or antigen-binding fragment thereof comprising a heavy chain variable region ($V_H$) sequence and a light chain variable region ($V_L$) sequence of a clone selected from: 5C4, 4H1, 1D2, 1C4, 2B5, 1F1, 1H1, 4A5, 1D8, 1D3, 2F1, 3C6, 3D12, 3A9, 1F4, 1H10, 3C12, 4G11, 4A12, 1A12, 3G12, 4F9, 4G4 and 1E1 and which specifically binds to glypican-3 (GPC-3);
- (b) a CAR comprising: (i) the antigen-binding fragment according to (a); (ii) a transmembrane domain; and (iii) a co-stimulatory intracellular signalling domain; or a CAR T expressing said CAR;
- (c) a nucleic acid that encodes the antibody or antigen-binding fragment of (a), comprising sequences selected from the group consisting of: SEQ ID NO: 49 and SEQ ID NO: 50; SEQ ID NO: 51 and SEQ ID NO: 52; SEQ ID NO: 53 and SEQ ID NO: 54; SEQ ID NO: 55 and SEQ ID NO: 56; SEQ ID NO: 57 and SEQ ID NO: 58; SEQ ID NO: 59 and SEQ ID NO: 60; SEQ ID NO: 61 and SEQ ID NO: 62; SEQ ID NO: 63 and SEQ ID NO: 64; SEQ ID NO: 65 and SEQ ID NO: 66; SEQ ID NO: 67 and SEQ ID NO: 68; SEQ ID NO: 69 and SEQ ID NO: 70; SEQ ID NO: 71 and SEQ ID NO: 72; SEQ ID NO: 73 and SEQ ID NO: 74; SEQ ID NO: 75 and SEQ ID NO: 76; SEQ ID NO: 77 and SEQ ID NO: 78; SEQ ID NO: 79 and SEQ ID NO: 80; SEQ ID NO: 81 and SEQ ID NO: 82; SEQ ID NO: 83 and SEQ ID NO: 84; SEQ ID NO: 85 and SEQ ID NO: 86; SEQ ID NO: 87 and SEQ ID NO: 88; SEQ ID NO: 89 and SEQ ID NO: 90; SEQ ID NO: 91 and SEQ ID NO: 92; SEQ ID NO: 93 and SEQ ID NO: 94; and SEQ ID NO: 95 and SEQ ID NO: 96;
- (d) a pharmaceutical composition comprising the antibody or antigen-binding fragment of (a), the CAR or CAR T of (b), or the nucleic acid of (c), together with a pharmaceutically acceptable excipient, diluent or carrier; or
- (e) a compound comprising the antibody or antigen-binding fragment thereof (a) linked to a cytotoxic agent.

22. The compound of claim 15, wherein the antibody or antigen-binding fragment is linked to a cytotoxic agent by a cleavable linker.

23. The method of treating or alleviating a cancer of claim 21, wherein the compound comprises an antibody or antigen-binding fragment thereof linked to a cytotoxic agent by a cleavable linker.

24. The method of treating or alleviating a cancer of claim 21, wherein the method of treatment is for hepatocellular carcinoma (HCC).

* * * * *

SEQUENCE LISTING

<160> NUMBER OF SEQ ID NOS: 102

<210> SEQ ID NO 1
<211> LENGTH: 117
<212> TYPE: PRT
<213> ORGANISM: Mus musculus

<400> SEQUENCE: 1

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Ala Gly Pro Phe Thr Gly Phe Asn Trp Phe Asp Pro Trp
            100                 105                 110

Gly Gln Gly Thr Leu
            115

<210> SEQ ID NO 2
<211> LENGTH: 104
<212> TYPE: PRT
<213> ORGANISM: Mus musculus

<400> SEQUENCE: 2

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Asp Ser Tyr
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Ile Pro Ala Arg Phe Ser Gly
    50                  55                  60

Thr Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Lys Arg Trp Pro Thr
                85                  90                  95

Trp Thr Phe Gly Leu Gly Thr Arg
            100

<210> SEQ ID NO 3
<211> LENGTH: 111
<212> TYPE: PRT
<213> ORGANISM: Mus musculus

<400> SEQUENCE: 3

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

```
Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Pro Gly Leu Glu Asp Tyr Trp Gly Gln Gly Thr Leu
            100                 105                 110

<210> SEQ ID NO 4
<211> LENGTH: 104
<212> TYPE: PRT
<213> ORGANISM: Mus musculus

<400> SEQUENCE: 4

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Thr Ala Pro Lys Leu Leu Ile
         35                  40                  45

Tyr Ala Ala Ser Ser Leu Gln Ser Gly Val Pro Ser Arg Phe Ser
     50                  55                  60

Gly Ser Gly Ser Gly Thr Asp Phe Ala Leu Thr Ile Ser Ser Leu Gln
 65                  70                  75                  80

Pro Glu Asp Phe Ala Thr Tyr Tyr Cys Leu Gln Asp Tyr Asn Tyr Pro
                 85                  90                  95

Leu Thr Phe Gly Gly Gly Thr Lys
                 100

<210> SEQ ID NO 5
<211> LENGTH: 118
<212> TYPE: PRT
<213> ORGANISM: Mus musculus

<400> SEQUENCE: 5

Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Trp Gln Gln Gln Leu Val Pro Leu Gly Tyr Met Asp Val
            100                 105                 110

Trp Gly Lys Gly Thr Thr
            115

<210> SEQ ID NO 6
<211> LENGTH: 105
<212> TYPE: PRT
<213> ORGANISM: Mus musculus
```

```
<400> SEQUENCE: 6

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser His Ser Val Ser Ser Asn
            20                  25                  30

Phe Leu Ala Trp Tyr Gln Gln Lys Pro Gly Gln Ala Pro Arg Leu Leu
        35                  40                  45

Ile Tyr Ala Ala Ser Ser Arg Thr Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ser Ala Val Tyr Tyr Cys Gln Gln Tyr Gly Tyr Ser Pro
                85                  90                  95

Leu Tyr Thr Phe Gly Gln Gly Thr Lys
            100                 105

<210> SEQ ID NO 7
<211> LENGTH: 117
<212> TYPE: PRT
<213> ORGANISM: Mus musculus

<400> SEQUENCE: 7

Gln Val Gln Leu Val Gln Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Gly Asp Tyr Tyr Arg Pro Tyr Gly Met Asp Val Trp
            100                 105                 110

Gly Gln Gly Thr Thr
        115

<210> SEQ ID NO 8
<211> LENGTH: 103
<212> TYPE: PRT
<213> ORGANISM: Mus musculus

<400> SEQUENCE: 8

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Lys Trp
            20                  25                  30

Leu Ala Trp Tyr Gln His Lys Pro Gly Lys Ala Pro Lys Val Leu Ile
        35                  40                  45

Tyr Lys Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

```
Glu Asp Phe Ala Thr Tyr Tyr Cys Gln Gln Leu Asn Ser Tyr Pro Leu
                85                  90                  95

Thr Phe Gly Gly Gly Thr Lys
            100
```

<210> SEQ ID NO 9
<211> LENGTH: 124
<212> TYPE: PRT
<213> ORGANISM: Mus musculus

<400> SEQUENCE: 9

```
Gln Val Gln Leu Gln Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
                35                  40                  45

Ala Val Ile Ser Tyr Asp Gly Ser Asn Lys Tyr Tyr Ala Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Thr Tyr Tyr Tyr Asp Ser Ser Gly Tyr Trp Asp Tyr
                100                 105                 110

Tyr Tyr Gly Met Asp Val Trp Gly Gln Gly Thr Thr
                115                 120
```

<210> SEQ ID NO 10
<211> LENGTH: 108
<212> TYPE: PRT
<213> ORGANISM: Mus musculus

<400> SEQUENCE: 10

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asp Ser
                20                  25                  30

Asp Gly Tyr Asn Phe Leu Asp Trp Tyr Val Gln Lys Pro Gly Gln Ser
                35                  40                  45

Pro Gln Arg Leu Ile Tyr Leu Gly Ser Ile Arg Ala Ser Gly Val Pro
                50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Val Tyr Tyr Cys Met Gln Ala
                85                  90                  95

Leu Gln Thr Pro Trp Thr Phe Gly Gln Gly Thr Lys
                100                 105
```

<210> SEQ ID NO 11
<211> LENGTH: 107
<212> TYPE: PRT
<213> ORGANISM: Mus musculus

<400> SEQUENCE: 11

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

```
                    20                  25                  30
Gly Ile Ser Trp Val Arg Gln Ala Pro Gly Gln Arg Leu Glu Trp Met
            35                  40                  45
Gly Trp Ile Asn Ala Gly Asn Gly Asn Thr Lys Tyr Ser Gln Lys Phe
        50                  55                  60
Gln Gly Arg Val Thr Ile Thr Arg Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Thr Val Val Tyr Trp Gly Gln Gly Thr Leu
                100                 105

<210> SEQ ID NO 12
<211> LENGTH: 108
<212> TYPE: PRT
<213> ORGANISM: Mus musculus

<400> SEQUENCE: 12

Glu Ile Val Leu Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
                20                  25                  30
Asn Gly Tyr Asn Tyr Leu Asp Trp Tyr Leu Gln Lys Pro Gly Gln Ser
            35                  40                  45
Pro Gln Ile Leu Ile Tyr Leu Gly Ser His Arg Ala Ser Gly Val Pro
        50                  55                  60
Asp Arg Phe Ser Gly Ser Ala Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Leu Gln Thr Pro Leu Thr Phe Gly Gly Gly Thr Lys
                100                 105

<210> SEQ ID NO 13
<211> LENGTH: 118
<212> TYPE: PRT
<213> ORGANISM: Mus musculus

<400> SEQUENCE: 13

Gln Val Gln Leu Gln Glu Ser Gly Ala Gly Leu Leu Arg Pro Ser Glu
1               5                   10                  15
Thr Leu Ser Leu Thr Cys Ala Val Tyr Gly Gly Ser Phe Ser Gly Tyr
                20                  25                  30
Tyr Trp Ser Trp Ile Arg Gln Pro Pro Gly Lys Gly Leu Glu Trp Leu
            35                  40                  45
Gly Glu Ile Ser His Ser Gly Ser Thr Asn Tyr Asn Pro Ser Leu Lys
        50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Ala Ala Val Tyr Tyr Cys Ala
                85                  90                  95
Arg Trp Val Trp Ser Gly Tyr Tyr Asn Gly Glu Gly Tyr Phe Asp Leu
                100                 105                 110
Trp Gly Arg Gly Thr Leu
            115
```

-continued

```
<210> SEQ ID NO 14
<211> LENGTH: 104
<212> TYPE: PRT
<213> ORGANISM: Mus musculus

<400> SEQUENCE: 14

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Arg Gly Ser Gly Thr Asp Phe Thr Leu Thr Ile Thr Arg Leu Glu
65                  70                  75                  80

Pro Glu Asp Phe Ala Val Tyr Tyr Cys Gln Tyr Tyr Gly Ser Ser Pro
                85                  90                  95

Arg Thr Phe Gly Gln Gly Thr Lys
            100

<210> SEQ ID NO 15
<211> LENGTH: 120
<212> TYPE: PRT
<213> ORGANISM: Mus musculus

<400> SEQUENCE: 15

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Leu Ser Ser Trp Phe Tyr Tyr Tyr Gly Met
            100                 105                 110

Asp Val Trp Gly Gln Gly Thr Thr
            115                 120

<210> SEQ ID NO 16
<211> LENGTH: 105
<212> TYPE: PRT
<213> ORGANISM: Mus musculus

<400> SEQUENCE: 16

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
            85                  90                  95

Leu Gln Thr Phe Gly Gln Gly Thr Lys
            100                 105

<210> SEQ ID NO 17
<211> LENGTH: 122
<212> TYPE: PRT
<213> ORGANISM: Mus musculus

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Asp Gly Gly Leu Ile Ala Ala Ala Phe Gly Tyr Tyr Tyr Tyr
            100                 105                 110

Gly Met Asp Val Trp Gly Gln Gly Thr Thr
        115                 120

<210> SEQ ID NO 18
<211> LENGTH: 102
<212> TYPE: PRT
<213> ORGANISM: Mus musculus

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Glu Arg Pro Pro Thr
            85                  90                  95

Phe Gly Gly Gly Thr Lys
            100

<210> SEQ ID NO 19
<211> LENGTH: 114
<212> TYPE: PRT
<213> ORGANISM: Mus musculus

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Asn Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Ser Trp Gln Thr Gly Ser Phe Asp Ile Trp Gly Gln Gly
            100                 105                 110

Thr Thr

<210> SEQ ID NO 20
<211> LENGTH: 106
<212> TYPE: PRT
<213> ORGANISM: Mus musculus

<400> SEQUENCE: 20

Ser Tyr Glu Leu Thr Gln Pro Pro Ser Val Ser Gly Thr Pro Gly Gln
1               5                   10                  15

Ser Val Thr Ile Ser Cys Ser Gly Ser Asn Ser Asn Leu Gly Ser Asn
            20                  25                  30

Tyr Val Tyr Trp Tyr Gln Val Val Pro Gly Thr Ala Pro Lys Leu Val
        35                  40                  45

Ile Tyr Arg Asn Lys Tyr Arg Pro Pro Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Asp Asp Glu Ala Glu Tyr Tyr Cys Ser Gly Trp Asp Asp Ser Leu
            85                  90                  95

Ser Gly Arg Leu Phe Gly Gly Gly Thr Lys
            100                 105

<210> SEQ ID NO 21
<211> LENGTH: 114
<212> TYPE: PRT
<213> ORGANISM: Mus musculus

<400> SEQUENCE: 21

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asp Ser Pro Tyr Tyr Tyr Tyr Met Asp Val Trp Gly Lys Gly

Thr Thr

<210> SEQ ID NO 22
<211> LENGTH: 108
<212> TYPE: PRT
<213> ORGANISM: Mus musculus

<400> SEQUENCE: 22

Asp Val Val Met Thr Gln Ser Pro Leu Phe Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Ser Trp Phe Gln Gln Arg Pro Gly Gln Ser
        35                  40                  45

Pro Arg Arg Leu Val Tyr Lys Val Ser Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Arg Thr Phe Gly Gln Gly Thr Lys
            100                 105

<210> SEQ ID NO 23
<211> LENGTH: 115
<212> TYPE: PRT
<213> ORGANISM: Mus musculus

<400> SEQUENCE: 23

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Tyr Gly Arg Tyr Asn Trp Asn Leu Tyr Phe Asp Tyr Trp Gly Gln
            100                 105                 110

Gly Thr Leu
        115

<210> SEQ ID NO 24
<211> LENGTH: 107
<212> TYPE: PRT
<213> ORGANISM: Mus musculus

<400> SEQUENCE: 24

Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

```
Tyr Val Gln Trp Tyr Gln Gln Arg Pro Gly Ser Val Pro Thr Thr Val
            35                  40                  45

Ile Tyr Glu Asp Asn Gln Arg Pro Ser Gly Val Pro Asp Arg Phe Ser
 50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Phe Asp Ser
                85                  90                  95

Ser Asn Tyr Trp Val Phe Gly Gly Gly Thr Lys
           100                 105
```

<210> SEQ ID NO 25
<211> LENGTH: 118
<212> TYPE: PRT
<213> ORGANISM: Mus musculus

<400> SEQUENCE: 25

```
Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Ile Ala Ala Arg Pro Ser Tyr Tyr Tyr Met Asp Val
            100                 105                 110

Trp Gly Lys Gly Thr Thr
        115
```

<210> SEQ ID NO 26
<211> LENGTH: 103
<212> TYPE: PRT
<213> ORGANISM: Mus musculus

<400> SEQUENCE: 26

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asn Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Ile Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Arg
            100
```

<210> SEQ ID NO 27
<211> LENGTH: 112

<212> TYPE: PRT
<213> ORGANISM: Mus musculus

<400> SEQUENCE: 27

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Tyr Lys Arg Arg Pro Phe Asp Tyr Trp Gly Gln Gly Thr Leu
            100                 105                 110

<210> SEQ ID NO 28
<211> LENGTH: 104
<212> TYPE: PRT
<213> ORGANISM: Mus musculus

<400> SEQUENCE: 28

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg
            100

<210> SEQ ID NO 29
<211> LENGTH: 112
<212> TYPE: PRT
<213> ORGANISM: Mus musculus

<400> SEQUENCE: 29

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Val Ala Asp Thr Ala Val Tyr Tyr Cys Ala 85                  90                  95

Arg Leu Tyr Lys Arg Arg Pro Phe Asp Tyr Trp Gly Gln Gly Thr Leu
                100                 105                 110

<210> SEQ ID NO 30
<211> LENGTH: 104
<212> TYPE: PRT
<213> ORGANISM: Mus musculus

<400> SEQUENCE: 30

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
                20                  25                  30

Tyr Leu Ala Trp Tyr Gln Gln Lys Pro Gly Gln Ala Pro Arg Leu Leu
            35                  40                  45

Ile Tyr Gly Ala Ser Arg Arg Ala Thr Gly Ser Pro Glu Arg Phe Ser
        50                  55                  60

Gly Gly Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Asn Ser Pro
                85                  90                  95

Gly Thr Phe Gly Gln Gly Thr Lys
                100

<210> SEQ ID NO 31
<211> LENGTH: 110
<212> TYPE: PRT
<213> ORGANISM: Mus musculus

<400> SEQUENCE: 31

Gln Leu Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Val Met Ser Trp Val Arg Gln Ala Pro Gly Lys Gly Leu Glu Trp Val
            35                  40                  45

Ser Thr Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Val Met Gly Trp Tyr Phe Asp Leu Trp Gly Arg Gly Thr Leu
                100                 105                 110

<210> SEQ ID NO 32
<211> LENGTH: 106
<212> TYPE: PRT
<213> ORGANISM: Mus musculus

<400> SEQUENCE: 32

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Asp Ala Ser Asn Arg Ala Thr Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Arg Ser Asn Trp Pro
                85                  90                  95

Pro Arg Ala Thr Phe Gly Gln Gly Thr Arg
            100                 105

<210> SEQ ID NO 33
<211> LENGTH: 116
<212> TYPE: PRT
<213> ORGANISM: Mus musculus

<400> SEQUENCE: 33

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Ser Arg Ile Ala Ala Arg Arg Val Leu Asp Tyr Trp Gly
                100                 105                 110

Gln Gly Thr Leu
        115

<210> SEQ ID NO 34
<211> LENGTH: 102
<212> TYPE: PRT
<213> ORGANISM: Mus musculus

<400> SEQUENCE: 34

Gln Ser Val Leu Thr Gln Pro Pro Ser Ala Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Ala Gln Pro Met
65                  70                  75                  80

Asp Glu Ala Asp Tyr Tyr Cys Gln Ala Trp Tyr Ser Thr Ile Met Val
                85                  90                  95

Phe Gly Gly Gly Thr Lys
            100

<210> SEQ ID NO 35
<211> LENGTH: 113
<212> TYPE: PRT
<213> ORGANISM: Mus musculus -continued

<400> SEQUENCE: 35

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Thr Ser Gly Val Ala Phe Asp Tyr Trp Gly Gln Gly Thr
            100                 105                 110

Leu

<210> SEQ ID NO 36
<211> LENGTH: 103
<212> TYPE: PRT
<213> ORGANISM: Mus musculus

<400> SEQUENCE: 36

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Gly Gly Ser Gly Thr Asp Phe Thr Leu Thr Ile Ser Arg Leu Glu
65                  70                  75                  80

Pro Glu Asp Ser Ala Val Tyr Tyr Cys Gln Gln Tyr Asp His Ser Pro
                85                  90                  95

Thr Phe Gly Gln Gly Thr Lys
            100

<210> SEQ ID NO 37
<211> LENGTH: 111
<212> TYPE: PRT
<213> ORGANISM: Mus musculus

<400> SEQUENCE: 37

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                85                  90                  95
Ala Glu Gly Arg Ile Gln Leu Asp Tyr Trp Gly Gln Gly Thr Leu
            100                 105                 110

<210> SEQ ID NO 38
<211> LENGTH: 103
<212> TYPE: PRT
<213> ORGANISM: Mus musculus

<400> SEQUENCE: 38

Leu Pro Val Leu Thr Gln Pro Pro Ser Val Ser Val Ser Pro Gly Gln
1               5                   10                  15

Thr Ala Arg Ile Thr Cys Ser Gly Tyr Glu Leu Gly Asp Lys Tyr Ala
            20                  25                  30

Phe Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Ser Ser Gly Asp Thr Ala Thr Leu Ile Ile Ser Gly Thr Gln Ile Leu
65                  70                  75                  80

Asp Glu Ala Asp Tyr Tyr Cys Gln Ala Trp Asp Ser Ser Thr His Val
                85                  90                  95

Val Phe Gly Gly Gly Thr Lys
            100

<210> SEQ ID NO 39
<211> LENGTH: 112
<212> TYPE: PRT
<213> ORGANISM: Mus musculus

<400> SEQUENCE: 39

Gln Val Gln Leu Gln Gln Trp Gly Ala Gly Leu Leu Lys Pro Ser Glu
1               5                   10                  15

Thr Leu Ser Leu Thr Cys Ala Ala Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Tyr Lys Arg Arg Pro Phe Asp Tyr Trp Gly Gln Gly Thr Leu
            100                 105                 110

<210> SEQ ID NO 40
<211> LENGTH: 104
<212> TYPE: PRT
<213> ORGANISM: Mus musculus

<400> SEQUENCE: 40

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ile
            20                  25                  30

Tyr Leu Ala Trp Tyr Gln Gln Lys Pro Gly Gln Ala Pro Arg Leu Leu
        35                  40                  45
```

```
Ile Tyr Gly Ala Ser Arg Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Leu
                85                  90                  95

Arg Thr Phe Gly Gln Gly Thr Lys
                100
```

<210> SEQ ID NO 41
<211> LENGTH: 112
<212> TYPE: PRT
<213> ORGANISM: Mus musculus

<400> SEQUENCE: 41

```
Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Leu Tyr Lys Arg Arg Pro Phe Asp Tyr Trp Gly Gln Gly Thr Leu
            100                 105                 110
```

<210> SEQ ID NO 42
<211> LENGTH: 104
<212> TYPE: PRT
<213> ORGANISM: Mus musculus

<400> SEQUENCE: 42

```
Glu Thr Thr Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Arg Gly Gln Ala Pro Arg Leu Leu
            35                  40                  45

Ile Tyr Gly Ala Ser Arg Arg Ala Thr Gly Ile Pro Asp Arg Phe Ser
    50                  55                  60

Gly Ser Gly Ser Gly Ser Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Ser Thr Phe Gly Gln Gly Thr Lys
                100
```

<210> SEQ ID NO 43
<211> LENGTH: 123
<212> TYPE: PRT
<213> ORGANISM: Mus musculus

<400> SEQUENCE: 43

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Asn Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Asp Ser Ser Ser Trp Tyr Val Gly Thr Tyr Tyr Tyr Tyr
            100                 105                 110

Tyr Gly Met Asp Val Trp Gly Gln Gly Thr Thr
            115                 120
```

<210> SEQ ID NO 44
<211> LENGTH: 108
<212> TYPE: PRT
<213> ORGANISM: Mus musculus

<400> SEQUENCE: 44

```
Asp Val Val Met Thr Gln Ser Pro Leu Ser Leu Pro Val Thr Pro Gly
1               5                   10                  15

Glu Ser Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Gly Ala Glu Asp Val Gly Val Tyr Tyr Cys Met Gln Val
                85                  90                  95

Leu Gln Thr Pro Trp Thr Phe Gly Gln Gly Thr Lys
            100                 105
```

<210> SEQ ID NO 45
<211> LENGTH: 112
<212> TYPE: PRT
<213> ORGANISM: Mus musculus

<400> SEQUENCE: 45

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

```
Arg Leu Tyr Lys Arg Arg Pro Phe Asp Tyr Trp Gly Gln Gly Thr Leu
            100                 105                 110
```

<210> SEQ ID NO 46
<211> LENGTH: 104
<212> TYPE: PRT
<213> ORGANISM: Mus musculus

<400> SEQUENCE: 46

```
Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asn Ala Ser Arg Arg Ala Thr Gly Ile Pro Asp Arg Phe Ser
    50                  55                  60

Gly Ser Gly Ser Gly Ala Asp Phe Thr Leu Thr Ile Ser Arg Leu Asp
65                  70                  75                  80

Pro Glu Asp Phe Ala Val Tyr Phe Cys Gln Gln Tyr Gly Ser Ser Pro
                85                  90                  95

Gln Thr Phe Gly Gln Gly Thr Lys
            100
```

<210> SEQ ID NO 47
<211> LENGTH: 112
<212> TYPE: PRT
<213> ORGANISM: Mus musculus

<400> SEQUENCE: 47

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Tyr Lys Arg Arg Pro Phe Asp Tyr Trp Gly Gln Gly Thr Leu
            100                 105                 110
```

<210> SEQ ID NO 48
<211> LENGTH: 104
<212> TYPE: PRT
<213> ORGANISM: Mus musculus

<400> SEQUENCE: 48

```
Val Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Arg
            20                  25                  30

Tyr Leu Ala Trp Tyr Gln Gln Arg Pro Gly Gln Ala Pro Arg Leu Leu
        35                  40                  45

Ile Tyr Gly Ala Ser Arg Arg Ala Thr Gly Ser Pro Glu Arg Phe Ser
```

```
                    50                  55                  60
Gly Gly Gly Ser Gly Thr Asp Phe Thr Leu Thr Ile Ser Arg Leu Glu
 65                  70                  75                  80

Pro Glu Asp Phe Ala Val Tyr Tyr Cys Gln His Tyr Gly Asn Ser Pro
                 85                  90                  95

Gly Thr Phe Gly Gln Gly Thr Lys
            100

<210> SEQ ID NO 49
<211> LENGTH: 351
<212> TYPE: DNA
<213> ORGANISM: Mus musculus

<400> SEQUENCE: 49
caggtgcagc tgcaggagtc ggggggaggc ttggtcaagc ctgggggtc cctgagactc     60 tcctgtgcag cctctggatt caccttcagt agctatagca tgaactgggt ccgccaggct    120
ccagggaagg gctggagtg gtggcagtt atatcatatg atggaagtaa taaatactat    180
gcagactccg tgaagggccg attcaccatc tccagagaca attccaagaa cacgctgtat   240
ctgcaaatga acagcctgag aactgaggac acggctgtgt attactgtgc gaggggcgcg    300 gggccttta cgggattcaa ctggttcgac ccctggggcc agggaaccct g              351

<210> SEQ ID NO 50
<211> LENGTH: 312
<212> TYPE: DNA
<213> ORGANISM: Mus musculus

<400> SEQUENCE: 50
gaaattgtgt tgacacagtc tccagccacc ctgtctgtgt ctccagggga gagagccacc     60
ctctcctgca gggccagtca gagtgttgac agctacttag cctggtacca gcagaaacct    120
ggccaggctc cccggctcct catctatagt gcgtccacga gggccactgg tatcccagcc    180
aggttcagtg gcactgggtc tgggacagag ttcactctca ccatcagcag cctgcagtct   240
gaagattttg cagtttacta ctgtcagcag tataagaggt ggcccacgtg gacgttcggt    300
ctagggacca gg                                                         312

<210> SEQ ID NO 51
<211> LENGTH: 333
<212> TYPE: DNA
<213> ORGANISM: Mus musculus

<400> SEQUENCE: 51
gaggtccagc tggtacagtc tggggaggc gtggtccagc ctgggaggtc cctgagactc     60
tcctgtgcag cctctggatt caccttcagt agctatgcta tgcactgggt ccgccaggct    120
ccaggcaagg gctggagtg gtggcagtt atatcatatg atggaagcaa taaatactac    180
gcagactccg tgaagggccg attcaccatc tccagagaca attccaagaa cacgctgtat   240
ctgcaaatga acagcctgag agctgaggac acggctgtgt attactgtgc gagagcccct    300
gggttggagg actactgggg ccagggaacc ctg                                 333

<210> SEQ ID NO 52
<211> LENGTH: 312
<212> TYPE: DNA
<213> ORGANISM: Mus musculus

<400> SEQUENCE: 52
```

```
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggacagccc ctaagctcct gatctatgct gcatcatcca gtttacaaag tggggtccca     180
tcaaggttca gcggcagtgg atctggcaca gatttcgctc tcaccatcag cagcctgcag     240
cctgaagatt ttgcaactta ttactgtcta caagattaca attaccctct cactttcggc     300
ggagggacca ag                                                         312

<210> SEQ ID NO 53
<211> LENGTH: 354
<212> TYPE: DNA
<213> ORGANISM: Mus musculus

<400> SEQUENCE: 53
gaggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatcccta tctttggtac agcaaactac     180
gcacagaagt tccagggcag agtcacgatt accgcggaca atccacgag cacagcctac     240 atggagctga gcagcctgag atctgaggac acggccgtgt attactgtgc gagagagtgg     300
cagcagcagc tggtaccccct cggctacatg gacgtctggg gcaaagggac cacg          354

<210> SEQ ID NO 54
<211> LENGTH: 315
<212> TYPE: DNA
<213> ORGANISM: Mus musculus

<400> SEQUENCE: 54
gaaacgacac tcacgcagtc tccaggcacc ctgtctttgt ctccagggga aagagccacc      60
ctctcctgta gggccagtca cagtgttagc agcaacttct agcctggta ccagcagaaa     120 cctggccagg ctcccaggct cctcatctat gctgcatcca gcaggaccac tggcgtccca     180
gacaggttca gtggcagtgg gtctgggaca gacttcactc tcaccatcag cagactggag     240
cctgaagatt ctgcagtgta ttactgtcag caatatggtt actcacccct gtacactttt     300
ggccagggga ccaag                                                      315

<210> SEQ ID NO 55
<211> LENGTH: 351
<212> TYPE: DNA
<213> ORGANISM: Mus musculus

<400> SEQUENCE: 55
caggtccagc tggtgcagtc tggggaggc ttggtaaagc cagggcggtc cctgagactc       60
tcctgtacag cttctggatt cacctttggt gattatgcta tgcactgggt ccgccaggct     120
ccaggcaagg gctggagtg gtggcagtt atatcatatg atggaagcaa taaatactat     180
gcagactccg tgaagggccg attcaccatc tccagagaca attccaagaa cacgctgtat     240
ctgcaaatga acagcctgag agctgaggac acggctgtgt attactgtgc gagagattac     300
ggtgattact atcggcccta cggtatggac gtctggggcc aagggaccac g              351

<210> SEQ ID NO 56
<211> LENGTH: 309
<212> TYPE: DNA
<213> ORGANISM: Mus musculus

<400> SEQUENCE: 56
```

-continued

```
gacatccaga tgacccagtc tccttccacc ctgtctgcct ctgtaggaga cagagtcacc    60
atcacttgtc gggccagtca gagtattagt aagtggttgg cctggtatca gcataaacca   120
gggaaagccc ctaaagtcct gatctataag gcgtctactt tacaaagtgg ggtcccgtcg   180
aggttcagcg gcagtggatc tgggacagaa ttcactctca caatcagcag cctgcagcct   240
gaagattttg caacttatta ctgtcaacag cttaatagtt acccgctcac tttcggcgga   300
gggaccaag                                                            309

<210> SEQ ID NO 57
<211> LENGTH: 372
<212> TYPE: DNA
<213> ORGANISM: Mus musculus

<400> SEQUENCE: 57
caggtgcagc tgcaggagtc cggggaggc gtggtccagc ctggaggtc cctgagactc     60 tcctgtgcag cctctggatt caccttcagt agctatgcta tgcactgggt ccgccaggct   120
ccaggcaagg ggctggagtg ggtggcagtt atatcatatg atggaagcaa taaatactac   180
gcagactccg tgaagggccg attcaccatc tccagagaca attccaagaa cacgctgtat   240
ctgcaaatga acagcctgag agctgaggac acggctgtgt attactgtgc gaaagaggga   300
acgtattact atgatagtag tggttattgg gactactact acggtatgga cgtctggggc   360
caagggacca cg                                                        372

<210> SEQ ID NO 58
<211> LENGTH: 324
<212> TYPE: DNA
<213> ORGANISM: Mus musculus

<400> SEQUENCE: 58
gatgttgtga tgactcagtc tccactctcc ctgcccgtca cccctggaga gccggcctcc    60
atctcctgca ggtctagcca gagcctcctg atagtgacg datacaactt tttggattgg   120
tatgtgcaga agccagggca gtctccacag cgcctgatct atttgggctc tattcgggcc   180
tccggggtcc ctgacaggtt cagtggcagt ggatcaggca cagattttac actgaaaatc   240
agcagagtgg aggctgacga tgttggggtt tattattgca tgcaagctct acaaactcct   300
tggacgttcg gccaagggac caag                                           324

<210> SEQ ID NO 59
<211> LENGTH: 321
<212> TYPE: DNA
<213> ORGANISM: Mus musculus

<400> SEQUENCE: 59
caggtccagc tggtgcagtc tggagctgag gtgaagaagc ctggggcctc agtgaaggtc    60
tcctgcaagg cttctggtta cacctttacc agctatggta tcagctgggt gcgacaggcc   120
cccggacaaa ggcttgagtg gatgggatgg atcaacgctg gcaatggtaa cacaaaatat   180
tcacagaagt tccagggcag agtcaccatt accagggaca catccgcgag cacagcctac   240
atggagctga gcagcctgag atctgaagac acggctgtgt attactgtgc gaccgttgtc   300
tactggggcc agggcaccct g                                              321

<210> SEQ ID NO 60
<211> LENGTH: 324
<212> TYPE: DNA
```

<213> ORGANISM: Mus musculus

<400> SEQUENCE: 60

```
gaaattgtgc tgactcagtc tccactctcc ctgcccgtca ccctggaga gccggcctcc      60
atctcctgca ggtctagtca gagcctcctg catagtaatg gatacaacta tttggattgg    120
tacctgcaga agccagggca gtctccacag atcctgatct acttgggttc tcatcgggcc   180
tccggggtcc ctgacaggtt cagtggcagt gcatcaggca cagattttac actgaaaatc   240
agcagagtgg aggctgagga tgttggggtt tattactgca tgcaagctct acaaactccc   300
ctcactttcg gcggagggac caag                                           324
```

<210> SEQ ID NO 61
<211> LENGTH: 354
<212> TYPE: DNA
<213> ORGANISM: Mus musculus

<400> SEQUENCE: 61

```
caggtgcagc tgcaggagtc cggcgcagga ctgttgaggc cttcggagac cctgtccctc     60
acttgcgctg tctatggtgg gtccttcagt ggttactact ggagctggat ccgccagccc   120
ccagggaagg gctggagtg gcttgggaa atcagtcata gtggaagcac caactacaac    180
ccgtccctca agagtcgagt caccatatca gttgacacgt ccaagaacca gttctccctg   240
aagctgagct ctgtgaccgc cgcggacgcg gctgtatatt actgtgcgag atgggtttgg   300
agtggttatt ataacggtga ggggtacttc gatctctggg gccgtggcac cctg          354
```

<210> SEQ ID NO 62
<211> LENGTH: 312
<212> TYPE: DNA
<213> ORGANISM: Mus musculus

<400> SEQUENCE: 62

```
gaaacgacac tcacgcagtc tcctggcacc ctgtctttgt ctccaggtga aagagccacc     60
ctctcctgta gggccagtca gagtgttagc agcagctact tagcctggta ccagcagaag   120
cctggccagg ctcccaggct cctcatctat ggtgcatcca gcagggccac tggcatccca   180
gacaggttca gtggccgtgg gtctgggaca gacttcactc tcactatcac cagactggag   240
cctgaagatt ttgcagtgta ttactgtcag tactatggta gctcacctcg gacttttggc   300
caggggacca ag                                                        312
```

<210> SEQ ID NO 63
<211> LENGTH: 360
<212> TYPE: DNA
<213> ORGANISM: Mus musculus

<400> SEQUENCE: 63

```
gaggtccagc tggtgcagtc tggagctgag gtgaagaagc ctggggcctc agtgaaggtc     60
tcctgcaagg cttctggtta cacctttacc agctacggta tcagctgggt gcgacaggcc   120
cctggacaag gcttgagtg gatgggatgg atcagcgctt acaatggtaa cacaaactat    180
gcacagaagc tccagggcag agtcaccatg accacagaca catccacgag cacagcctac   240
atggagctga ggagcctgag atctgacgac acggccgtgt attactgtgc gagagacgga   300
ttaagcagca gctggttcta ctactactac ggtatggacg tctggggcca agggaccacg   360
```

<210> SEQ ID NO 64
<211> LENGTH: 315

```
<212> TYPE: DNA
<213> ORGANISM: Mus musculus

<400> SEQUENCE: 64
gatgttgtga tgactcagtc tccactatcc ctgcccgtca cccctggaga gccggcctcc      60
atctcctgca ggtctagtca gagcctcctg catagtaatg gatacaacta tttggattgg     120
tacctgcaga agccagggca gtctccacag ctcctgatct atttgggttc taatcgggcc     180
tccggggtcc ctgacaggtt cagtggcagt ggatcaggca cagattttac actgaaaatc     240
agcagagtgg aggctgagga tgttggggtt tattactgca tgcaagctct acaaactttt     300
ggccagggga ccaag                                                      315

<210> SEQ ID NO 65
<211> LENGTH: 366
<212> TYPE: DNA
<213> ORGANISM: Mus musculus

<400> SEQUENCE: 65
caggtccagc tggtacagtc tggagctgag gtgaagaagc ctggggcctc agtgaaggtc      60
tcctgcaagg cttctggtta cacctttacc agctacggta tcagctgggt gcgacaggcc     120
cctggacaag gcttgagtg gatgggatgg atcagcgctt acaatggtaa cacaaactat     180
gcacagaagc tccagggcag agtcaccatg accacagaca catccacgag cacagcctac     240
atggagctga ggagcctgag atctgacgac acggccgtgt attactgtgc gagagatggg     300
ggacttatag cagcagcttt cggttactac tactacggta tggacgtctg ggggccaaggg     360 accacg                                                                366

<210> SEQ ID NO 66
<211> LENGTH: 306
<212> TYPE: DNA
<213> ORGANISM: Mus musculus

<400> SEQUENCE: 66
gaaattgtgt tgacgcagtc tccaggcacc ctgtctttgt ctccagggga aagagccacc      60
ctctcctgca gggccagtca gagtgttagc agctacttag cctggtacca gcagaaacct     120
ggccaggctc ccaggctcct catctatggt gcatccagca gggccactgg catcccagac     180
aggttcagtg gcagtgggtc tgggacagac ttcactctca ccatcagcag actggagcct     240
gaagattttg cagtgtacta ctgtcaacag tatgagaggc cccccacttt cggcgggggg     300
accaag                                                                306

<210> SEQ ID NO 67
<211> LENGTH: 342
<212> TYPE: DNA
<213> ORGANISM: Mus musculus

<400> SEQUENCE: 67
caggtgcagc tggtgcagtc tggggctgag gtgaagaagc ctggggcctc agtgaaggtc      60
tcctgcaagg cttctggata cacccttcacc ggctactata tgcactgggt gcgacaggcc    120
cctggacaag gcttgagtg gatgggatgg atcaaccctA acagtggtgg cacaaactat      180
gcacagaact tccagggcag agtcaccatt accagggaca tccgcgagac agcctac         240 atggagctga gcagcctgag atctgaggac acggccgtgt attactgtgc gaggggatcg     300
tggcaaacgg gttctttga tatctggggc caaggaacca cg                         342
```

<210> SEQ ID NO 68
<211> LENGTH: 318
<212> TYPE: DNA
<213> ORGANISM: Mus musculus

<400> SEQUENCE: 68

| tcctatgagc tgactcagcc accctcagtg tctgggaccc ccgggcagag tgtcaccatc | 60 |
| tcttgttctg ggagcaactc caacctcgga tctaattatg tgtactggta ccaggtggtc | 120 |
| ccaggcacgg cccccaaact cgtcatctat agaaataaat atcggccccc agggggtccct | 180 |
| gaccgattct ctggctccaa gtctggcacc tcagcctccc tggccatcag tgggctccgg | 240 |
| tccgacgatg aggctgaata ttattgttcc ggatgggatg acagcctgag tggtcgacta | 300 |
| ttcggcggag ggaccaag | 318 |

<210> SEQ ID NO 69
<211> LENGTH: 342
<212> TYPE: DNA
<213> ORGANISM: Mus musculus

<400> SEQUENCE: 69

| gaggtccagc tggtgcagtc tggggctgag gtgaagaagc ctgggtcctc ggtgaaggtc | 60 |
| tcctgcaagg cttctggagg caccttcagc agctatgcta tcagctgggt gcgacaggcc | 120 |
| cctggacaag ggcttgagtg gatgggaggg atcatcccta tctttggtac agcaaactac | 180 |
| gcacagaagt tccagggcag agtcacgatt accgcggacg aatccacgag cacagcctac | 240 |
| atggagctga gcagcctgag atctgaggac acggccgtgt attactgtgc gagagacagc | 300 |
| ccctactact actacatgga cgtctggggc aaagggacca cg | 342 |

<210> SEQ ID NO 70
<211> LENGTH: 324
<212> TYPE: DNA
<213> ORGANISM: Mus musculus

<400> SEQUENCE: 70

| gatgttgtga tgactcagtc tccgctcttc ctgcccgtca cccttggaca gccggcctcc | 60 |
| atctcctgca ggtctagtca aagcctcgta tacagtgatg gaaacaccta cttgagttgg | 120 |
| tttcagcaga ggccaggcca atctccaagg cgcctagttt ataaggtttc tagccgggac | 180 |
| tctggggtcc cagacagatt cagcggcagt gggtcaggca ctgatttcac actgaaaatc | 240 |
| agcagggtgg aggctgagga tgttggggtt tattactgca tgcaaggtac acactggcct | 300 |
| cggacgttcg gccaagggac caag | 324 |

<210> SEQ ID NO 71
<211> LENGTH: 345
<212> TYPE: DNA
<213> ORGANISM: Mus musculus

<400> SEQUENCE: 71

| caggtgcagc tgcaggagtc ggggggaggc gtggtccagc ctgggaggtc cctgagactc | 60 |
| tcctgtgcag cctctggatt cacccttcagt agctatgcta tgcactgggt ccgccaggct | 120 |
| ccaggcaagg ggctggagtg ggtggcagtt atatcatatg atggaagtaa taaatactac | 180 |
| gcagactccg tgaagggccg attcaccatc tccagagaca attccaagaa cacgctgtat | 240 |
| ctgcaaatga acagcctgag agctgaggac acggctgtgt attactgtgc gtacggtaga | 300 |
| tacaactgga atctttactt tgactactgg ggccagggaa ccctg | 345 |

<210> SEQ ID NO 72
<211> LENGTH: 321
<212> TYPE: DNA
<213> ORGANISM: Mus musculus

<400> SEQUENCE: 72

| | | | | | |
|---|---|---|---|---|---|
| aattttatgc | tgactcagcc | ccactctgtg | tcggagtctc | cggggaagac | ggttaccatc | 60 |
| tcctgcaccg | gcagcagtgg | cagcattgcc | agcaactatg | tgcagtggta | ccagcagcgc | 120 |
| ccgggcagtg | tccccaccac | tgtgatctat | gaggataacc | aaagaccctc | tggggtccct | 180 |
| gatcggttct | ctggctccat | cgacagctcc | tccaactctg | cctccctcac | catctctgga | 240 |
| ctgaagactg | aggacgaggc | tgactactac | tgtcagtctt | ttgatagcag | caattattgg | 300 |
| gtgttcggcg | agggaccaa | g | | | | 321 |

<210> SEQ ID NO 73
<211> LENGTH: 354
<212> TYPE: DNA
<213> ORGANISM: Mus musculus

<400> SEQUENCE: 73

| | | | | | |
|---|---|---|---|---|---|
| gaagtgcagc | tggtgcagtc | tggggctgag | gtgaagaagc | ctgggtcctc | ggtgaaggtc | 60 |
| tcctgcaagg | cttctggagg | caccttcagc | agctatgcta | tcagctgggt | gcgacaggcc | 120 |
| cctggacaag | ggcttgagtg | gatgggaggg | atcatcccta | tctttggtac | agcaaactac | 180 |
| gcacagaagt | tccagggcag | agtcacgatt | accgcggaca | aatccacgag | cacagcctac | 240 |
| atggagctga | gcagcctgag | atctgaggac | acggccgtgt | attactgtgc | gagaggcata | 300 |
| gcagctcgtc | cgagctacta | ctactacatg | gacgtctggg | gcaaagggac | cacg | 354 |

<210> SEQ ID NO 74
<211> LENGTH: 309
<212> TYPE: DNA
<213> ORGANISM: Mus musculus

<400> SEQUENCE: 74

| | | | | | |
|---|---|---|---|---|---|
| gacatccaga | tgacccagtc | tccatcctcc | ctgtctgcat | ctgtaggaga | cagagtcacc | 60 |
| atcacttgcc | gggcaagtca | gaacattagc | agctatttaa | attggtatca | gcagaaacca | 120 |
| gggaaagccc | ctaagctcct | gatctatgct | gcatccagtt | tgcaaagtgg | agtcccatca | 180 |
| aggttcagtg | gcagtggatc | tgggacagat | ttcattctca | ccatcagcag | tctgcaacct | 240 |
| gaagattttg | caacttacta | ctgtcaacag | agttacagta | ccccccccac | cttcggccaa | 300 |
| gggacacga | | | | | | 309 |

<210> SEQ ID NO 75
<211> LENGTH: 336
<212> TYPE: DNA
<213> ORGANISM: Mus musculus

<400> SEQUENCE: 75

| | | | | | |
|---|---|---|---|---|---|
| caggtgcagc | tacagcagtg | gggcgcagga | ctgttgaagc | cttcggagac | cctgtccctc | 60 |
| acctgcgctg | tctatggtgg | gtccttcagt | ggttactact | ggagctggat | ccgccagccc | 120 |
| ccagggaagg | ggctggagtg | gattggggaa | atcaatcata | gtggaagcac | caactacaac | 180 |
| ccgtccctca | agagtcgagt | caccatatca | gtagacacgt | ccaagaacca | gttctccctg | 240 |
| aagctgagct | ctgtgaccgc | cgcggacacg | gctgtgtatt | actgtgcgag | actttataaa | 300 |

```
aggaggccct tgactactg gggccagggc accctg                    336
```

<210> SEQ ID NO 76
<211> LENGTH: 312
<212> TYPE: DNA
<213> ORGANISM: Mus musculus

<400> SEQUENCE: 76

```
gaaacgacac tcacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca aagggccac tggcatccca   180
gacaggttca gcggcagtgg gtctgggaca gacttcactc tcaccatcag cagactggag   240
cctgaagatt ttgcagtgta ttactgtcag cagtatggta gctcaccgat caccttcggc   300
caagggacac ga                                                       312
```

<210> SEQ ID NO 77
<211> LENGTH: 336
<212> TYPE: DNA
<213> ORGANISM: Mus musculus

<400> SEQUENCE: 77

```
caggtgcagc tacagcagtg gggcgcagga ctgttgaagc cttcggagac cctgtccctc    60
acctgcgctg tctatggtgg gtccttcagt ggttactact ggagctggat ccgccagccc   120
ccagggaagg ggctggagtg gattgggga atcaatcata gtggaagcac caactacaac   180
ccgtccctca gagtcgagt caccatatca gtagacacg ccaagaacca gttctccctg   240
aagctgagct ctgtgaccgt cgcggacacg gctgtgtatt actgtgcgag actttataaa   300
aggaggccct tgactactg gggccaggga accctg                              336
```

<210> SEQ ID NO 78
<211> LENGTH: 312
<212> TYPE: DNA
<213> ORGANISM: Mus musculus

<400> SEQUENCE: 78

```
gaaacgacac tcacgcagtc tccaggcacc ctgtctttgt ctccagggga aagagccacc    60
ctctcctgca gggccagtca gagtgttagc agcacctact tagcctggta ccagcagaaa   120
cctggccagg ctcccaggct cctcatttac ggtgcatcca ggcgggccac tggctcccca   180
gagaggttca gtggcggtgg gtctgggaca gacttcactc tcaccatcag tagactggag   240
cccgaagatt tcgcagtcta ttactgtcaa cattatggta actcaccggg gacgttcggc   300
caagggacca ag                                                       312
```

<210> SEQ ID NO 79
<211> LENGTH: 330
<212> TYPE: DNA
<213> ORGANISM: Mus musculus

<400> SEQUENCE: 79

```
cagctgcagc tgcaggagtc cggggaggc ttggtacagc ctggggggtc cctgagactc    60
tcctgtgcag cctctggatt cacctttagc agctatgtca tgagctgggt ccgccaggct   120
ccagggaagg ggctggagtg ggtctcaact atcagtggta gtggtgggag cacatactac   180
gcagactccg tgaagggcag attcaccatc tccagagaca attccaagaa cacgctgtat   240
cttcaaatga gcagtctgag agctgaggac acggctgtgt attattgtgt gatgggctgg   300
```

```
tacttcgatc tctggggccg tggaaccctg                              330
```

```
<210> SEQ ID NO 80
<211> LENGTH: 318
<212> TYPE: DNA
<213> ORGANISM: Mus musculus

<400> SEQUENCE: 80
gaaattgtgc tgactcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat gatgcatcca acagggccac tggcatccca   180
gccaggttca gtggcagtgg gtctgggaca gacttcactc tcaccatcag cagcctagag   240
cctgaagatt ttgcagttta ttactgtcag cagcgtagca ctggcccccc gagggccacc   300
ttcggccaag ggacacga                                                 318
```

```
<210> SEQ ID NO 81
<211> LENGTH: 348
<212> TYPE: DNA
<213> ORGANISM: Mus musculus

<400> SEQUENCE: 81
caggtcacct tgaaggagtc tggtcctacg ctggtgaaaac ccacacagac cctcacgctg    60
acctgcacct tctctgggtt ctcactcagc actagtggag tgggtgtggg ctggatccgt   120
cagcccccag gaaaggccct ggagtggctt gcactcattt attggaatga tgataagcgc   180
tacagcccat ctctgaagag caggctcacc atcaccaagg acacctccaa aaaccaggtg   240
gtccttacaa tgaccaacat ggaccctgtg gacacagcca catattactg tgcacacagc   300
cgtatagcag ctcgtcgggt gcttgactac tggggccagg gaaccctg              348
```

```
<210> SEQ ID NO 82
<211> LENGTH: 306
<212> TYPE: DNA
<213> ORGANISM: Mus musculus

<400> SEQUENCE: 82
cagtctgtgc tgactcagcc accctcggcg tcagtggccc caggaaagac ggccaggatt    60
acctgtgggg gaaacaacat tggaagtaaa agtgtgcact ggtaccagca gaagccaggc   120
cagtcccctg tgctggtcat ctatcaagat accagcggc cctcagggat ccctgagcga   180
ttctctggct ccaactctgg gaacacagcc actctgacca tcagcggagc ccagcctatg   240
gatgaggctg actattactg tcaggcgtgg tacagcacca ttatggtatt tggcggaggg   300
accaag                                                              306
```

```
<210> SEQ ID NO 83
<211> LENGTH: 339
<212> TYPE: DNA
<213> ORGANISM: Mus musculus

<400> SEQUENCE: 83
caggtgcagc tgcaggagtc gggcccagga ctggtgaagc cttcgggac cctgtccctc    60 acctgcgctg tctctggtgg ctccatcagc agtagtaact ggtggagttg gtccgccag   120 cccccaggga aggggctgga gtggattggg gaaatctatc atagtgggag caccaactac   180
aacccgtccc tcaagagtcg agtcaccata tcagtagaca agtccaagaa ccagttctcc   240
```
ctgaagctga gctctgtgac cgccgcggac acggccgtgt attactgtgc gagagatact    300
tctggggttg cttttgacta ctggggccag ggcaccctg                           339

<210> SEQ ID NO 84
<211> LENGTH: 309
<212> TYPE: DNA
<213> ORGANISM: Mus musculus

<400> SEQUENCE: 84
gaaattgtgc tgactcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcggtgg gtctgggaca gacttcactc tcaccatcag cagactggag   240
cctgaagatt ctgcagtgta ttactgtcag caatatgatc attcacccac ttttggccag   300
gggaccaag                                                           309

<210> SEQ ID NO 85
<211> LENGTH: 333
<212> TYPE: DNA
<213> ORGANISM: Mus musculus

<400> SEQUENCE: 85
gacgtgcagc tcgtggagtc tggaggaggc ttggtacagc ctgggggtc cctgagactc      60 tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtat attactgtgc ggaggggagg   300
atacagcttg actactgggg ccagggaacc ctg                                333

<210> SEQ ID NO 86
<211> LENGTH: 309
<212> TYPE: DNA
<213> ORGANISM: Mus musculus

<400> SEQUENCE: 86
ctgcctgtgc tgactcagcc cccctcagtg tccgtgtccc caggacagac agccaggatc     60
acctgctctg gatatgaatt gggggataaa tatgcttttct ggtatcagca gaagccaggc  120
cagtcccctg ttctggtcat ttatcaagat accaagcggc cctcagggat ccctgagcga   180
ttctctggct ccagctctgg gacacagcc actctgatca tcagcgggac ccaaattttg    240
gatgaggctg actattactg tcaggcgtgg gacagcagca cccatgtggt attcggcgga   300
gggaccaag                                                           309

<210> SEQ ID NO 87
<211> LENGTH: 336
<212> TYPE: DNA
<213> ORGANISM: Mus musculus

<400> SEQUENCE: 87
caggtgcagc tacagcagtg gggcgcagga ctgttgaagc cttcggagac cctgtccctc      60
acctgcgctg cctatggtgg gtccttcagt ggttactact ggagctggat ccgccagccc   120
ccagggaagg ggctggagtg gattgggaa atcaatcata gtggaagcac caactacaac    180
ccgtccctca agagtcgagt caccatatca gtagacacgt ccaagaacca gttctccctg   240

```
aagctgagct ctgtgaccgc cgcggacacg gctgtgtatt actgtgcgag actttataaa    300
aggaggccct tgactactg gggccaggga accctg                                336

<210> SEQ ID NO 88
<211> LENGTH: 312
<212> TYPE: DNA
<213> ORGANISM: Mus musculus

<400> SEQUENCE: 88
gaaacgacac tcacgcagtc tccaggcacc ctgtctttgt ctccagggga aagagccacc     60
ctctcctgca gggccagtca gagtattagc agcatctact tagcctggta ccagcagaaa   120
cctggccagg ctcccaggct cctcatttat ggtgcatcca ggagggccac tggcatccca   180
gacaggttca gtggcagtgg gtctgggaca gacttcactc tcaccatcag cagactggag   240
cctgaagatt ttgcagtgta ttactgtcag cagtatggta gctcacttcg gacgttcggc   300
caagggacca ag                                                        312

<210> SEQ ID NO 89
<211> LENGTH: 336
<212> TYPE: DNA
<213> ORGANISM: Mus musculus

<400> SEQUENCE: 89
caggtgcagc tacagcagtg gggcgcagga ctgttgaagc cttcggagac cctgtccctc     60
acctgcgctg tctatggtgg gtccttcagt ggttactact ggagctggat ccgccagccc   120
ccagggaagg ggctggagtg gattggggaa atcaatcata gtggaagcac caactacaac   180
ccgtccctca gagtcgagt caccatatca gtagacacgt ccaagaacca gttctccctg    240
aagctgagct ctgtgaccgc cgcggacacg gctgtgtatt actgtgcgag actttataaa   300
aggaggccct tgactactg gggccagggc accctg                               336

<210> SEQ ID NO 90
<211> LENGTH: 312
<212> TYPE: DNA
<213> ORGANISM: Mus musculus

<400> SEQUENCE: 90
gaaacgacac tcacgcagtc tccaggcacc ctgtctttgt ctccagggga aagagccacc     60
ctctcctgca gggccagtca gagtgttagc agcagctact tagcctggta ccagcagaaa   120
cgtggccagg ctcccaggct cctcatctat ggtgcatccc gcagggccac tggcatccca   180
gacaggttca gtggcagtgg gtctgggtca gacttcactc tcaccatcag cagactggag   240
cctgaagatt ttgcagtgta ttactgtcag cagtatggta gctcaccctc gacgttcggc   300
caagggacca ag                                                        312

<210> SEQ ID NO 91
<211> LENGTH: 369
<212> TYPE: DNA
<213> ORGANISM: Mus musculus

<400> SEQUENCE: 91
gaggtccagc tggtgcagtc tggagctgag gtgaagaagc ctggggcctc agtgaaagtc     60
tcctgcaagg cttctggtta caccttcgt aactatggta tcagttgggt gcgacaggcc    120
cctggacaag ggcttgagtg gatgggatgg atcagcgctt acaatggtaa cacaaactat   180
```

```
gcacagaagc tccagggcag agtcaccatg accacagaca catccacgag cacagcctac    240
atggagctga ggagcctgag atctgacgac acggccgtgt attactgtgc gagagcggat    300
agcagcagct ggtacgtcgg gacttactac tactactacg gtatggacgt ctggggccaa    360
gggaccacg                                                            369

<210> SEQ ID NO 92
<211> LENGTH: 324
<212> TYPE: DNA
<213> ORGANISM: Mus musculus

<400> SEQUENCE: 92
gatgttgtga tgactcagtc tccactctcc ctgcccgtca cccctggaga gtcggcctcc    60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg gggctgagga tgttggggtt tattactgta tgcaagttct acaaactccc   300
tggacgttcg gccaagggac caaa                                          324

<210> SEQ ID NO 93
<211> LENGTH: 336
<212> TYPE: DNA
<213> ORGANISM: Mus musculus

<400> SEQUENCE: 93
caggtgcagc tacagcagtg gggcgcagga ctgttgaagc cttcggagac cctgtccctc    60
acctgcgctg tctatggtgg gtccttcagt ggttactact ggagctggat ccgccagccc   120
ccagggaagg gctggagtg gattggggaa atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtgcgag actttataaa   300
aggaggccct ttgactactg gggccagggc accctg                             336

<210> SEQ ID NO 94
<211> LENGTH: 312
<212> TYPE: DNA
<213> ORGANISM: Mus musculus

<400> SEQUENCE: 94
gaaacgacac tcacgcagtc tccaggcacc ctgtctttgt ctccagggga aagagccacc    60
ctctcctgca gggccagtca gagtgttagc agcagctact tagcctggta tcaacaaaaa   120
cctggccagg ctcccaggct cctcatctat aatgcgtcca ggagggccac tggcatccca   180
gacaggttca gtggcagtgg gtctgggca gacttcactc tcaccatcag cagactggat   240
cctgaagatt ttgcagtgta tttctgtcag cagtatggta gctcacctca gacgttcggc   300
caagggacca ag                                                       312

<210> SEQ ID NO 95
<211> LENGTH: 336
<212> TYPE: DNA
<213> ORGANISM: Mus musculus

<400> SEQUENCE: 95
caggtgcagc tacagcagtg gggcgcagga ctgttgaagc cttcggagac cctgtccctc    60
acctgcgctg tctatggtgg gtccttcagt ggttactact ggagctggat ccgccagccc   120
```

-continued

```
ccagggaagg ggctggagtg gattggggaa atcaatcata gtggaagcac caactacaac    180
ccgtccctca agagtcgagt caccatatca gtagacacgt ccaagaacca gttctccctg    240
aagctgagct ctgtgaccgc cgcggacacg gctgtgtatt actgtgcgag actttataaa    300
aggaggccct ttgactactg gggccagggc accctg                              336
```

<210> SEQ ID NO 96
<211> LENGTH: 312
<212> TYPE: DNA
<213> ORGANISM: Mus musculus

<400> SEQUENCE: 96

```
gtaacgacac tcacgcagtc tccaggcacc ctgtctttgt ctccagggga aagagccacc     60
ctctcctgca gggccagtga gagtgttagc agcaggtact tagcctggta ccagcagaga    120
cctggccagg ctcccaggct cctcatttac ggtgcatcca ggcgggccac tggctcccca    180
gagaggttca gtggcggtgg gtctgggaca gacttcactc tcaccatcag tagactggag    240
cccgaagatt tcgcagtcta ttactgtcaa cattatggta actcaccggg gacgttcggc    300
caagggacca ag                                                        312
```

<210> SEQ ID NO 97
<211> LENGTH: 119
<212> TYPE: PRT
<213> ORGANISM: Mus musculus

<400> SEQUENCE: 97

```
Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser
        115
```

<210> SEQ ID NO 98
<211> LENGTH: 106
<212> TYPE: PRT
<213> ORGANISM: Mus musculus

<400> SEQUENCE: 98

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Met
            20                  25                  30

Asn Trp Tyr Gln Gln Lys Pro Gly Lys Ala Pro Lys Arg Trp Ile Tyr
        35                  40                  45

Asp Thr Ser Lys Val Ala Ser Gly Val Pro Ala Arg Phe Ser Gly Ser
```

```
               50                  55                  60
Gly Ser Gly Thr Asp Tyr Ser Leu Thr Ile Asn Ser Leu Glu Ala Glu
 65                  70                  75                  80

Asp Ala Ala Thr Tyr Tyr Cys Gln Gln Trp Ser Ser Asn Pro Leu Thr
                 85                  90                  95

Phe Gly Gly Gly Thr Lys Val Glu Ile Lys
            100                 105

<210> SEQ ID NO 99
<211> LENGTH: 357
<212> TYPE: DNA
<213> ORGANISM: Mus musculus

<400> SEQUENCE: 99
gatgtgcagc tggtgcagag cggggcagag gtgaaaaagc ctggggcaag cgtcaaagtc      60
agttgtaaag cctccggcta cacattcact aggtatacta tgcactgggt gcgccaggcc     120
cctggccagg gctggagtg atcggctac attaacccaa gcagagggta cacaaattat      180
gctgactccg tgaaaggcag gtttactatc accaccgata agtccacctc tacagcatac     240
atggagctga gcagcctgcg aagcgaagac actgcaacct actattgcgc cggtactat      300 gacgatcatt actgtctgga ttattgggga cagggcacta ccgtgacagt ctctagt        357

<210> SEQ ID NO 100
<211> LENGTH: 318
<212> TYPE: DNA
<213> ORGANISM: Mus musculus

<400> SEQUENCE: 100
gatattgtgc tgacccagtc tccagccaca ctgagtctgt cacccggcga acgagccacc      60
ctgagctgcc gggccagcca gtccgtctct tacatgaact ggtatcagca aagcccgga     120 aaagccccta gcggtggat ctacgacaca agcaaagtgg cttccggcgt ccccgcacga      180
ttcagtggct cagggagcgg aactgactat tctctgacca ttaatagtct ggaggctgaa     240
gatgccgcta cctactattg tcagcagtgg tcaagcaacc ctctgacatt cgggggggga     300
actaaagtgg aaatcaag                                                   318

<210> SEQ ID NO 101
<211> LENGTH: 243
<212> TYPE: PRT
<213> ORGANISM: Mus musculus

<400> SEQUENCE: 101

Asp Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Arg Tyr
                 20                  25                  30

Thr Met His Trp Val Arg Gln Ala Pro Gly Gln Gly Leu Glu Trp Ile
             35                  40                  45

Gly Tyr Ile Asn Pro Ser Arg Gly Tyr Thr Asn Tyr Ala Asp Ser Val
         50                  55                  60

Lys Gly Arg Phe Thr Ile Thr Asp Lys Ser Thr Ser Thr Ala Tyr
 65                  70                  75                  80

Met Glu Leu Ser Ser Leu Arg Ser Glu Asp Thr Ala Thr Tyr Tyr Cys
                 85                  90                  95

Ala Arg Tyr Tyr Asp Asp His Tyr Cys Leu Asp Tyr Trp Gly Gln Gly
            100                 105                 110
```

```
Thr Thr Val Thr Val Ser Ser Gly Glu Gly Ser Thr Gly Ser Gly
        115                 120                 125

Gly Ser Gly Gly Ser Gly Gly Ala Asp Asp Ile Val Leu Thr Gln Ser
        130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
                180                 185                 190

Gly Val Pro Ala Arg Phe Ser Gly Ser Gly Ser Gly Thr Asp Tyr Ser
            195                 200                 205

Leu Thr Ile Asn Ser Leu Glu Ala Glu Asp Ala Ala Thr Tyr Tyr Cys
        210                 215                 220

Gln Gln Trp Ser Ser Asn Pro Leu Thr Phe Gly Gly Gly Thr Lys Val
225                 230                 235                 240

Glu Ile Lys

<210> SEQ ID NO 102
<211> LENGTH: 729
<212> TYPE: DNA
<213> ORGANISM: Mus musculus

<400> SEQUENCE: 102
gatgtgcagc tggtgcagag cggggcagag gtgaaaaagc ctgggcaag cgtcaaagtc      60 agttgtaaag cctccggcta cacattcact aggtatacta tgcactgggt gcgccaggcc    120
cctggccagg gctggagtg atcggctac attaacccaa gcagagggta cacaaattat     180
gctgactccg tgaaaggcag gtttactatc accaccgata agtccacctc tacagcatac    240
atggagctga gcagcctgcg aagcgaagac actgcaacct actattgcgc ccggtactat    300
gacgatcatt actgtctgga ttattgggga caggcacta ccgtgacagt ctctagtggg     360
gagggaacat ccactgggtc tggagggagt ggaggctcag gaggagcaga cgatattgtg    420
ctgacccagt ctccagccac actgagtctg tcacccggcg aacgagccac cctgagctgc    480
cgggccagcc agtccgtctc ttacatgaac tggtatcagc agaagcccgg aaaagcccct   540
aagcggtgga tctacgacac aagcaaagtg gcttccggcg tccccgcacg attcagtggc    600
tcagggagcg gaactgacta ttctctgacc attaatagtc tggaggctga agatgccgct    660
acctactatt gtcagcagtg gtcaagcaac cctctgacat cgggggggg aactaaagtg    720 gaaatcaag                                                            729
```